(12) United States Patent
Trend et al.

(10) Patent No.: US 11,453,658 B2
(45) Date of Patent: Sep. 27, 2022

(54) SYNTHESIS OF ANTIBACTERIAL AMINOGLYCOSIDE ANALOGS

(71) Applicant: Cipla USA, Inc., Warren, NJ (US)

(72) Inventors: Raissa Trend, Warren, NJ (US); Michael Dappen, Warren, NJ (US); Christopher E. Henry, Warren, NJ (US); Adam Aaron Goldblum, Warren, NJ (US); James Bradley Aggen, Warren, NJ (US); Ricardo Filipe de Jesus Gonçalves Mendonça, Warren, NJ (US); João Carlos Falcão Sardinha, Warren, NJ (US)

(73) Assignee: CIPLA USA, INC., Warren, NJ (US)

( * ) Notice: Subject to any disclaimer, the term of this patent is extended or adjusted under 35 U.S.C. 154(b) by 171 days.

(21) Appl. No.: 16/850,771

(22) Filed: Apr. 16, 2020

(65) Prior Publication Data
US 2020/0317652 A1 Oct. 8, 2020

Related U.S. Application Data

(63) Continuation of application No. PCT/US2018/056536, filed on Oct. 18, 2018.

(60) Provisional application No. 62/574,544, filed on Oct. 19, 2017.

(51) Int. Cl.
*C07H 1/00* (2006.01)
*C07D 407/12* (2006.01)

(52) U.S. Cl.
CPC ........ *C07D 407/12* (2013.01); *C07B 2200/13* (2013.01)

(58) Field of Classification Search
None
See application file for complete search history.

(56) References Cited

U.S. PATENT DOCUMENTS

| 4,388,233 A * | 6/1983 | Bissell | C07D 311/16 260/1 |
|---|---|---|---|
| 8,383,596 B2 | 2/2013 | Aggen et al. | |
| 8,822,424 B2 | 9/2014 | Aggen et al. | |
| 9,226,919 B2 | 1/2016 | Hirawat et al. | |
| 9,688,711 B2 | 6/2017 | Aggen et al. | |
| 2012/0214759 A1 | 8/2012 | Bruss et al. | |

FOREIGN PATENT DOCUMENTS

| WO | WO 2010/132770 | 11/2010 |
|---|---|---|
| WO | WO 2010/132777 | 11/2010 |
| WO | WO 2010/147836 | 12/2010 |
| WO | WO 2011/143497 | 11/2011 |
| WO | WO 2014/145713 | 9/2014 |

OTHER PUBLICATIONS

Isidro-Llobet et al. Eur. J. Org. Chem. (2005), pp. 3031-3039.*
International Search Report and Written Opinion dated Feb. 11, 2019, for International Application No. PCT/US2018/056536, 14 pages.
CAIRA, Crystalline polymorphism of organic compounds, Design of Organic Solids, Springer, Berlin, Heidelberg, 1998, pp. 163-208.

* cited by examiner

*Primary Examiner* — Patrick T Lewis
(74) *Attorney, Agent, or Firm* — Cooley LLP

(57) ABSTRACT

The present disclosure relates to novel methods for preparing antibacterial aminoglycoside compounds, as well as to related intermediates, and crystal forms thereof, useful in such methods.

4 Claims, 9 Drawing Sheets

SYNTHESIS OF ANTIBACTERIAL AMINOGLYCOSIDE ANALOGS

CROSS-REFERENCE TO RELATED APPLICATIONS

This application is a continuation of International Patent Application No. PCT/US2018/056536, filed Oct. 18, 2018, which claims the benefit of U.S. Provisional Application No. 62/574,544, filed Oct. 19, 2017; the contents of each of which are incorporated herein by reference in its entirety.

STATEMENT OF GOVERNMENT INTEREST

This invention was made with government support with federal funds from the Biomedical Advanced Research and Development Authority, Office of the Assistant Secretary for Preparedness and Response, Office of the Secretary, Department of Health and Human Services, under Contract No. HHSO100201000046C. The government has certain rights in this invention.

FIELD OF THE DISCLOSURE

The present disclosure relates to novel methods for preparing antibacterial aminoglycoside compounds, as well as to related intermediates and crystal forms of the intermediates useful in such methods.

BACKGROUND OF THE DISCLOSURE

At least 30% of all hospitalized patients now receive one or more courses of therapy with antibiotics, and millions of potentially fatal infections have been cured. These pharmaceutical agents have become among the most misused of those available to the practicing physician. However, one result of widespread use of antimicrobial agents has been the emergence of antibiotic-resistant pathogens, which in turn has created an ever-increasing need for new drugs.

When the antimicrobial activity of a new agent is first tested, a pattern of sensitivity and resistance is usually defined. Unfortunately, this spectrum of activity can subsequently change to a remarkable degree, because microorganisms have evolved an array of ingenious alterations that allow them to survive in the presence of antibiotics. The mechanism of drug resistance varies from microorganism to microorganism and from drug to drug.

Efforts to develop new aminoglycoside antibiotics having activity against multidrug resistant gram-negative bacteria has led to sisomicin and neomycin analogs modified at the 6'- and N-1 positions. Certain synthetic techniques for the selective functionalization of the 1-N position are known. Selective modification of the 1-N position is typically accomplished in a multistep procedure utilizing protecting groups. First, the 1-N and 3"N positions of the aminoglycoside scaffold are blocked by forming a transition metal complex with a divalent metal ion (usually zinc, nickel, copper, or cobalt). Then all other positions (6'-2'- and 3-N) are protected utilizing standard nitrogen protecting groups (typically these amines will be protected as carbamates or acetates). With 6'-2'- and 3-N positions protected, the transition metal complexes are removed and the 1-N position is modified in high selectivity. At this point, the 6'-2'- and 3-N positions are typically protected and the only remaining free amine is the secondary 3"N amine which reacts slower than the 1-N amine in typical acylation or alkylation reactions.

In contrast, selective functionalization of the 6'-N position remains a formidable problem. The 6'-N position is the most reactive position to a variety of reaction conditions and prior methods have relied on this comparatively high reactivity to functionalize or protect the 6'-N amine. However, the difference in reactivity between the 6'-N and the other positions (in particular the 2'-, 3-, and 1-N) is not great. As a result, attempts to directly functionalize the 6'-N position are complicated by the formation of isomeric byproducts and overreaction byproducts (di-functionalized or tri-functionalized aminoglycoside derivatives). The formation of byproducts in high amounts requires the implementation of purification procedures that add significant time and cost to the production of 6'-N functionalized aminoglycoside derivatives, such as those described in U.S. Pat. Nos. 8,383,596; 8,822,424; 9,266,919, 9,688,711; and U.S. Publication No. 2012-0214759.

In order to accelerate the drug discovery and development process, new methods for synthesizing aminoglycoside antibiotics are needed to provide an array of compounds that are potentially new drugs for the treatment of bacterial infections. The present disclosure may fulfill these needs and provide further related advantages.

SUMMARY OF THE DISCLOSURE

In brief, the present disclosure relates to novel methods for preparing antibacterial aminoglycoside compounds and novel intermediates and crystal forms of certain intermediates used in the new methods.

The present disclosure provides processes for preparing compounds of formula (9), which includes plazomicin, that are scaleable, reproducible at a commercial scale, and with good yields. These processes comprises reactions that can provide novel intermediate compounds obtained through experimentation and development of new combinations of reaction conditions. The processes may also comprise crystallization of certain intermediates. The crystallization of these particular intermediates unexpectedly contributes to improvements in purification (e.g., lower impurities), and can simplify the purification compared to prior methods of purification.

One aspect of the disclosure relates to a process for preparing a compound of formula (2), or a salt thereof, or solvate thereof, or an enantiomer thereof, or a diastereomer thereof comprising: (a) contacting a compound of formula (1):

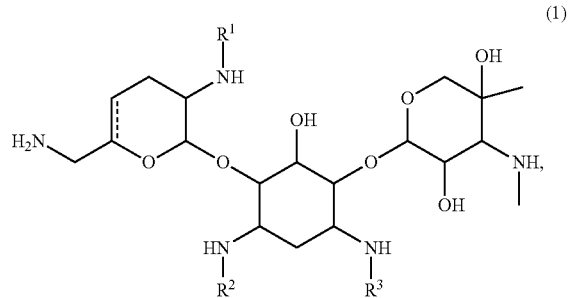

or an enantiomer thereof, or a diastereomer thereof, with 1-{[(p-nitrobenzyl)oxy]carbonyl}-1H-benzotriazole (PNZ-Bt) to form the compound of formula (2):

(2)

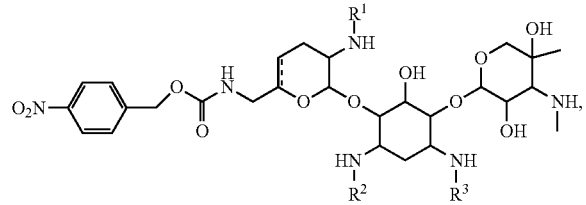

or a salt thereof, or a solvate thereof, or an enantiomer thereof, or a diastereomer thereof; wherein === is a single bond or a double bond; $R^1$ is H or $C_1$-$C_3$ alkyl; $R^2$ is H or $C_1$-$C_3$ alkyl; and $R^3$ is H or $C_1$-$C_3$ alkyl. In certain such embodiments, step (a) is performed in the presence of a solvent selected from the group consisting of dichloromethane, methanol, and a combination thereof. In some embodiments, the PNZ-Bt is present in about 1.0 to 1.2 molar equivalents to the compound of formula (1), or an enantiomer thereof, or a diastereomer thereof.

In some embodiments of the foregoing or following, === is a single bond or a double bond. In certain embodiments of the foregoing or following, === is a single bond. In other embodiments of the foregoing or following, === is a double bond. In some embodiments of the foregoing or following, $R^1$, $R^2$, or $R^3$ are H.

Another aspect of the disclosure relates to a process further comprising step (b1) or (b2):(b1) wherein when $R^1$, $R^2$, and $R^3$ are H, contacting the compound of formula (2) with a Boc protecting group reagent to yield a compound of formula (3):

(3)

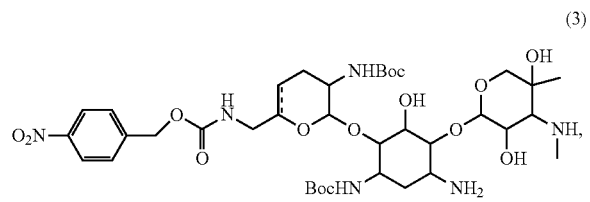

or a salt thereof, or a solvate thereof, or an enantiomer thereof, or a diastereomer thereof; or (b2) wherein when one or more of $R^1$, $R^2$, or $R^3$ is independently a $C_1$-$C_3$ alkyl, first removing said $C_1$-$C_3$ alkyl, and then contacting the compound of formula (2), or a salt thereof, or a solvate thereof, or an enantiomer thereof, or a diastereomer thereof, with a Boc protecting group reagent to yield a compound of formula (3), or a salt thereof, or a solvate thereof, or an enantiomer thereof, or a diastereomer thereof. In certain such embodiments, the Boc protecting group reagent is $Boc_2O$ or Boc-ONb. In some embodiments, step (b1) or (b2) is performed in the presence of a Lewis acid. In certain such embodiments, the Lewis acid is $Zn(OAc)_2$, $ZnCl_2$, or $Zn(OPiv)_2$. In some embodiments, the Lewis acid comprises a copper ion or a nickel ion. In some embodiments, step (b1) or (b2) is performed in the presence of triethylamine. In certain embodiments, step (b1) or (b2) is performed in the presence of methanol.

One aspect of the disclosure relates to a process further comprising: (c) contacting the compound of formula (3), or a salt thereof, or a solvate thereof, or an enantiomer thereof, or a diastereomer thereof, with

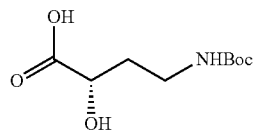 [SMILES: CC(C)(C)OC(=O)NCC[C@H](O)C(=O)O]

to yield a compound of formula (4):

(4)

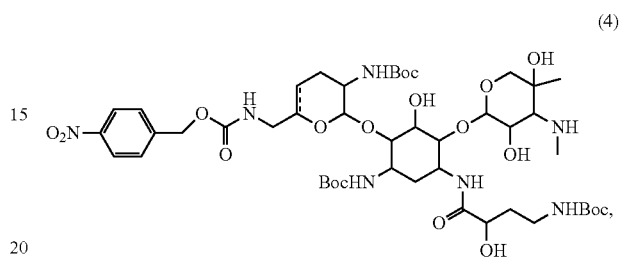

or a salt thereof, or a solvate thereof, or an enantiomer thereof, or a diastereomer thereof. In certain such embodiments, step (c) is performed in the presence of an activating reagent and a peptide coupling reagent. In certain such embodiments, the activating reagent is HOBt. In certain such embodiments, the activating reagent is present in about 0.05 to 1.0 molar equivalents to

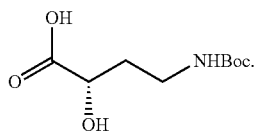 [SMILES: CC(C)(C)OC(=O)NCC[C@H](O)C(=O)O]

In some embodiments, the peptide coupling reagent is EDAC or PyBOP. In certain such embodiments, the peptide coupling reagent is present in about 1.0 to 1.4 molar equivalents to

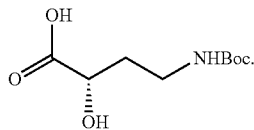 [SMILES: CC(C)(C)OC(=O)NCC[C@H](O)C(=O)O]

In some embodiments, step (c) is performed in an acidic condition. In certain such embodiments, the acidic condition is pH between around 4 and 7. In certain such embodiments, the acidic condition is pH around 5.

An aspect of the disclosure relates to a process further comprising preparing a crystalline form of compound of formula (4), or a salt thereof, or a solvate thereof, or an enantiomer thereof, or a diastereomer thereof. In some embodiments, the process further comprises isolating the compound of formula (4), or a salt thereof, or a solvate thereof, or an enantiomer thereof, or a diastereomer thereof.

Another aspect of the disclosure relates to a process further comprising: (d) contacting the compound of formula (4), or a salt thereof, or a solvate thereof, or an enantiomer thereof, or a diastereomer thereof, with Boc protecting group reagent to yield a compound of formula (5):

(5)

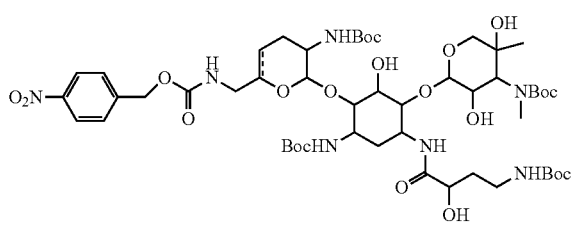

or a salt thereof, or a solvate thereof, or an enantiomer thereof, or a diastereomer thereof. In certain such embodiments, the Boc protecting group reagent is $Boc_2O$. In some embodiments, step (d) is performed in the presence of an alcohol. In certain such embodiments, the alcohol is methanol. In some embodiments, step (d) is performed at a temperature of up to about 60° C.

An aspect of the disclosure relates to a process further comprising: (e) contacting the compound of formula (5), or a salt thereof, or a solvate thereof, or an enantiomer thereof, or a diastereomer thereof, with a PNZ deprotecting reagent to yield a compound of formula (6):

(6)

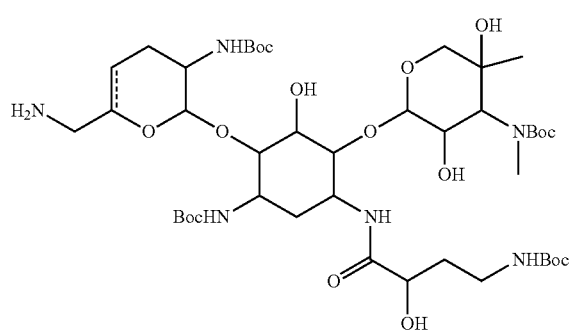

or a salt thereof, or a solvate thereof, or an enantiomer thereof, or a diastereomer thereof. In certain such embodiment, the PNZ deprotecting reagent is sodium dithionite.

Another aspect of the disclosure relates to a process further comprising preparing a crystalline form of compound of formula (6), or a salt thereof, or a solvate thereof, or an enantiomer thereof, or a diastereomer thereof. In some embodiments, the process further comprises isolating the compound of formula (6), or a salt thereof, or a solvate thereof, or an enantiomer thereof, or a diastereomer thereof.

In some embodiments, the process further comprises (f) contacting the compound of formula (6), or a salt thereof, or a solvate thereof, or an enantiomer thereof, or a diastereomer thereof, with

HO~~~$LG^1$, wherein $LG^1$ is a leaving group, to yield a compound of formula (7):

(7)

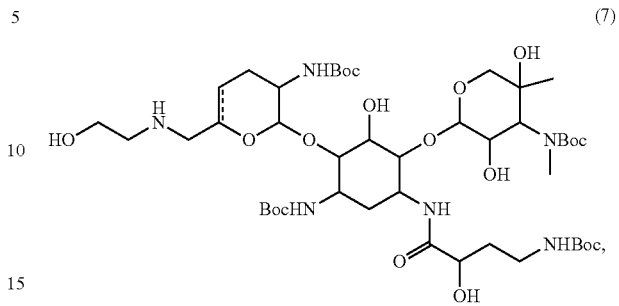

or a salt thereof, or a solvate thereof, or an enantiomer thereof, or a diastereomer thereof. In certain such embodiments, the leaving group is iodo. In some embodiments, the

HO~~~$LG^1$ is present in about 1.0 to 1.5 molar equivalents to the compound of formula (6). In some embodiments, step (f) is performed in conditions substantially free of water. In certain embodiments, step (f) is performed in the presence of a solvent selected from the group consisting of acetonitrile, acetone, and combination thereof. In some embodiments, step (f) is performed in the presence of $NaHCO_3$. In certain embodiments, step (f) is performed at a temperature of about 30° C. to 40° C. In some embodiments, step (f) further comprises adding 1,4-diazabicyclo[2.2.2]octane (DABCO) to a reaction mixture.

One aspect of the disclosure relates to a process further comprising preparing a crystalline form of compound of formula (7), or a salt thereof, or a solvate thereof, or an enantiomer thereof, or a diastereomer thereof. Another aspect of the disclosure relates to a process further comprises isolating the compound of formula (7), or a salt thereof, or a solvate thereof, or an enantiomer thereof, or a diastereomer thereof.

Another aspect of the disclosure relates to a process further comprising: (g) contacting the compound of formula (7), or a salt thereof, or a solvate thereof, or an enantiomer thereof, or a diastereomer thereof, with a Boc removing reagent to yield a compound of formula (8):

(8)

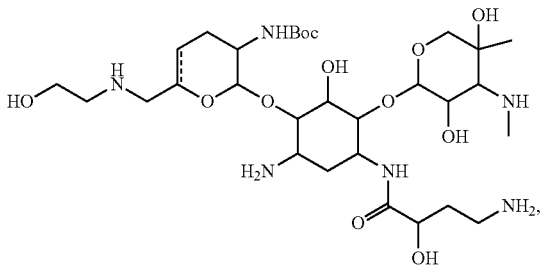

or a salt thereof, or a solvate thereof, or an enantiomer thereof, or a diastereomer thereof. In some embodiments of step (g), the Boc removing reagent is TFA, thereby yielding a TFA salt of compound of formula (8), or a solvate thereof, or an enantiomer thereof, or a diastereomer thereof. In some embodiments, the process further comprises removing the TFA salt to afford a compound of formula (8), or a solvate thereof, or an enantiomer thereof, or a diastereomer thereof.

One aspect of the disclosure relates to a process further comprising: (h) performing a salt formation with an acid to yield a salt of a compound of formula (8), or a solvate thereof, or an enantiomer thereof, or a diastereomer thereof. In some embodiments, the acid in step (h) is sulfuric acid, thereby yielding a sulfate salt of a compound of formula (9):

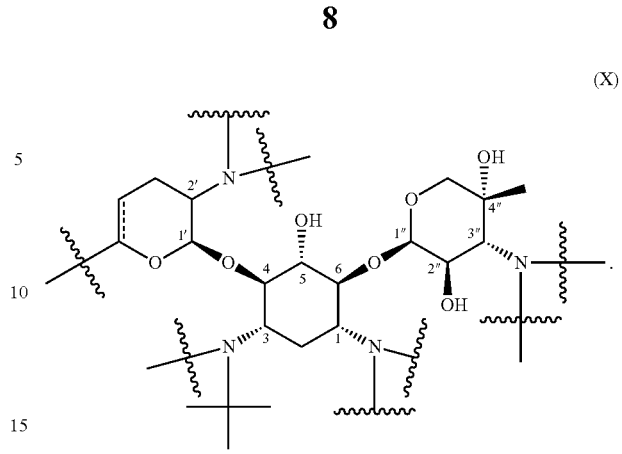

(X)

In some embodiments of any of the following or foregoing, the stereochemistry at carbon atoms 1, 3, 4, 5, 6, 1', 2', 1", 2", 3", 4", and 1-z in formulae (4)-(9) are indicated as in formula (Y), wherein ⁓ indicates a point of attachment to hydrogen or a moiety:

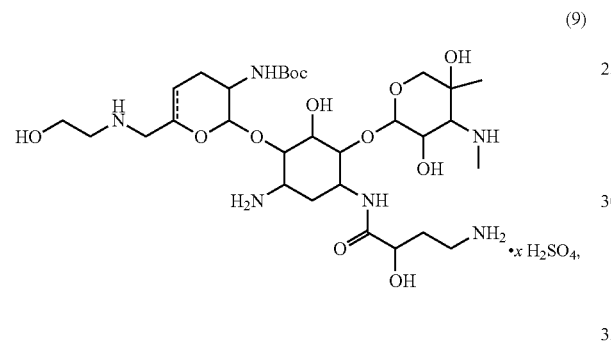

(9)

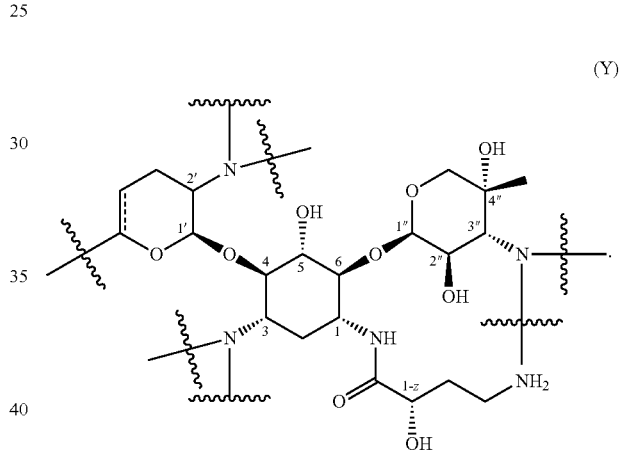

(Y)

or a solvate thereof, or an enantiomer thereof, or a diastereomer thereof, wherein x is 1 to 5.

In some embodiments of any of the following or foregoing, the stereochemistry at carbon atoms 1, 3, 4, 5, 6, 1', 2', 1", 2", 3", and 4" in formulae (1)-(3) are indicated as in formula (X), wherein ⁓ indicates a point of attachment to hydrogen or a moiety:

One aspect of the disclosure relates to a process for preparing a compound of formula (5):

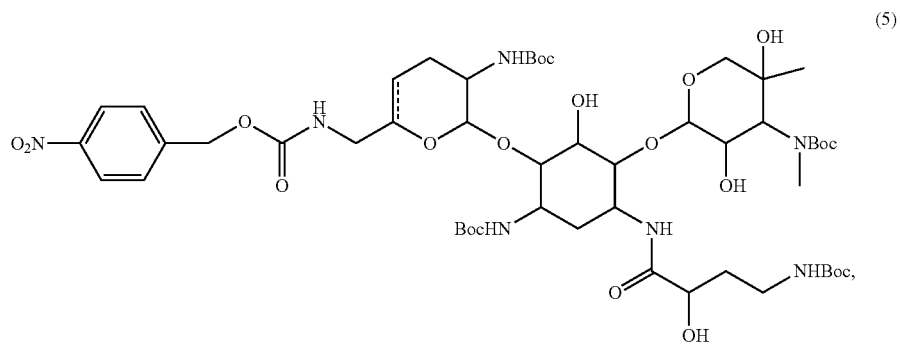

(5)

or a salt thereof, or a solvate thereof, or an enantiomer thereof, or a diastereomer thereof, the process comprising:
(a) contacting a compound of formula (4):

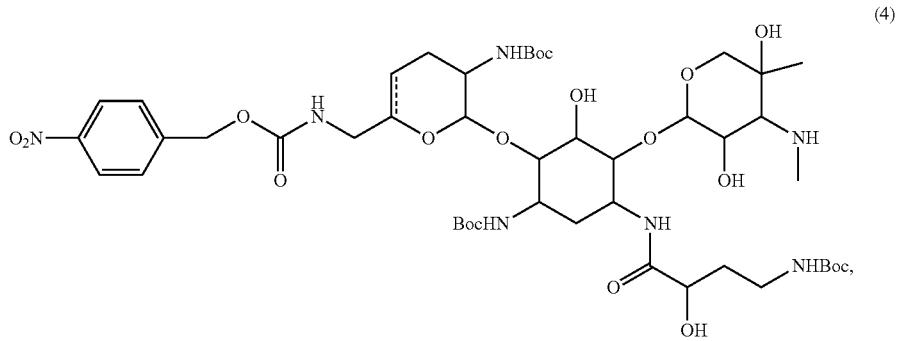

(4)

or a salt thereof, or a solvate thereof, or an enantiomer thereof, or a diastereomer thereof, with a Boc protecting group reagent, wherein === is a single bond or a double bond. In some embodiments, the compound of formula (4), or a salt thereof, or a solvate thereof, or an enantiomer thereof, or a diastereomer thereof, is prepared by contacting a compound of formula (3):

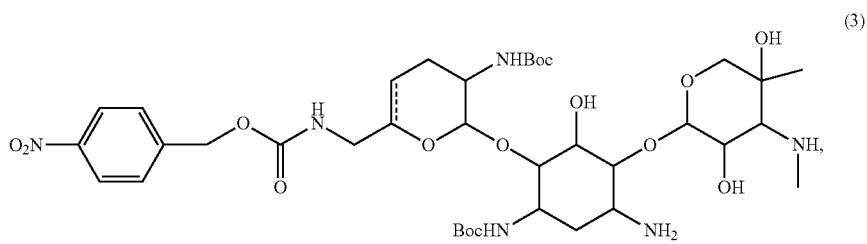

(3)

or a salt thereof, or a solvate thereof, or an enantiomer thereof, or a diastereomer thereof, with

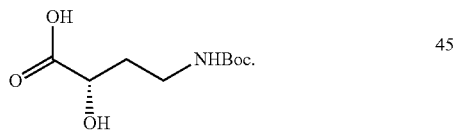

In other embodiments, the compound of formula (3), or a salt thereof, or a solvate thereof, or an enantiomer thereof, or a diastereomer thereof, is prepared by (b1) contacting a compound of formula (2a):

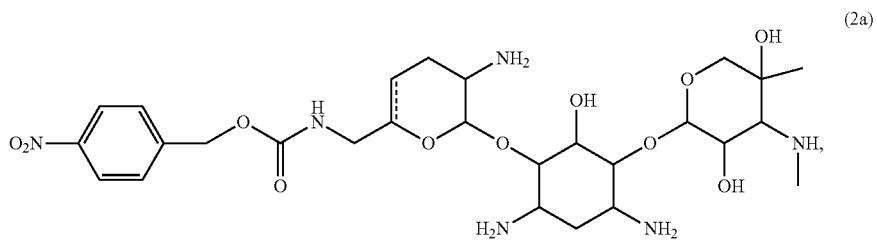

(2a)

or a salt thereof, or a solvate thereof, or an enantiomer thereof, or a diastereomer thereof, with a Boc protecting group reagent; or (b2) removing $C_1$-$C_3$ alkyl in a compound of formula (2):

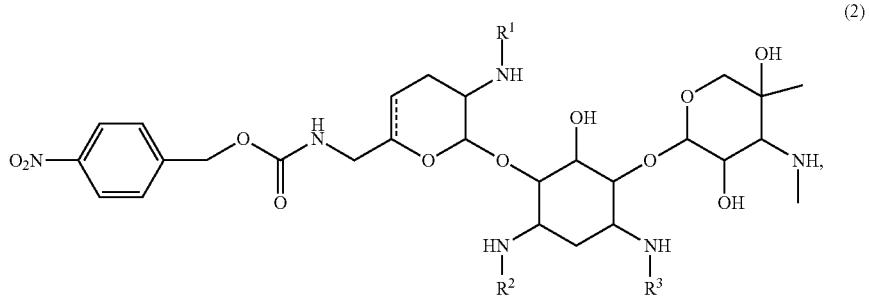

(2)

or a salt thereof, or a solvate thereof, or an enantiomer thereof, or a diastereomer thereof; wherein $R^1$ is H or $C_1$-$C_3$ alkyl; $R^2$ is H or $C_1$-$C_3$ alkyl; and $R^3$ is H or $C_1$-$C_3$ alkyl, and wherein one or more of $R^1$, $R^2$, or $R^3$ is independently a $C_1$-$C_3$ alkyl; and then contacting the compound of formula (2) with a Boc protecting group reagent.

In some embodiments, the compound of formula (2), or a salt thereof, or solvate thereof, or an enantiomer thereof, or a diastereomer thereof, is prepared by contacting a compound of formula (1):

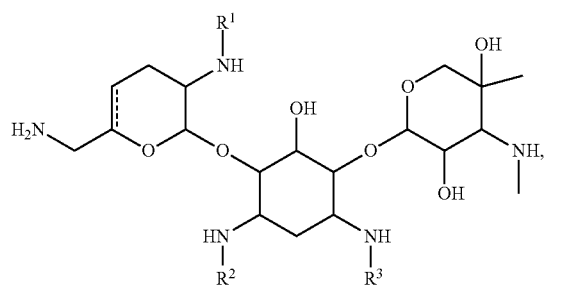

(1)

or an enantiomer thereof, or a diastereomer thereof, with 1-{[(p-nitrobenzyl)oxy]carbonyl}-1H-benzotriazole (PNZ-Bt). In certain embodiments, the Boc protecting group reagent in step (a), (b1), or (b2) is $Boc_2O$. In some embodiments, step (a), (b1), or (b2) is performed in the presence of an alcohol. In certain such embodiments, the alcohol is methanol. In some embodiments, step (a), (b1), or (b2) is performed at a temperature of up to about 60° C.

One aspect of the disclosure relates to a process for preparing a compound of formula (7):

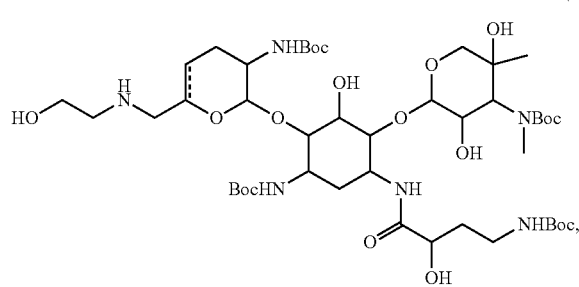

(7)

or a salt thereof, or a solvate thereof, or an enantiomer thereof, or a diastereomer thereof, the process comprising:
(f) contacting a compound of formula (6),

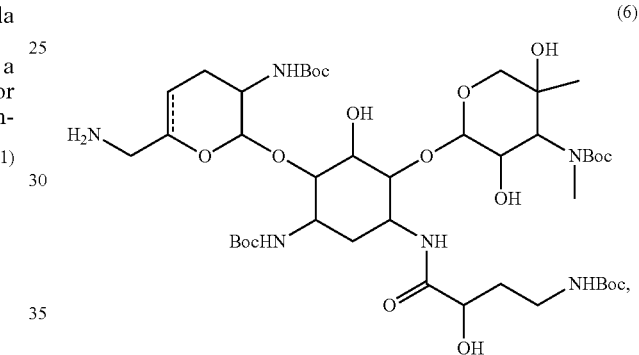

(6)

or a salt thereof, or a solvate thereof, or an enantiomer thereof, or a diastereomer thereof, with

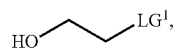

wherein $LG^1$ is a leaving group, and wherein === is a single bond or a double bond. In certain such embodiments, the leaving group is iodo. In some embodiments, the

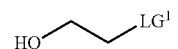

is present in about 1.0 to 1.5 molar equivalents to the compound of formula (6). In some embodiments, step (f) is performed in conditions substantially free of water. In certain embodiments, step (f) is performed in the presence of a solvent selected from the group consisting of acetonitrile, acetone, and combination thereof. In some embodiments, step (f) is performed in the presence of $NaHCO_3$. In some embodiments, step (f) is performed at a temperature of about 30° C. to 40° C. In some embodiments, step (f) further comprises adding 1,4-diazabicyclo[2.2.2]octane (DABCO) to a reaction mixture.

Another aspect of the disclosure relates to a process wherein a compound of formula (6), or a salt thereof, or a solvate thereof, or an enantiomer thereof, or a diastereomer thereof, is prepared by contacting a compound of formula (5):

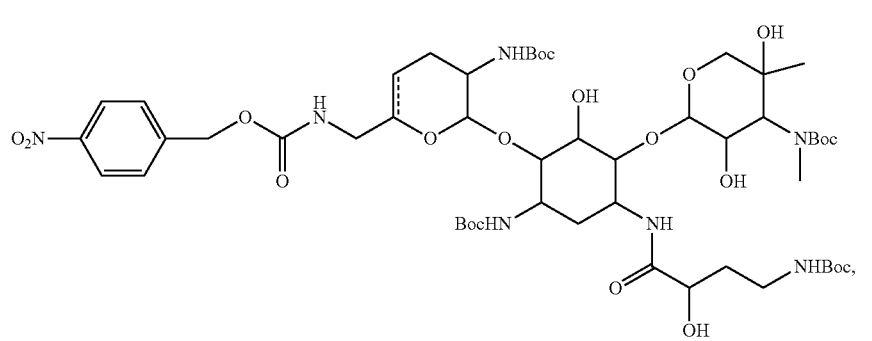

(5)

or a salt thereof, or a solvate thereof, or an enantiomer thereof, or a diastereomer thereof, with a PNZ deprotecting reagent.

One aspect of the disclosure relates to compound of formula (4):

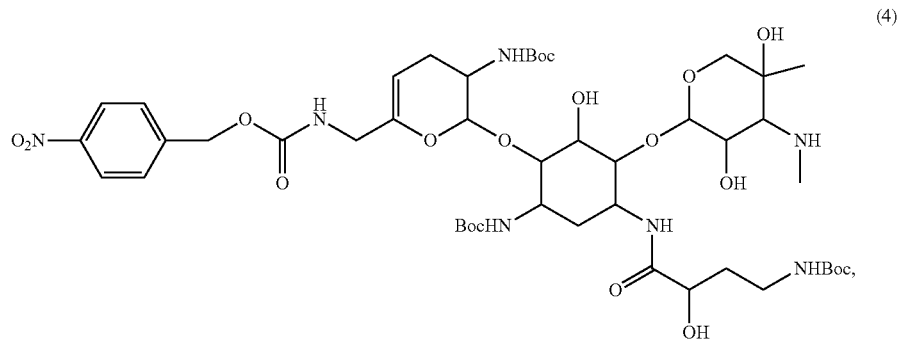

(4)

or a salt thereof, or a solvate thereof, or an enantiomer thereof, or a diastereomer thereof. In certain such embodiments, the compound of formula (4) is of the following formula:

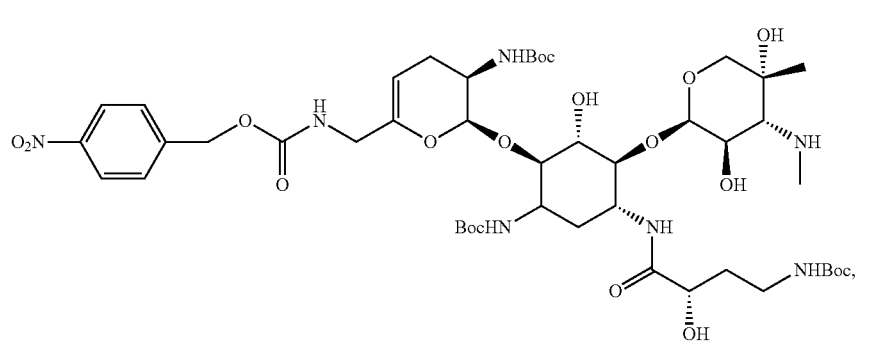

(4a)

or a salt thereof, or a solvate thereof.

Another aspect of the disclosure relates to crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl) carbamate, Formula (4a), or a solvate thereof.

One aspect of the disclosure relates to a process for preparing crystalline tert-butyl ((2S,3R)-2-(((1R,2S,3S,4R, 6S)-6-((tert-butoxycarbonyl)amino)-4-((S)-4-((tert-butoxycarbonyl)amino)-2-hydroxybutanamido)-3-(((2R,3R,4R, 5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, Formula (4a), or a solvate thereof, comprising:
(a) treating Formula (4a), or a salt thereof, or a solvate thereof, with acetonitrile to produce a solution;
(b) heating the solution from step (a);
(c) adding water to the heated solution of step (b);
(d) cooling the solution from step (c);

(e) charging the solution from step (d) with a seed crystal; and
(f) isolating the resulting solids to yield crystalline Formula (4a), or a solvate thereof.

Another aspect of the disclosure relates to crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof.

One aspect of the disclosure relates to a process for preparing crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof, comprising:
(a) treating Formula (6), or a salt thereof, or a solvate thereof, with isopropyl acetate (IPAc) to produce a solution;
(b) adding water to the solution of step (a) to produce a mixture;
(c) adding dichloromethane to the mixture from step (b) to produce a mixture;
(d) charging the mixture from step (c) with a seed crystal;
(e) isolating the resulting solids to yield crystalline Formula (6a), or a solvate thereof.

In certain such embodiments, step (d) is performed at a low temperature.

Another aspect of the disclosure relates to a compound of formula (7):

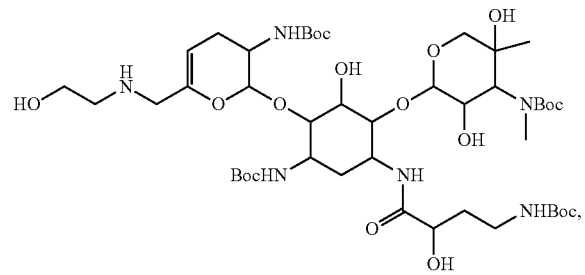

or a salt thereof, or solvate thereof, or an enantiomer thereof, or a diastereomer thereof. In certain such embodiments, the compound of formula (7) is of the following formula:

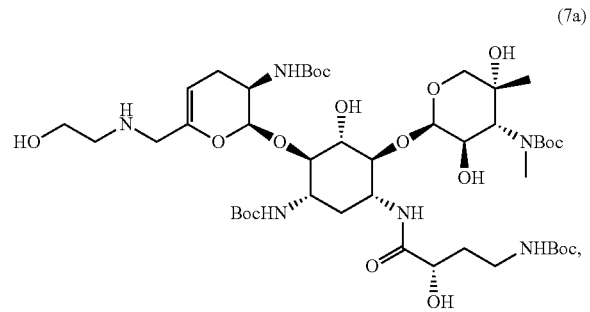 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

(7a)

or a salt thereof, or a solvate thereof.

One aspect of the disclosure relates to crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof.

Another aspect of the disclosure relates to a process for preparing crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof, comprising:
(a) treating Formula (7a), or a salt thereof, or a solvate thereof, with isopropyl acetate (IPAc) to produce a solution;
(b) adding acetonitrile to the solution of step (a) to produce a mixture;
(c) charging the mixture from step (b) with a seed crystal;
(d) isolating the resulting solids to yield crystalline Formula (7a), or a solvate thereof.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

BRIEF DESCRIPTION OF THE DRAWINGS

Various aspects of the present disclosure are illustrated by reference to the accompanying drawings.
FIG. 1 depicts the XRPD spectrum of Compound 4a.
FIG. 2 depicts the TGA profile of Compound 4a.
FIG. 3 depicts the DSC profile of Compound 4a.
FIG. 4 depicts the XRPD spectrum of Compound 6a.
FIG. 5 depicts the TGA profile of Compound 6a.
FIG. 6 depicts the DSC profile of Compound 6a.
FIG. 7 depicts the XRPD spectrum of Compound 7a.
FIG. 8 depicts the TGA profile of Compound 7a.
FIG. 9 depicts the DSC profile of Compound 7a.

DETAILED DESCRIPTION OF THE DISCLOSURE

Figure 1:
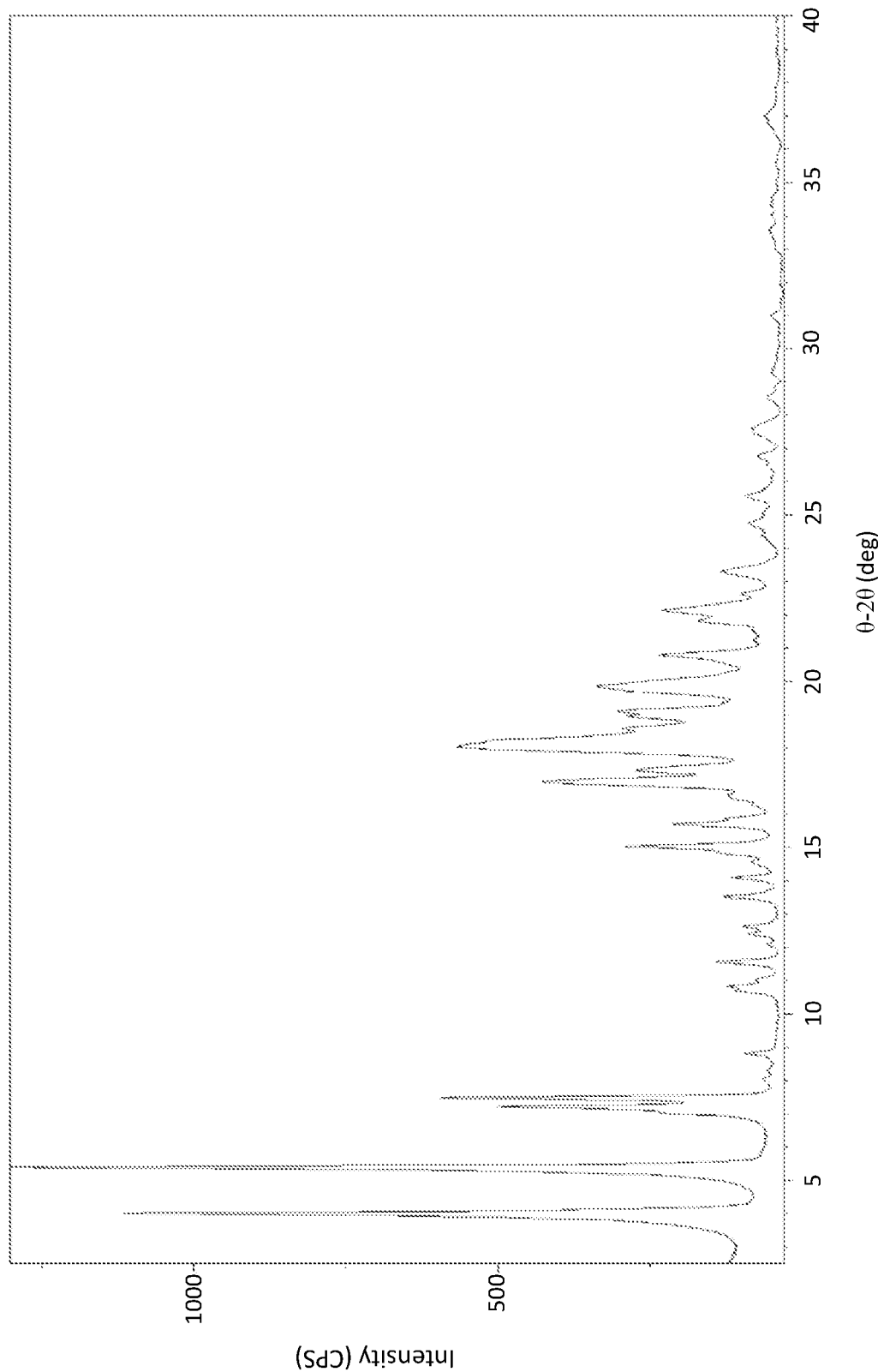

The present disclosure relates to novel methods for preparing antibacterial aminoglycoside compounds, as well as to related intermediates useful in such methods and certain crystal forms of particular intermediates.

As discussed above, the present disclosure provides processes for preparing compounds of formula (9), which includes plazomicin sulfate, that is scaleable and reproducible at commercial scale with a good yield. The processes comprise combinations of reactions and conditions that can provide certain novel intermediate compounds. The processes also include in particular embodiments the crystallization of certain intermediates, in which the crystallization surprisingly aids in the purification process (e.g., by purging impurities and thereby lowering impurity levels), thus also providing for greater ease of purification compared to prior purification processes.

In one aspect, the disclosure relates to a process for preparing compounds of formula (2):

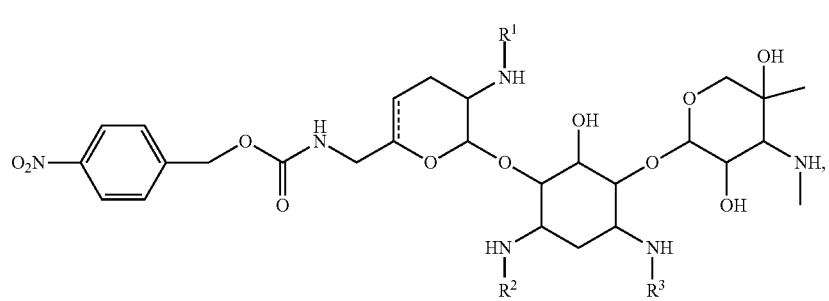

(2)

or a salt thereof, or a solvate thereof, or an enantiomer thereof, or a diastereomer thereof, wherein === is a single bond or a double bond; $R^1$ is H or $C_1$-$C_3$ alkyl; $R^2$ is H or $C_1$-$C_3$ alkyl; and $R^3$ is H or $C_1$-$C_3$ alkyl.

In another aspect, the disclosure relates to a process for preparing compounds of formula (3):

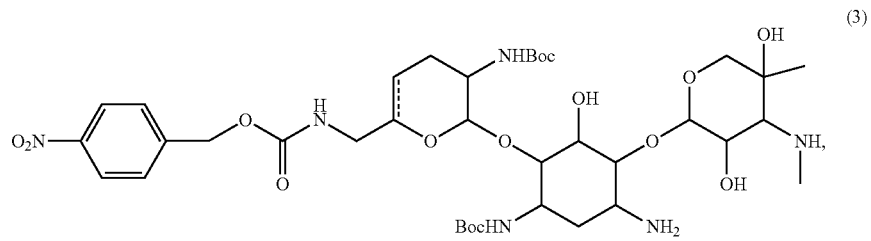

(3)

or a salt thereof, or a solvate thereof, or an enantiomer thereof, or a diastereomer thereof, wherein === is a single bond or a double bond.

In one aspect, the disclosure relates to a process for preparing compounds of formula (4):

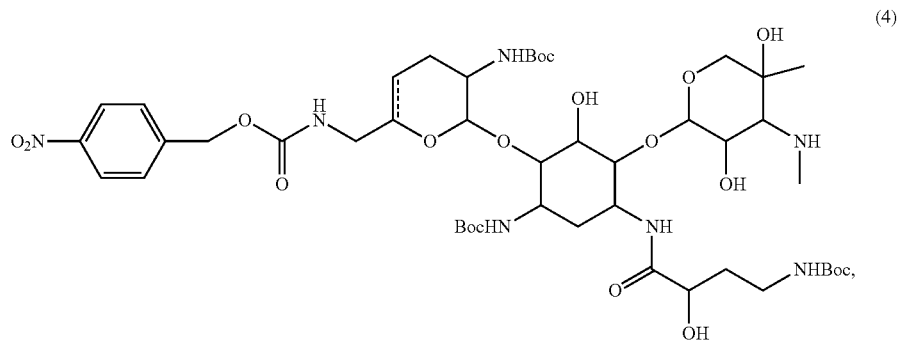 [SMILES: CNC1C(O)C(OC2C(NC(=O)C(O)CCNC(=O)OC(C)(C)C)CC(NC(=O)OC(C)(C)C)C(OC3OC(CNC(=O)OCc4ccc([N+](=O)[O-])cc4)=CCC3NC(=O)OC(C)(C)C)C2O)OCC1(C)O]

(4)

or a salt thereof, or a solvate thereof, or an enantiomer thereof, or a diastereomer thereof, wherein === is a single bond or a double bond.

In another aspect, the disclosure relates to a process for preparing compounds of formula (5):

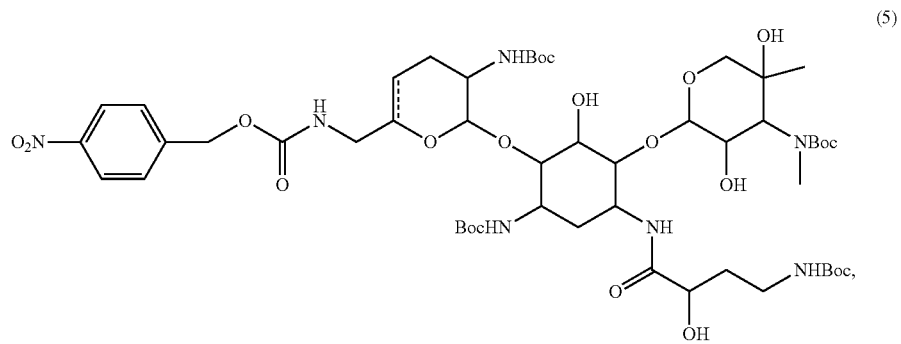

(5)

or a salt thereof, or a solvate thereof, or an enantiomer thereof, or a diastereomer thereof, wherein === is a single bond or a double bond.

In one aspect, the disclosure relates to a process for preparing compounds of formula (6):

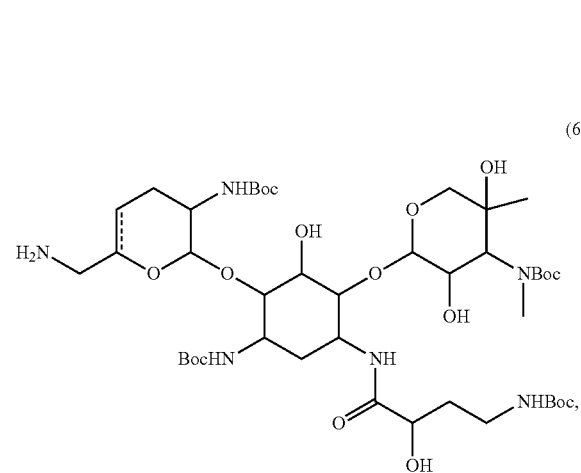

(6)

or a salt thereof, or a solvate thereof, or an enantiomer thereof, or a diastereomer thereof, wherein === is a single bond or a double bond.

In another aspect, the disclosure relates to a process for preparing compounds of formula (7):

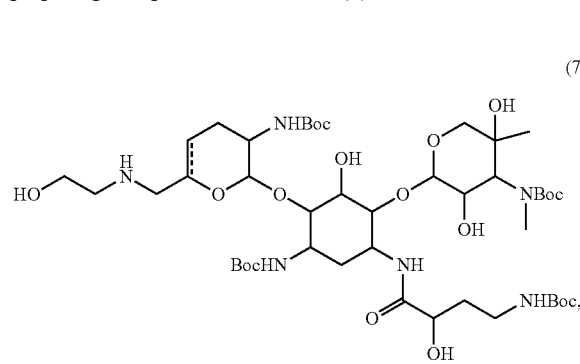

(7)

or a salt thereof, or a solvate thereof, or an enantiomer thereof, or a diastereomer thereof, wherein === is a single bond or a double bond.

In some aspects, the disclosure relates to a process for preparing compounds of formula (8):

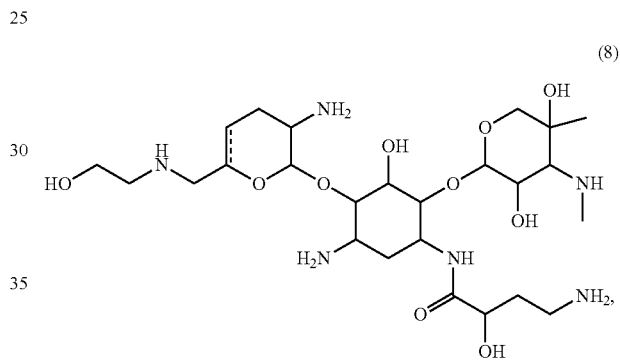

(8)

or a salt thereof, or a solvate thereof, or an enantiomer thereof, or a diastereomer thereof, wherein === is a single bond or a double bond.

In another aspect, the disclosure relates to a process for preparing a sulfate salt of a compound of formula (9):

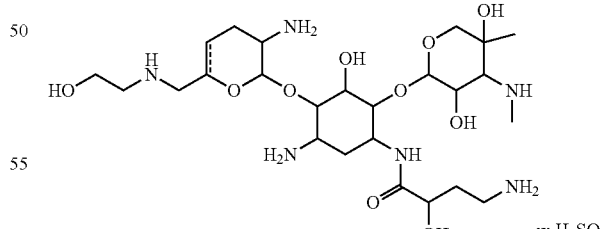

(9)

or a solvate thereof, or an enantiomer thereof, or a diastereomer thereof, wherein x is 1 to 5 and wherein === is a single bond or a double bond.

In some embodiments, the stereochemistry at carbon atoms 1, 3, 4, 5, 6, 1', 2', 1", 2", 3", and 4" in formulae (1)-(3) are indicated as in formula (X), wherein ⁓ indicates a point of attachment to hydrogen or a moiety:

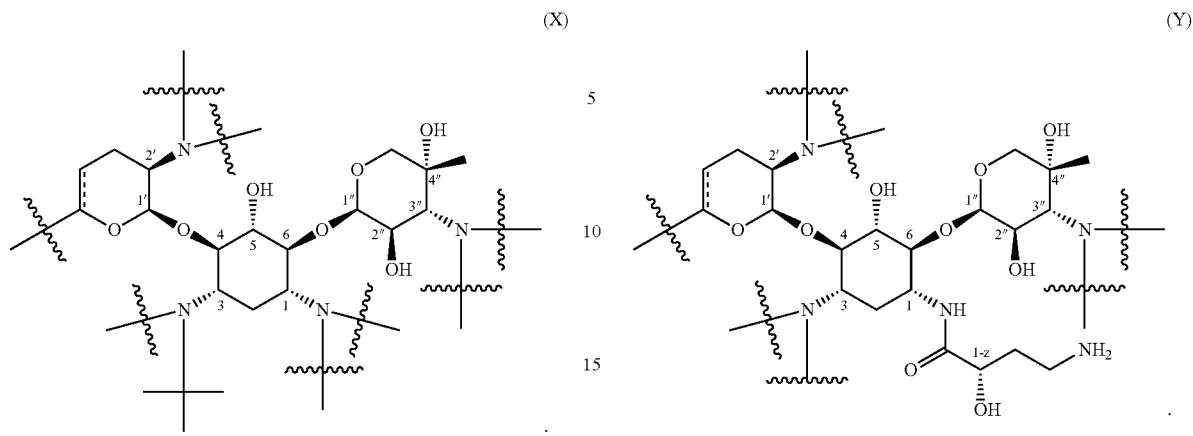

In some embodiments, the stereochemistry at carbon atoms 1, 3, 4, 5, 6, 1', 2', 1", 2", 3", 4", and 1-z in formulae (4)-(9) are indicated as in formula (Y), wherein ⌇ indicates a point of attachment to hydrogen or a moiety:

In one aspect, the disclosure relates to a compound of formula (4):

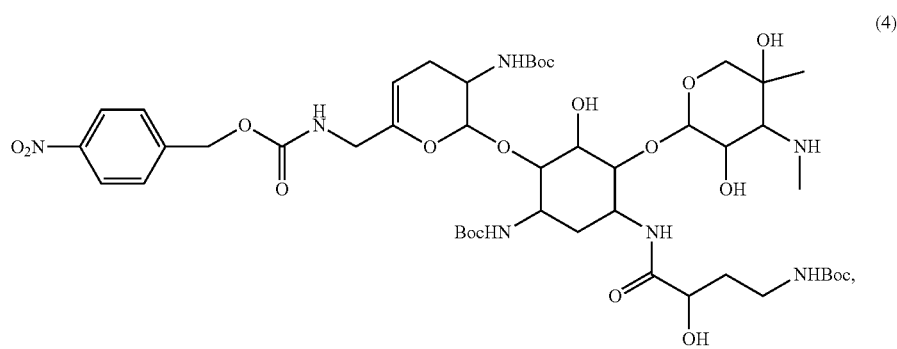

or a salt thereof, or a solvate thereof, or an enantiomer thereof, or a diastereomer thereof.

In some embodiments, the compound of formula (4) is of the following formula:

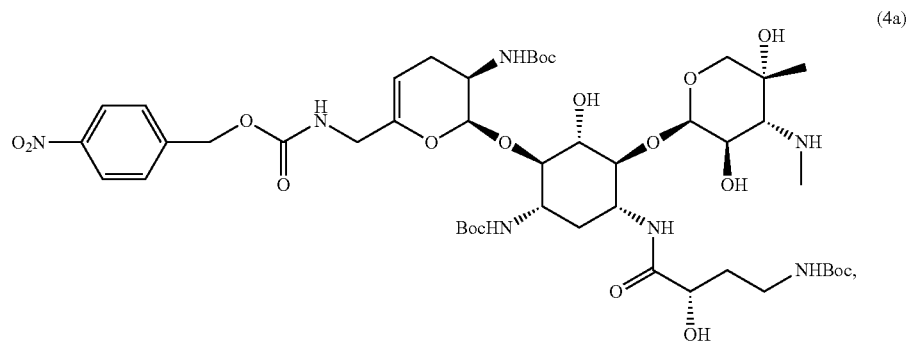 [SMILES: CN[C@@H]1[C@@H](O)[C@@H](O[C@@H]2[C@@H](O)[C@H](O[C@H]3OC(CNC(=O)OCc4ccc([N+](=O)[O-])cc4)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

or a salt thereof, or a solvate thereof.

In some embodiments, the disclosure also relates to crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino) methyl)-3,4-dihydro-2H-pyran-3-yl) carbamate, Formula (4a), or a solvate thereof.

In some embodiments, the disclosure also relates to crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate, Formula (6a):

(6a)

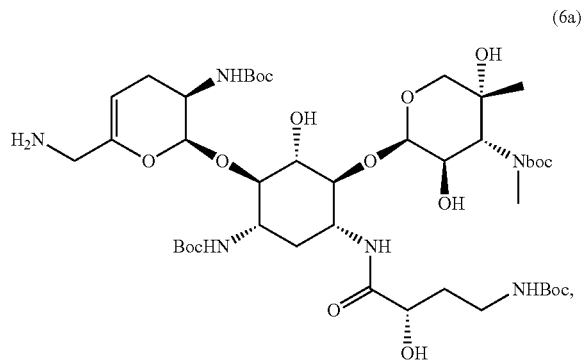

or a solvate thereof.

In one aspect, the disclosure relates to a compound of formula (7):

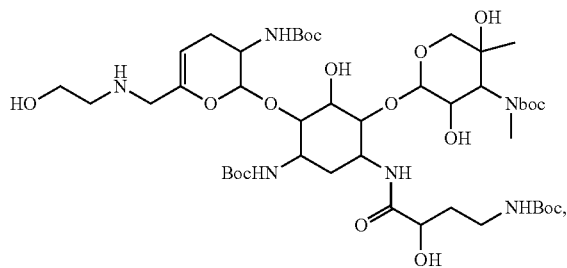

or a salt thereof, or solvate thereof, or an enantiomer thereof, or a diastereomer thereof.

In some embodiments, the compound of formula (7) is of the following formula:

(7a)

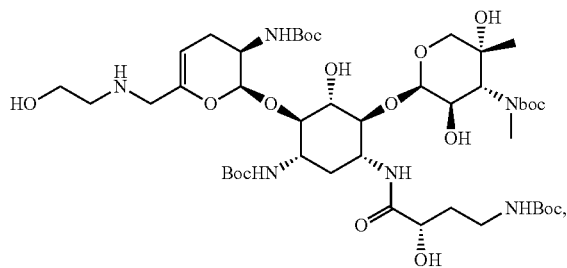

or a salt thereof, or solvate thereof.

In some embodiments, the disclosure relates to crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl) carbamate, Formula (7a), or a solvate thereof.

Terms and Abbreviations

The articles "a" and "an" as used in this disclosure may refer to one or more than one (i.e., to at least one) of the grammatical object of the article. By way of example, "an element" means one element or more than one element.

As used in this disclosure, "and/or" may mean either "and" or "or" unless indicated otherwise.

As used herein, === may refer to a single bond or a double bond.

"Alkyl" may refer to a straight or branched chain saturated hydrocarbon. $C_1$-$C_3$alkyl groups contain 1 to 3 carbon atoms. Examples of a $C_1$-$C_3$alkyl group include, but are not limited to, methyl, ethyl, and propyl.

"Boc protecting group reagent" may refer to a reagent that may be used to install a Boc protecting group on an amine group. Examples of Boc protecting group reagents include, but are not limited to, Boc anhydride ($Boc_2O$), N-tert-butoxycarbonylimidazole, 2-(tert-butoxycarbonyloxyimino)-2-phenylacetonitrile, 2-(tert-butoxycarbonylthio)-4,6-dimethylpyrimidine, 1-tert-butoxycarbonyl-1,2,4-triazole, tert-butyl phenyl carbonate, N-(tert-butoxycarbonyloxy)phthalimide, tert-butyl 2,4,5-trichlorophenyl carbonate, and tert-butyl ((4R,7S)-1,3-dioxo-1,3,3a,4,7,7a-hexahydro-2H-4,7-methanoisoindol-2-yl) carbonate (Boc-ONb).

"Boc removing reagent" may refer to a reagent that may be used to cleave a Boc protecting group on an amine group. Examples of Boc removing reagents include, but are not limited to, TFA, aqueous phosphoric acid, methanesulfonic acid (MSA or MsOH), $SnCl_4$, HCl/dioxane, and HCl/MeOH. Further examples of Boc removing reagents include HCl, $H_2SO_4$ and PTSA (p-toluenesulfonic acid or tosylic acid).

A "Lewis acid" may refer to a compound or ionic species that can accept an electron pair from a donor compound. Examples of Lewis acids include, but are not limited to, $Zn(OAc)_2$, $ZnCl_2$, $Zn(OPiv)_2$. Additionally, other metal cations, such as copper and nickel cations, may act as Lewis acids.

"PNZ protecting group reagent" may refer to a reagent that may be used to install a p-nitrobenzyloxycarbonyl protecting group on an amine group. Examples of PNZ protecting group reagents may include, but are not limited to, 1-{[(p-nitrobenzyl)oxy]carbonyl}-1H-benzotriazole and 4-nitrobenzyl 1H-benzo[d]imidazole-1-carboxylate.

The terms "1-{[(p-nitrobenzyl)oxy]carbonyl}-1H-benzotriazole" or "PNZ-Bt" may refer to compounds of the formula:

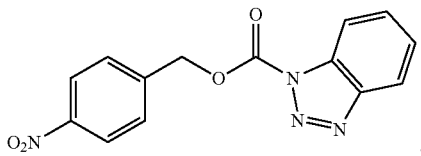

The term "4-nitrobenzyl 1H-benzo[d]imidazole-1-carboxylate" may refer to compounds of the formula:

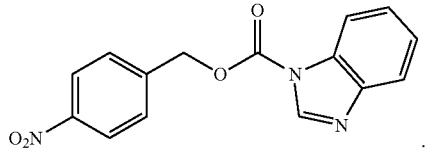 [SMILES: O=C(OCc1ccc([N+](=O)[O-])cc1)n1cnc2ccccc21]

"PNZ deprotecting reagent" may refer to a reagent that may be used to cleave a p-nitrobenzyloxycarbonyl protecting group on an amine group. Examples of PNZ deprotecting agents may include, but are not limited to, sodium dithionite and hydrogenation with $H_2$ and Pd/C or $PtO_2$.

The term "protecting group," as used herein, may refer to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups may be selectively incorporated into aminoglycosides described herein as precursors. For example, an amino group can be placed into a compound described herein as an azido group that can be chemically converted to the amino group at a desired point in the synthesis. Generally, groups are protected or present as a precursor that will be inert to reactions that modify other areas of the parent molecule for conversion into their final groups at an appropriate time. Further, representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, 2-trimethylsilylethoxycarbonyl (Teoc), 1-methyl-1-(4-biphenylyl)ethoxycarbonyl (Bpoc), t-butoxycarbonyl (Boc), allyloxycarbonyl (Alloc), 9-fluorenylmethyloxycarbonyl (Fmoc), benzyloxycarbonyl (Cbz), p-nitrobenzyloxycarbonyl (PNZ), formyl, acetyl, trihaloacetyl (e.g., trifluoroacetyl), benzoyl, nitrophenylacetyl, 2-nitrobenzenesulfonyl, phthalimido, and dithiasuccinoyl.

Preparation of a Compound of Formula (9) and Intermediates Thereof:

The present disclosure includes processes, methods, reagents, and intermediates for the synthesis of a compound of formula (9), which has the structure:

(9)

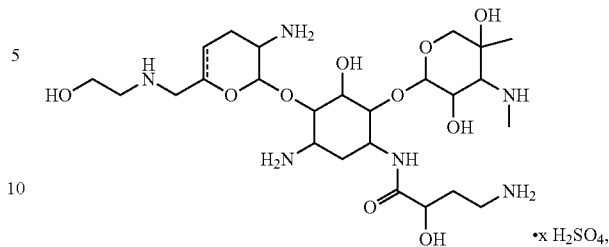

or a solvate thereof, or an enantiomer thereof, or a diastereomer thereof, wherein === is a single bond or a double bond and wherein x is 1 to 5.

In some embodiments, the compound of formula (9) is plazomicin sulfate, which has the structure:

Plazomicin sulfate

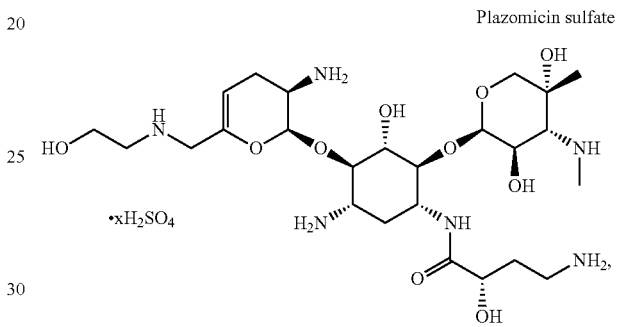

or a solvate thereof, wherein x is 1 to 5.

Plazomicin sulfate may also be referred to as (2"R,3"R, 4"R,5"R)-2"-[(1S,2S,3R,4S,6R)-4-amino-6-[(2'''S)-4'''-amino-2'''-hydroxybutanamido)amino]-3-[(2'S,3'R)-3'-amino-6'-((2-hydroxyethylamino)methyl)-3',4'-dihydro-2H-pyran-2'-yloxy]-2-hydroxycyclohexyloxy]-5''-methyl-4''-(methylamino)tetrahydro-2H-pyran-3'',5''-diol sulfate. Plazomicin may also be referred to as:

6'-(hydroxyethyl)-1-(HABA)-sisomicin;

6'-(2-hydroxy-ethyl)-1-(4-amino-2(S)-hydroxy-butyryl)-sisomicin;

(2S)-4-Amino-N-[(1R,2S,3S,4R,5S)-5-amino-4-[[(2S,3R)-3-amino-6-[(2-hydroxyethylamino)methyl]-3,4-dihydro-2H-pyran-2-yl]oxy]-2-[(2R,3R,4R,5R)-3,5-dihydroxy-5-methyl-4-(methylamino)oxan-2-yl]oxy-3-hydroxycyclohexyl]-2-hydroxybutanamide;

Butanamide, 4-amino-N-[(1R,2S,3S,4R,5S)-5-amino-4-[[(2S,3R)-3-amino-3,4-dihydro-6-[[(2-hydroxyethyl)amino]methyl]-2H-pyran-2-yl]oxy]-2-[[3-deoxy-4-C-methyl-3-(methylamino)-β-L-arabinopyranosyl]oxy]-3-hydroxycyclohexyl]-2-hydroxy-, (2S)—;

D-Streptamine, O-2-amino-2,3,4,6-tetradeoxy-6-[(2-hydroxyethyl)amino]-a-D-glycero-hex-4-enopyranosyl-(1→4)-O-[3-deoxy-4-C-methyl-3-(methylamino)-b-L-arabinopyranosyl-(1→6)]-N1-[(2S)-4-amino-2-hydroxy-1-oxobutyl]-2-deoxy-;

O-2-Amino-2,3,4,6-tetradeoxy-6-[(2-hydroxyethyl)amino]-a-D-glycero-hex-4-enopyranosyl-(1→4)-O-[3-deoxy-4-C-methyl-3-(methylamino)-b-L-arabinopyranosyl-(1→6)]-N1-[(2S)-4-amino-2-hydroxy-1-oxobutyl]-2-deoxy-D-streptamine; and (2S)-4-amino-N-[(1R,2S,3S,4R,5S)-5-amino-4-{[(2S,3R)-3-amino-6-{[(2-hydroxyethyl)amino]methyl}-3,4-dihydro-2H-pyran-2-yl]oxy}-2-{[3-deoxy-4-C-methyl-3-(methylamino)-β-L-arabinopyranosyl]oxy}-3-hydroxycyclohexyl]-2-hydroxybutanamide.

Conventional atom numbering for plazomicin is shown below:
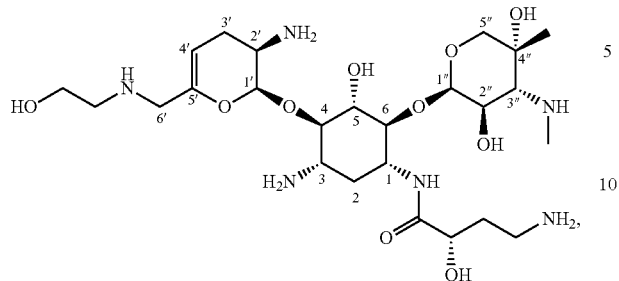
A process for the preparation of a compound of formula (9) and certain intermediates obtained in the preparation of a compound of formula (9) is illustrated in Scheme 1 below and is discussed in greater detail herein.
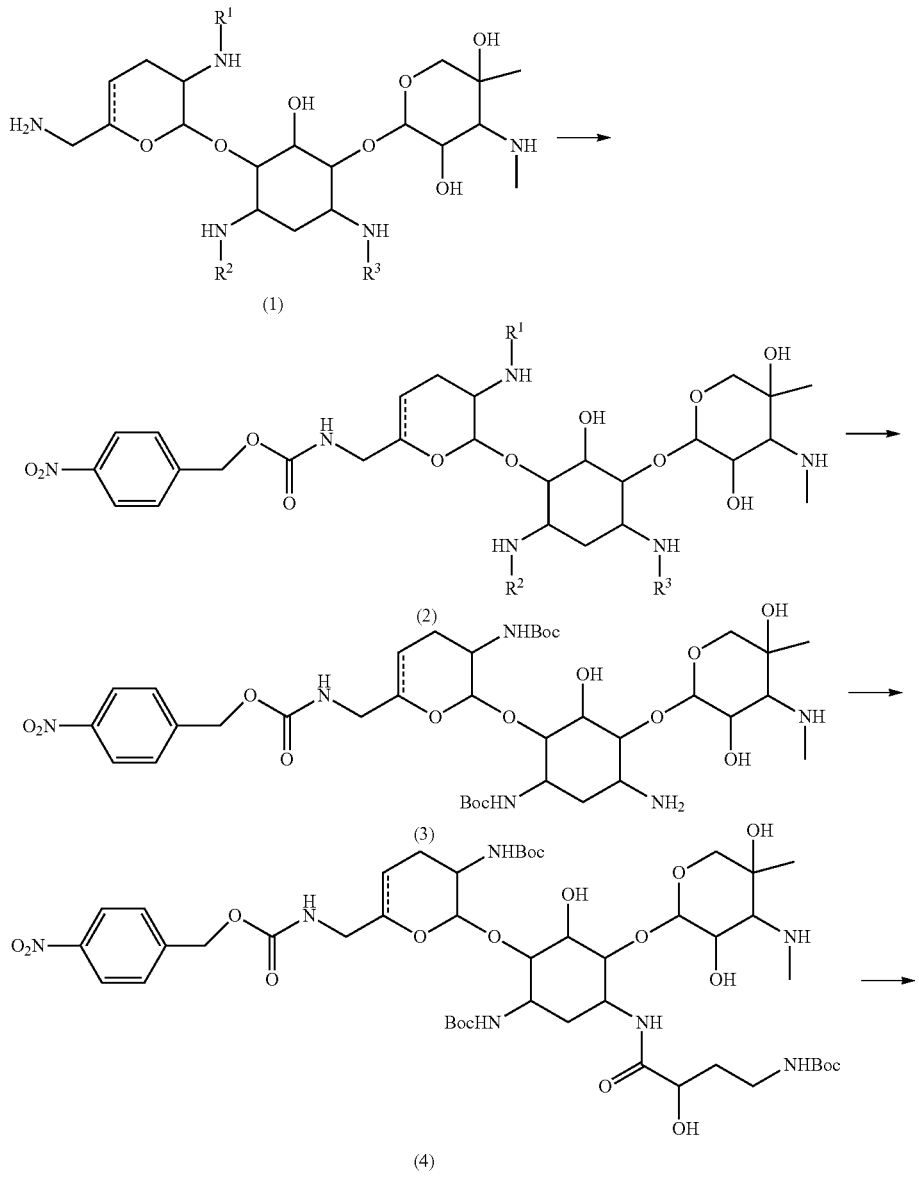

-continued
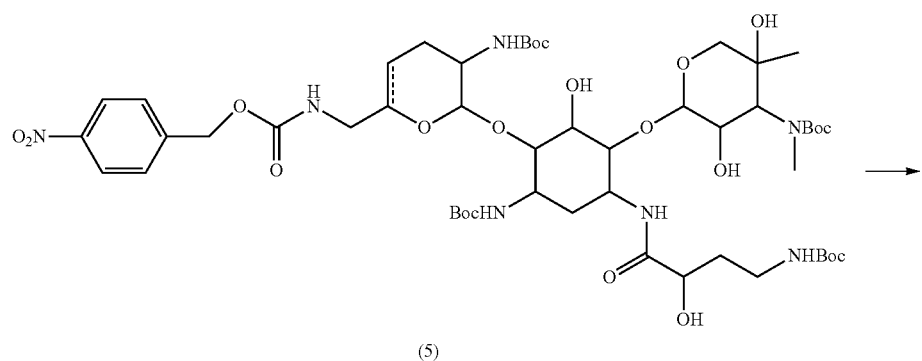
(5)
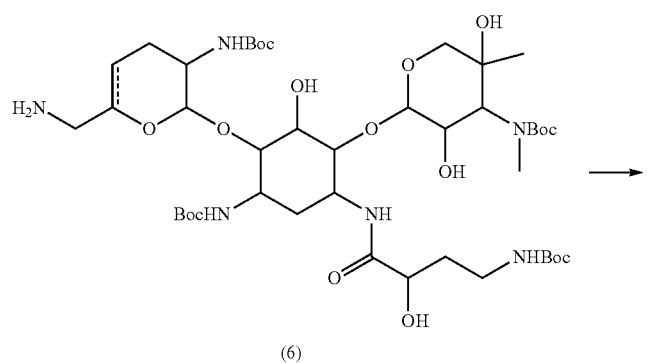
(6)
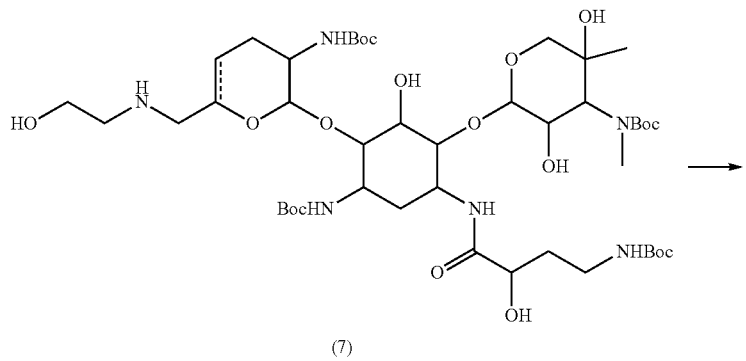
(7)
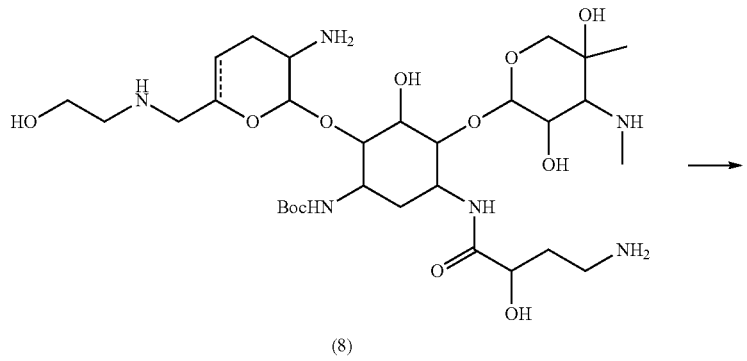
(8)

-continued

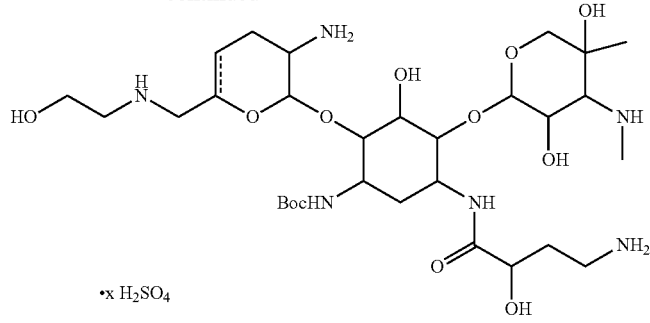

(9)

As noted above, the present disclosure provides processes for preparing compounds of formula (9), which includes plazomicin sulfate, that is not only scaleable to commercial quantities, but which is also reliably reproducible batch to batch at such commercial scale and which also has a good yield. Thus the synthetic methods and purification processes described herein outline a scaleable, economically favorable process for the preparation of compounds of formula (9), and intermediates thereof, which does not rely on expensive and/or elaborate steps during the preparation, thus making this methodology especially amenable to large scale production of antibiotics.

The processes comprise reactions that can yield novel intermediate compounds through a combination of reaction conditions and steps. For example, selective functionalization of the 6'-N position was a challenge. However, as described in the present disclosure, the reaction of compound of formula (6) to compound of formula (7) as described herein unexpectedly yielded an monoalkylation products, whereas under normal circumstances there is the expectation that such reactions would lead to over-alkylation.

The processes may also comprise crystallization of certain intermediates. As described herein the crystallization of certain intermediates aids in the purification process (e.g., lowers impurities) and simplifies the purification process compared to prior purification processes. For example, prior purification processes included precipitation, which can provide poorer purity and/or properties of the isolated compound. Precipitation steps can also lower yield and lead to greater batch-to-batch variability in the level of impurities. Crystallization, as described herein, can act to purge impurities. Additionally, although significant effort is required to initially determine appropriate crystallization conditions, once the crystallization conditions are determined, the process is straightforward and reproducible. For example, samples of crystals can be collected from a prior round of crystallization to be used as seed crystals for future crystallizations. As discussed below, compounds of formula (4), (6), and (7) can be crystallized.

The compounds described herein and the process of making the compounds may include salts of the compounds described herein. Representative salts include, but are not limited to, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A salt may also include acid addition salts. An "acid addition salt" may refer to those salts which retain the biological effectiveness and properties of the freebases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

The compounds described herein and the process of making the compounds may include solvates of the compounds described herein. The term "solvate" may refer to a complex of variable stoichiometry formed by a solute and solvent. Such solvents for the purpose of the disclosure may not interfere with the biological activity of the solute. Examples of suitable solvents may include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

Those skilled in the art will recognize if a stereocenter exists in any of the compounds described herein and the process of making the compounds. Accordingly, the present disclosure includes both possible stereoisomers (unless the stereochemistry is specified herein) and includes not only racemic compounds but the individual enantiomers and/or diastereomers as well. Additionally, those skilled in the art will recognize if a positional or geometric isomer exists for a compound described herein. Accordingly, the present disclosure includes all possible positional or geometric isomers (unless the isomer is specified herein). In the structures shown herein, where the stereochemistry of any particular chiral atom is not specified or the geometric or positional isomer is not specified, then all stereoisomers and geometric or positional isomers are contemplated and included in the compounds described herein and the process of making the compounds. Where stereochemistry or geometric or positional isomer is specified, then that stereochemistry or geometric or position isomer is so specified and defined.

The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. The compounds described herein and the process of making the compounds may include stereoisomers.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. The compounds described herein and the process of making the compounds may include enantiomers. Each compound herein disclosed may include all the enantiomers that conform to the general structure of the compound (unless the enantiomer is specified herein). The compounds may be in a racemic or enantiomerically pure form, or any other form in terms of stereochemistry (unless the stereochemistry is specified herein). In some embodiments the compounds are the (S)-enantiomer. In other embodiments the compounds are the (R)-enantiomer. In yet other embodiments, the compounds are the (+) or (−) enantiomers. In some embodiments, compounds described herein may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer may be substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the compound mixture. For example, if a compound mixture contains 98 grams of a first enantiomer and 2 grams of a second enantiomer, it would be said to contain 98 mol percent of the first enantiomer and only 2 mol percent of the second enantiomer.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" may refer to any member of this set of compounds. In some examples presented, the synthetic route may produce a single diastereomer or a mixture of diastereomers. The compounds described herein and the process of making the compounds may include diastereomers. In some embodiments, the compounds described herein may be enriched to provide predominantly one diastereomer of a compound disclosed herein. A diastereomerically enriched mixture may comprise, for example, at least 60 mol percent of one diastereomer, or more preferably at least 75, 99, 95, 96, 97, 98, 99, or even 100 mol percent.

In addition, the compounds described herein and the process of making the compounds include all geometric and positional isomers. For example, if a compound described herein incorporates a double bond or a fused ring, both the cis- and trans-forms, as well as mixtures, may be embraced within the scope of the disclosure. If the compound contains a double bond, the substituent may be in the E or Z configuration (unless the configuration is specified herein). If the compound contains a disubstituted cycloalkyl, the cycloalkyl substituent may have a cis or trans configuration (unless the configuration is specified herein).

The compounds described herein may further include all isotopically labeled compounds. An "isotopically" or "radiolabeled" compound is a compound where one or more atoms are replaced or substituted by an atom having an atomic mass or mass number different from the atomic mass or mass number typically found in nature (i.e., naturally occurring). For example, in some embodiments, in the compounds described herein hydrogen atoms may be replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3H$, and carbon 14, i.e., $^{14}C$, are particularly useful for this purpose in view of their ease of incorporation and ready means of detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Suitable isotopes that may be incorporated in compounds described herein may include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$ and $^{13}N$, may be useful in Positron Emission Topography (PET) studies.

The compounds of any of the formulae described herein may be prepared by methods known in the art of organic synthesis as set forth in part by the following synthetic schemes and examples in conjunction with the guidance provided herein. In the schemes described below, it is understood that protecting groups for sensitive or reactive groups may be employed where necessary in accordance with general principles or chemistry in accordance with the guidance provided herein. Protecting groups may be manipulated according to standard methods of organic synthesis (T. W. Greene and P. G. M. Wuts, "Protective Groups in Organic Synthesis," Third edition, Wiley, New York 1999). These groups may be removed at a convenient stage of the compound synthesis using methods that are readily apparent to those skilled in the art based on the detailed teaching provided herein. The selection processes, as well as the reaction conditions and order of their execution, shall be consistent with the present disclosure.

The following Schemes 2-5 also illustrate the synthesis of a compound of formula (9) and its intermediates.

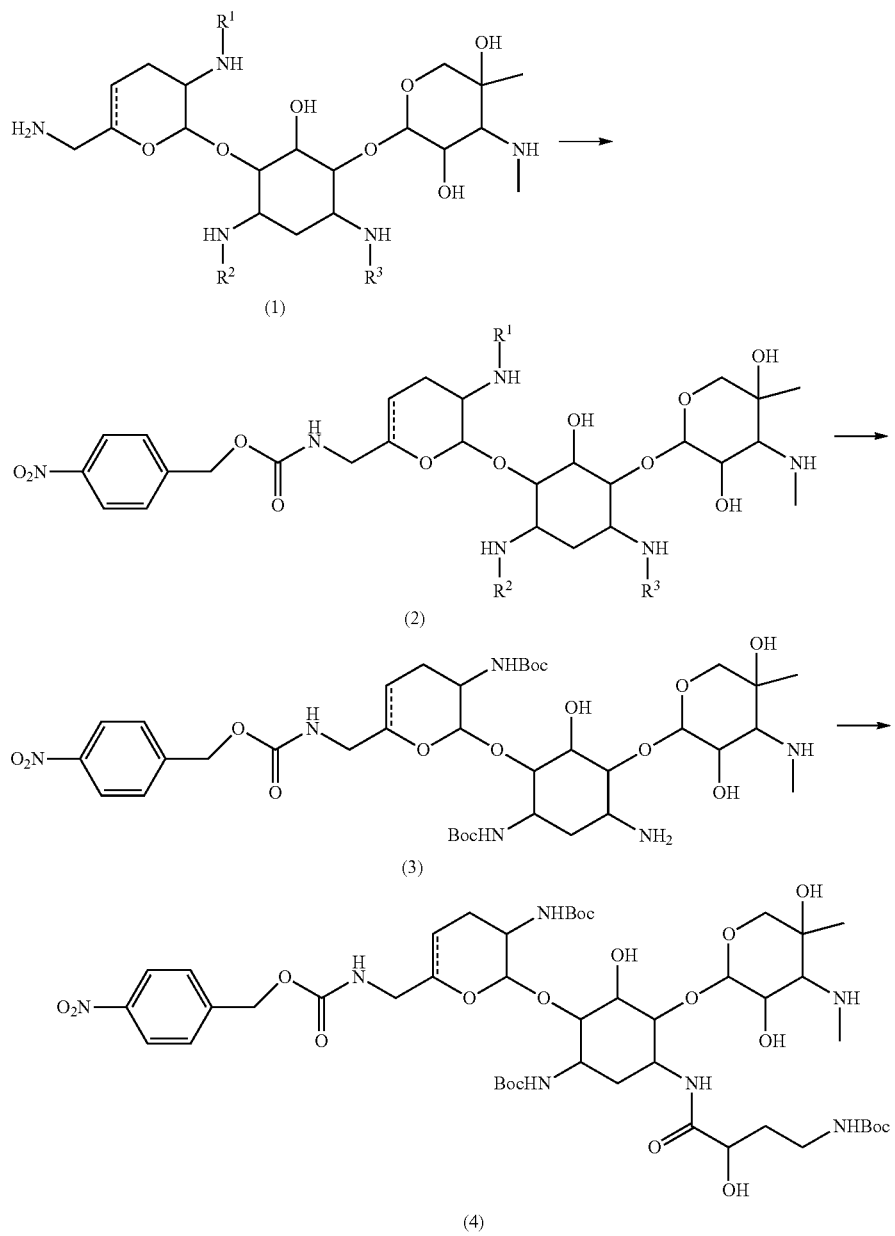

Scheme 2: Synthesis of a Compound of Formula (4)

Scheme 2 shows the synthesis of a compound of formula (4), or a salt thereof, or a solvate thereof, or an enantiomer thereof, or a diastereomer thereof. In Scheme 2, $R^1$ is H or $C_1$-$C_3$ alkyl; $R^2$ is H or $C_1$-$C_3$ alkyl; and $R^3$ is H or $C_1$-$C_3$ alkyl; and === is a single bond or a double bond.

Synthesis of a Compound of Formula (2)

With continued reference to Scheme 2, in some embodiments, the reactions detailed in Scheme 2 are performed at a temperature of up to about 60° C. A compound of formula (1), or an enantiomer thereof, or a diastereomer thereof, may be contacted with a PNZ protecting group reagent to form a compound of formula (2), or a salt thereof, or a solvate thereof, or an enantiomer thereof, or a diastereomer thereof. In some embodiments, the PNZ protecting group reagent is selected from 1-{[(p-nitrobenzyl)oxy]carbonyl}-1H-benzo-triazole (PNZ-Bt) and 4-nitrobenzyl 1H-benzo[d]imidazole-1-carboxylate. In some embodiments, the PNZ protecting group reagent is PNZ-Bt.

In certain such embodiments, the PNZ protecting group reagent may be present in the reaction in about 1.0 to 1.2 molar equivalents to the compound of formula (1), or an enantiomer thereof, or a diastereomer thereof. In some embodiments, the reaction between a compound of formula (1), or an enantiomer thereof, or a diastereomer thereof, and PNZ protecting group reagent may be performed in the presence of a solvent selected from the group consisting of dichloromethane, an alcohol, and a combination thereof. In certain such embodiments, the alcohol is methanol. The presence of methanol may increase the selectivity of the reaction when $R^1$, $R^2$, and/or $R^3$ are H. In other embodiments, the reaction between a compound of formula (1), or an enantiomer thereof, or a diastereomer thereof, and PNZ protecting group reagent may be performed in the presence of a solvent selected from the group consisting of dichloromethane, ethanol, and a combination thereof.

In some embodiments, the compound of formula (2) can be used in the next reaction without substantial purification.

In certain embodiments, $R^1$, $R^2$, and $R^3$ in a compound of formula (1), or an enantiomer thereof, or a diastereomer thereof, are H. In certain such embodiments, the compound of formula (2) is a compound of formula (2a):

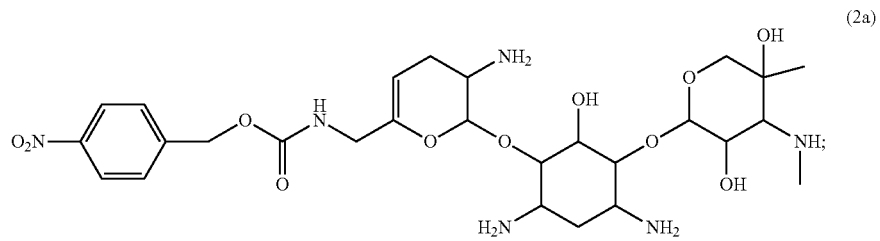

(2a)

or a salt thereof, or a solvate thereof, or an enantiomer thereof, or a diastereomer thereof. In certain such embodiments, === is a double bond.

In some embodiments, the compound of formula (1) contacted with a PNZ protecting group reagent may be sisomicin freebase (shown below):

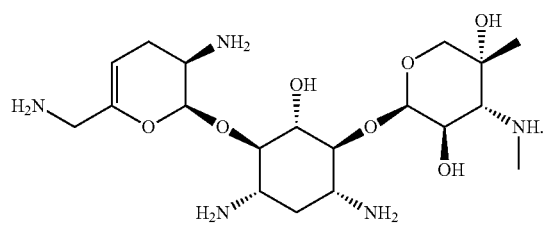 [SMILES: CN[C@@H]1[C@@H](O)[C@@H](O[C@@H]2[C@@H](O)[C@H](O[C@H]3OC(CN)=CC[C@H]3N)[C@@H](N)C[C@H]2N)OC[C@]1(C)O]

In certain such embodiments, the compound of formula (2) is a compound of formula (2b):

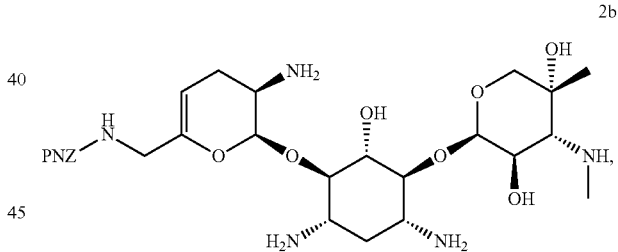

(2b)

or a salt thereof, or a solvate thereof.

Synthesis of a Compound of Formula (3)

With continued reference to Scheme 2, a compound of formula (3):

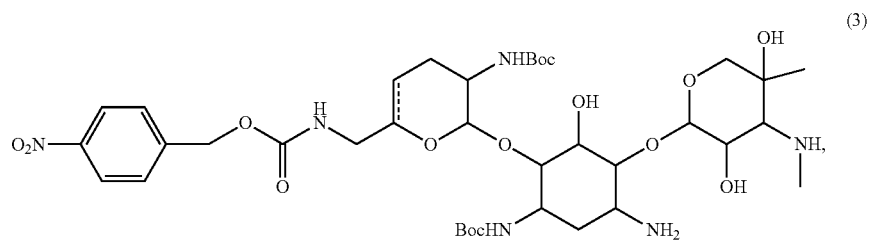

(3)

or a salt thereof, or a solvate thereof, or an enantiomer thereof, or a diastereomer thereof, may be synthesized from a compound of formula (2), or a salt thereof, or a solvate thereof, or an enantiomer thereof, or a diastereomer thereof. In certain such embodiments, === is a double bond.

When $R^1$, $R^2$, and $R^3$ are H, the compound of formula (2), or a salt thereof, or a solvate thereof, or an enantiomer thereof, or a diastereomer thereof, may be contacted with a Boc (tert-butyloxycarbonyl) protecting group reagent to yield a compound of formula (3), or a salt thereof, or a solvate thereof, or an enantiomer thereof, or a diastereomer thereof. In other embodiments, when one or more of $R^1$, $R^2$, or $R^3$ is independently a $C_1$-$C_3$ alkyl, the one or more $C_1$-$C_3$ alkyl groups are removed and the compound of formula (2), or a salt thereof, or a solvate thereof, or an enantiomer thereof, or a diastereomer thereof, may be contacted with a Boc protecting group reagent to yield the compound of formula (3), or a salt thereof, or a solvate thereof, or an enantiomer thereof, or a diastereomer thereof.

In some embodiments, the Boc protecting group reagent is di-tert-butyl dicarbonate, N-(t-butoxycarbonyloxy)-5-norbornene-endo-2,3-dicarboximide, N-tert-butoxycarbonylimidazole, 2-(tert-butoxycarbonyloxyimino)-2-phenylacetonitrile, 2-(tert-butoxycarbonylthio)-4,6-dimethylpyrimidine, 1-tert-butoxycarbonyl-1,2,4-triazole, tert-butyl phenyl carbonate, N-(tert-butoxycarbonyloxy)phthalimide, or tert-butyl 2,4,5-trichlorophenyl carbonate. In some embodiments, the Boc protecting group reagent is $Boc_2O$ (Boc anhydride; di-tert-butyl dicarbonate) or Boc-ONb (N-(t-butoxycarbonyloxy)-5-norbornene-endo-2,3-dicarboximide). In certain such embodiments, the Boc protecting group reagent is $Boc_2O$. In certain such embodiments, the Boc protecting group reagent is Boc-ONb.

The reaction between the compound of formula (2), or a salt thereof, or a solvate thereof, or an enantiomer thereof, or a diastereomer thereof, and the Boc protecting group reagent may be performed in the presence of a Lewis acid. In certain such embodiments, the Lewis acid is $Zn(OAc)_2$, $ZnCl_2$, or $Zn(OPiv)_2$. Alternatively, the reaction between the compound of formula (2), or a salt thereof, or a solvate thereof, or an enantiomer thereof, or a diastereomer thereof, and the Boc protecting group reagent may also be performed in the presence of a Lewis acid comprising a copper ion or a nickel ion.

Further, the reaction between the compound of formula (2), or a salt thereof, or a solvate thereof, or an enantiomer thereof, or a diastereomer thereof, and the Boc protecting group reagent may be performed in the presence of an amine. In some embodiments, the amine is 1,8-diazabicyclo[5.4.0]undec-7-ene (DBU), pyridine, piperidine, 4-dimethylaminopyridine (DMAP), 2,6-lutidine, dimethylaniline, N-methylpyrrilidone, N-diisopropylethylamine, N-methylimidazole, N-ethyldimethylamine, trimethylamine, or triethylamine. In some embodiments, the amine is triethylamine.

Additionally, the reaction between the compound of formula (2), or a salt thereof, or a solvate thereof, or an enantiomer thereof, or a diastereomer thereof, and the Boc protecting group reagent may be performed in the presence of an alcohol. In certain such embodiments, the alcohol is methanol.

In some embodiments, the compound of formula (3) can be used in the next reaction without substantial purification.

In some embodiments, the compound of formula (3), or a salt thereof, or a solvate thereof, or an enantiomer thereof, or a diastereomer thereof, may be a compound of formula (3a):

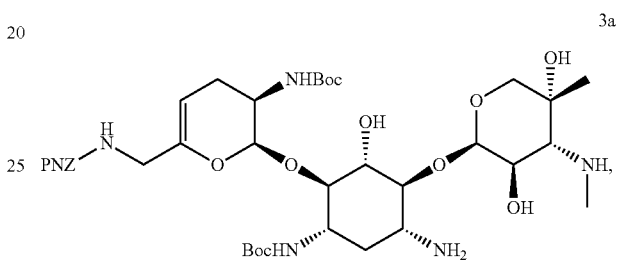

or a salt thereof, or a solvate thereof, synthesized by contacting the compound of formula (2b), or a salt thereof, or a solvate thereof, with a Boc protecting group reagent.

Synthesis of a Compound of Formula (4)

With continued reference to Scheme 2, a compound of formula (3), or a salt thereof, or a solvate thereof, or an enantiomer thereof, or a diastereomer thereof, may be contacted with

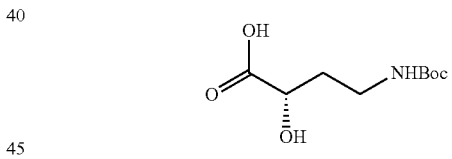

to yield a compound of formula (4):

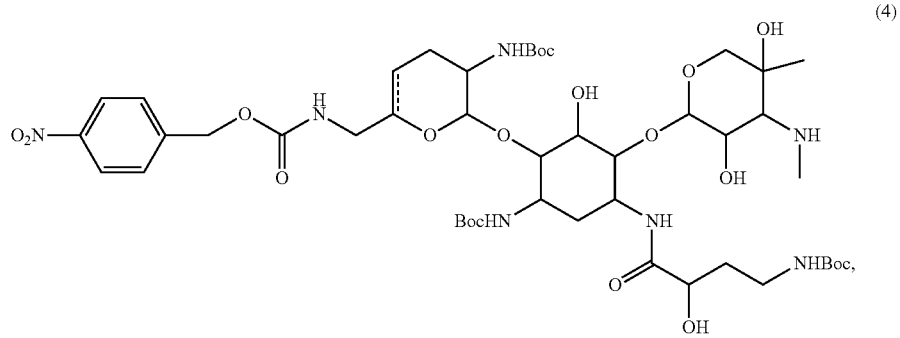

or a salt thereof, or a solvate thereof, or an enantiomer thereof, or a diastereomer thereof. In certain such embodiments, === is a double bond.

The reaction between the compound of formula (3), or a salt thereof, or a solvate thereof, or an enantiomer thereof, or a diastereomer thereof, and

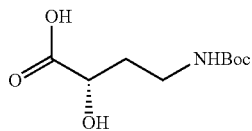 [SMILES: CC(C)(C)OC(=O)NCC[C@H](O)C(=O)O]

may be performed in the presence of an activating reagent and a peptide coupling reagent.

An activating reagent refers to a reagent that converts the carbonyl of a carboxylic acid group into one that is more susceptible to nucleophilic attack. In some embodiments, the activating reagent is HATU, HOOBt, HOSu, HOAt, DMAP, BOP, PyBOP, PyBrOP, PyAOP, PyOxim, DEPBT, TBTU, HBTU, HCTU, HDMC, COMU, CDI, or HOBt. In certain such embodiments, the activating reagent is HOBt. In some embodiments, the activating reagent is present in about 0.05 to 1.0 molar equivalents to

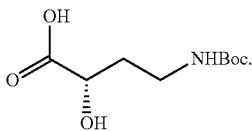 [SMILES: CC(C)(C)OC(=O)NCC[C@H](O)C(=O)O]

In some embodiments, the peptide coupling reagent is DCC, EDC, DIC, WSC, EDAC or PyBOP. In some embodiments, the peptide coupling reagent is EDAC or PyBOP. In certain such embodiments, the peptide coupling reagent is EDAC. In some embodiments, the peptide coupling reagent is present in about 1.0 to 1.4 molar equivalents to

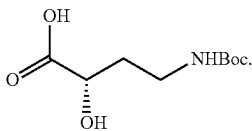 [SMILES: CC(C)(C)OC(=O)NCC[C@H](O)C(=O)O]

In some embodiments, the peptide coupling reagent is present in about 1.0; 1.1; 1.2; 1.3; or 1.4 molar equivalents to

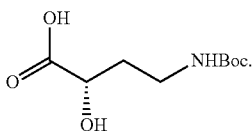 [SMILES: CC(C)(C)OC(=O)NCC[C@H](O)C(=O)O]

The reaction between the compound of formula (3), or a salt thereof, or a solvate thereof, or an enantiomer thereof, or a diastereomer thereof, and

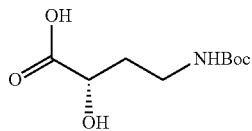 [SMILES: CC(C)(C)OC(=O)NCC[C@H](O)C(=O)O]

may be performed in an acidic condition. In certain such embodiments, the acidic condition is pH between around 4 and 7. In certain such embodiments, the acidic condition is pH around 5.

The reaction between the compound of formula (3), or a salt thereof, or a solvate thereof, or an enantiomer thereof, or a diastereomer thereof, and

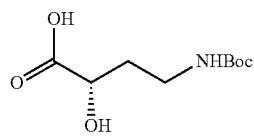 [SMILES: CC(C)(C)OC(=O)NCC[C@H](O)C(=O)O]

may be performed in the presence of an alcohol. In certain such embodiments, the alcohol is methanol.

The compound of formula (4), or a salt thereof, or a solvate thereof, or an enantiomer thereof, or a diastereomer thereof, may be a compound of formula (4a):

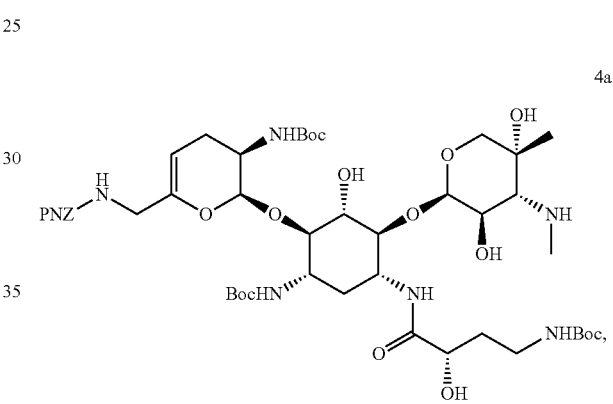

or a salt thereof, or a solvate thereof, synthesized by contacting the compound of formula (3a), or a salt thereof, or a solvate thereof, with

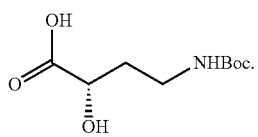 [SMILES: CC(C)(C)OC(=O)NCC[C@H](O)C(=O)O]

The disclosure further provides for a process comprising preparing a crystalline form of compound of formula (4), or a salt thereof, or a solvate thereof, or an enantiomer thereof, or a diastereomer thereof. The disclosure also provides for a process comprising isolating the compound of formula (4), or a salt thereof, or a solvate thereof, or an enantiomer thereof, or a diastereomer thereof, e.g., as described below in Example 1.

As noted herein, certain crystallization steps under particular conditions may aid in purification by purging impurities. And, once crystallization conditions are established, the use of crystallization as one means of purification can lead to both good yields and lower batch-to-batch variability in impurities compared to prior methods of purification Scheme 3: Synthesis of a Compound of Formula (6)

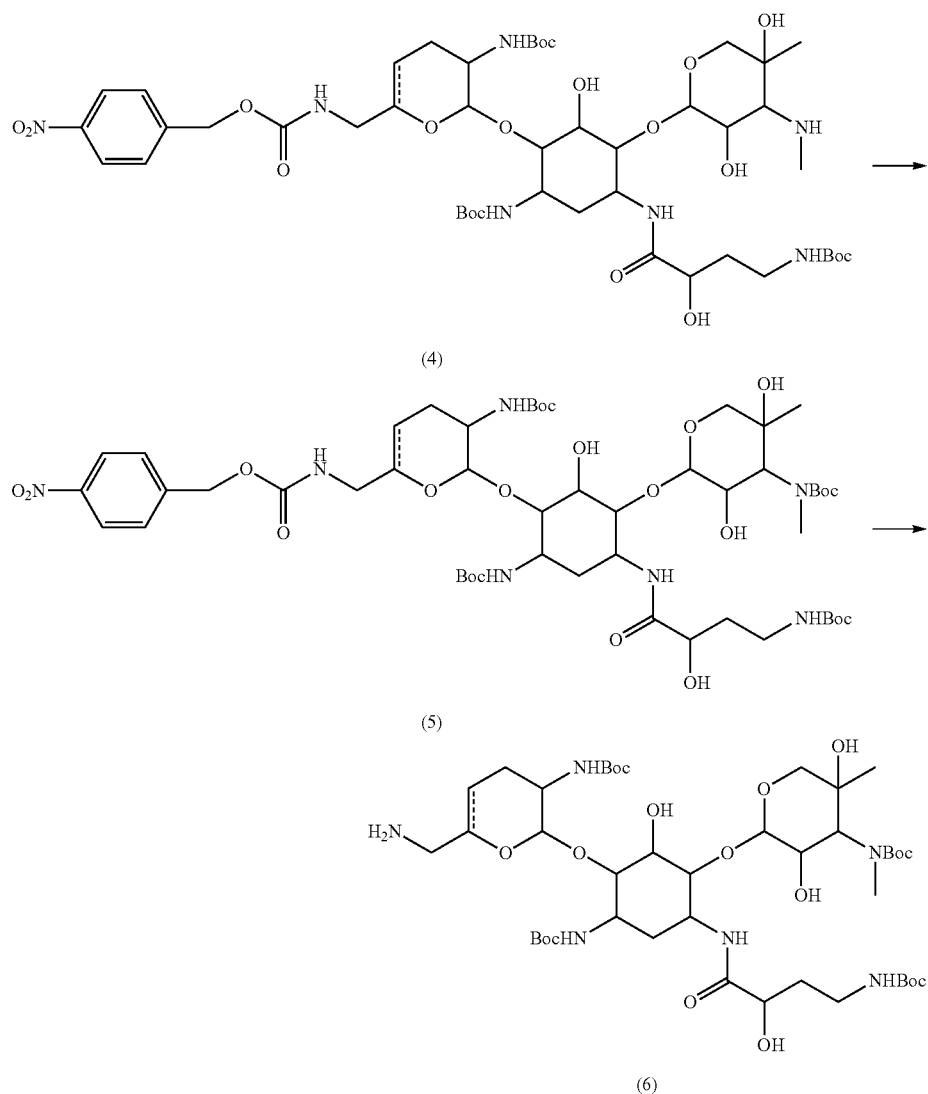

Scheme 3 shows the synthesis of a compound of formula (6), or a salt thereof, or a solvate thereof, or an enantiomer thereof, or a diastereomer thereof. === is a single bond or a double bond.

Synthesis of a Compound of Formula (5)

With continued reference to Scheme 3, a compound of formula (4), or a salt thereof, or a solvate thereof, or an enantiomer thereof, or a diastereomer thereof, may be contacted with a Boc protecting group reagent to yield a compound of formula (5), or a salt thereof, or a solvate thereof, or an enantiomer thereof, or a diastereomer thereof. In certain such embodiments, === is a double bond.

A standard Boc protecting group reagent may be used for this transformation, including, but not limited to N-tert-butoxycarbonylimidazole, 2-(tert-butoxycarbonyloxy-imino)-2-phenylacetonitrile, 2-(tert-butoxycarbonylthio)-4,6-dimethylpyrimidine, 1-tert-butoxycarbonyl-1,2,4-triazole, tert-butyl phenyl carbonate, N-(tert-butoxycarbonyloxy)phthalimide, tert-butyl 2,4,5-trichlorophenyl carbonate, $Boc_2O$, and Boc-ONb. In some embodiments, the Boc protecting group reagent is $Boc_2O$.

In some embodiments, the reaction between the compound of formula (4), or a salt thereof, or a solvate thereof, or an enantiomer thereof, or a diastereomer thereof, and a Boc protecting group reagent may be performed at a temperature of up to about 60° C. In some embodiments, the reaction between the compound of formula (4), or a salt thereof, or a solvate thereof, or an enantiomer thereof, or a diastereomer thereof, and a Boc protecting group reagent may be performed in the presence of an alcohol. In certain such embodiments, the alcohol is methanol or ethanol. In certain such embodiments, the alcohol is methanol. The use of an alcohol in the reaction between the compound of formula (4), or a salt thereof, or a solvate thereof, or an enantiomer thereof, or a diastereomer thereof, and a Boc protecting group reagent may assist in telescoping with the next reaction.

In some embodiments, the compound of formula (5) can be used in the next reaction without substantial purification.

The compound of formula (5), or a salt thereof, or a solvate thereof, or an enantiomer thereof, or a diastereomer thereof, may be a compound of formula (5a):

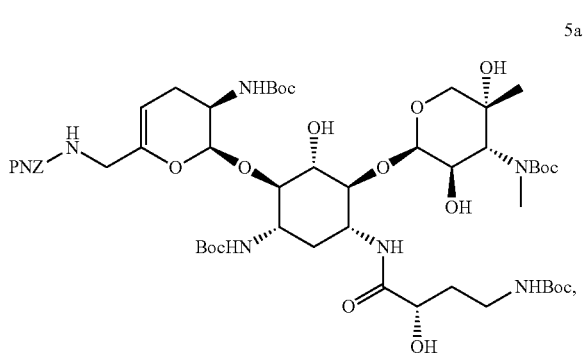

(5a)

or a salt thereof, or a solvate thereof, synthesized by contacting the compound of formula (4a), or a salt thereof, or a solvate thereof, with a Boc protecting group reagent.

Synthesis of a Compound of Formula (6)

With continued reference to Scheme 3, a compound of formula (5), or a salt thereof, or a solvate thereof, or an enantiomer thereof, or a diastereomer thereof, may be contacted with a PNZ deprotecting reagent to yield a compound of formula (6), or a salt thereof, or a solvate thereof, or an enantiomer thereof, or a diastereomer thereof. In certain such embodiments, === is a double bond.

In some embodiments, the PNZ deprotecting reagent is sodium dithionite. In other embodiments, the PNZ deprotection reaction may be hydrogenation with $H_2$ and a catalyst, such as Pd/C or $PtO_2$. Sodium dithionite may be advantageous over deprotection reactions requiring hydrogenation as it may be easier to use on a larger scale, may be chemoselective and less hazardous, and may not require special equipment to use.

The compound of formula (6), or a salt thereof, or a solvate thereof, or an enantiomer thereof, or a diastereomer thereof, may be a compound of formula (6a):

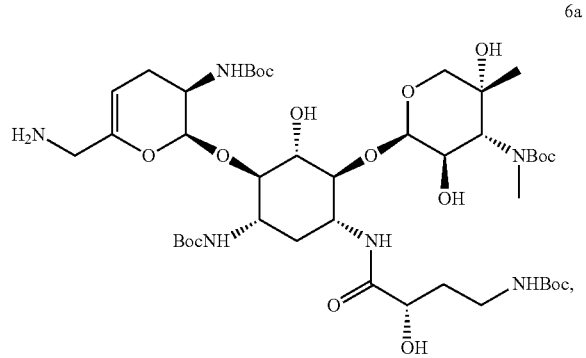 [SMILES: CN(C(=O)OC(C)(C)C)[C@@H]1[C@@H](O)[C@@H](O[C@@H]2[C@@H](O)[C@H](O[C@H]3OC(CN)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

(6a)

or a salt thereof, or a solvate thereof, synthesized by contacting the compound of formula (5a), or a salt thereof, or a solvate thereof, with a PNZ deprotecting reagent.

The disclosure further provides for a process for preparing a crystalline form of compound of formula (6), or a salt thereof, or a solvate thereof, or an enantiomer thereof, or a diastereomer thereof. The disclosure also provides for a process comprising isolating the compound of formula (6), or a salt thereof, or a solvate thereof, or an enantiomer thereof, or a diastereomer thereof, e.g., as described below in Example 2.

Thus, as noted previously, this crystallization may aid in the purification process (e.g., lowering impurities) and simplify the purification process compared to prior methods of purification, thereby potentially leading to greater reproducibility for the process overall.

Scheme 4: Synthesis of a Compound of Formula (7)

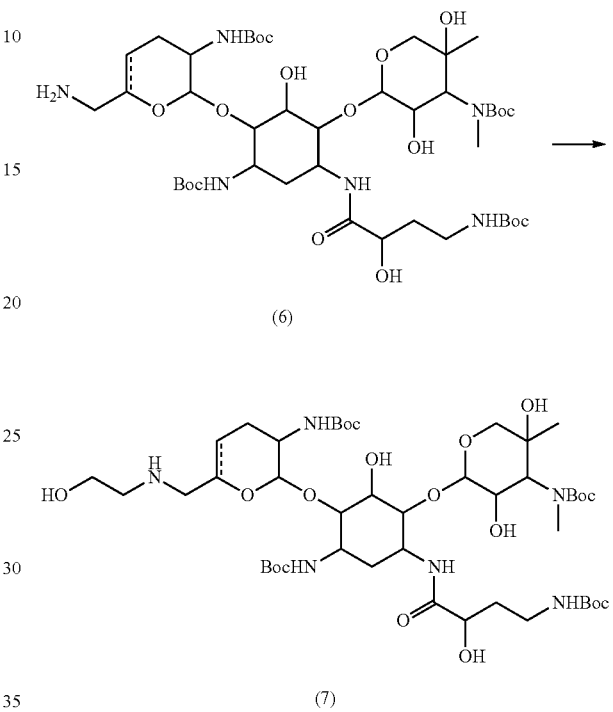

Scheme 4 shows the synthesis of a compound of formula (7), or a salt thereof, or a solvate thereof, or an enantiomer thereof, or a diastereomer thereof. === is a single bond or a double bond. In some embodiments, === is a double bond.

The reaction from compound of formula (6) to compound of formula (7) is surprising with regard to the alkylation. Under normal circumstances, a primary amine, such as the group on compound of formula (6), has a tendency to alkylate more than once. Thus, it is surprising that the compound of formula (7) comprises a secondary amine (e.g., alkylated once with —$CH_2CH_2OH$). As discussed below, the reaction conditions, including solvent choice and use of a reagent to prevent over-alkylation, can provide monoalkylation at the appropriate site.

Synthesis of a Compound of Formula (7)

With continued reference to Scheme 4, a compound of formula (6), or a salt thereof, or a solvate thereof, or an enantiomer thereof, or a diastereomer thereof, may be contacted with

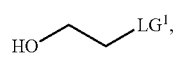

wherein $LG^1$ is a leaving group, to yield a compound of formula (7), or a salt thereof, or a solvate thereof, or an enantiomer thereof, or a diastereomer thereof. In certain such embodiments, the leaving group is iodo, bromo, or chloro. In certain such embodiments, the leaving group is iodo. In some embodiments, the

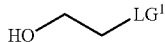

is present in about 1.0 to 1.5 molar equivalents to the compound of formula (6).

The reaction between the compound of formula (6), or a salt thereof, or a solvate thereof, or an enantiomer thereof, or a diastereomer thereof, and

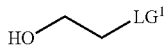

may be performed in conditions substantially free of water. In some embodiments, the reaction between the compound of formula (6), or a salt thereof, or a solvate thereof, or an enantiomer thereof, or a diastereomer thereof, and

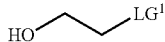

may be performed in the presence of a solvent selected from the group consisting of acetonitrile, acetone, and combination thereof. Acetone may aid in the selectivity of the reaction, promoting mono-alkylation. Acetonitrile may be used to remove water by azeotrope.

In some embodiments, the reaction between the compound of formula (6), or a salt thereof, or a solvate thereof, or an enantiomer thereof, or a diastereomer thereof, and

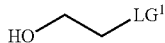

may be performed in the presence of NaHCO$_3$, lithium carbonate, sodium carbonate, potassium carbonate, cesium carbonate, sodium sulfate, DIPEA, sodium phosphate, trimethyl orthoformate, and hexamethyldisilane. In certain such embodiments, the reaction is performed in the presence of NaHCO$_3$. In some embodiments, the reaction between the compound of formula (6), or a salt thereof, or a solvate thereof, or an enantiomer thereof, or a diastereomer thereof, and

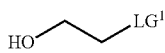

may be performed at a temperature of about 30° C. to 40° C. In certain such embodiments, the temperature is about 35° C. Temperatures higher than 50° C. may lead to the formation of a dialkylated by-product.

The reaction between the compound of formula (6), or a salt thereof, or a solvate thereof, or an enantiomer thereof, or a diastereomer thereof, and

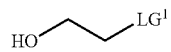

may be quenched by adding 1,4-diazabicyclo[2.2.2]octane (DABCO) to the reaction mixture. DABCO may be used for substantially stopping the reaction and preventing over-alkylation. Alternatively, the reaction between the compound of formula (6), or a salt thereof, or a solvate thereof, or an enantiomer thereof, or a diastereomer thereof, and

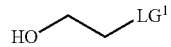

may also be quenched by adding 1-propylamine, piperidine, diethylamine, N-ethyldimethylamine, triethylamine, DBU, MeOH, carbonate buffer, dimethylamine, cysteine, diethanolamine, or NaOH.

In some embodiments, the compound of formula (7), or a salt thereof, or a solvate thereof, or an enantiomer thereof, or a diastereomer thereof, may be a compound of formula (7a):

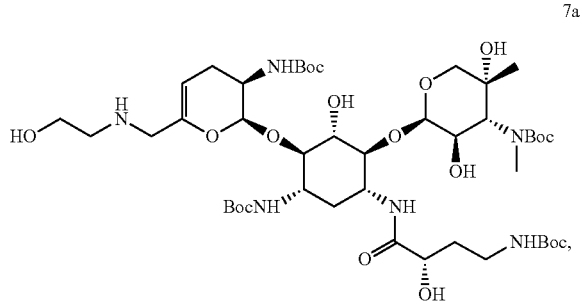 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

7a or a salt thereof, or a solvate thereof, synthesized by contacting the compound of formula (6a), or a salt thereof, or a solvate thereof, with

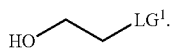

The disclosure further provides for a process for preparing a crystalline form of compound of formula (7), or a salt thereof, or a solvate thereof, or an enantiomer thereof, or a diastereomer thereof. The disclosure also provides a process comprising isolating the compound of formula (7), or a salt thereof, or a solvate thereof, or an enantiomer thereof, or a diastereomer thereof, e.g., as described below in Example 3.

This crystallization may aid in the purification process (e.g., lowering impurities) and simplifies purification compared to prior methods of purification. Crystallization may also act to purge of impurities.

Scheme 5: Synthesis of a Compound of Formula (9)

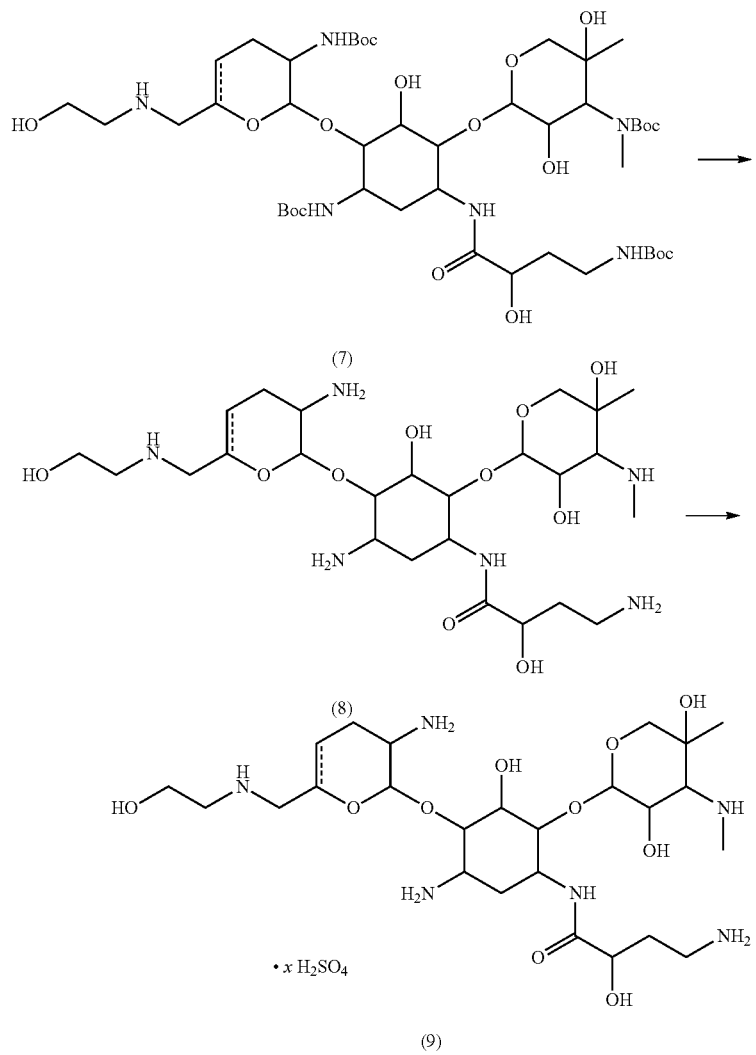

Scheme 5 shows the synthesis of a compound of formula (9), or a salt thereof, or a solvate thereof, or an enantiomer thereof, or a diastereomer thereof. ═══ is a single bond or a double bond and x is 1 to 5. In some embodiments, ═══ is a double bond. In some embodiments, x is 2 to 3.

Synthesis of a Compound of Formula (8)

With continued reference to Scheme 5, a compound of formula (7), or a salt thereof, or a solvate thereof, or an enantiomer thereof, or a diastereomer thereof, may be contacted with a Boc removing reagent to yield a compound of formula (8), or a salt thereof, or a solvate thereof, or an enantiomer thereof, or a diastereomer thereof. In some embodiments, the Boc removing reagent is TFA, MsOH (methanesulfonic acid or $CH_3SO_3H$), PTSA (p-toluenesulfonic acid or tosylic acid), $H_2SO_4$, or HCl. In some embodiments, the Boc removing reagent is TFA or MsOH. In some embodiments, the Boc removing reagent is TFA, $H_2SO_4$, or HCl.

In some embodiments, the Boc removing reagent is TFA, thereby yielding a TFA salt of compound of formula (8), or a solvate thereof, or an enantiomer thereof, or a diastereomer thereof. As the deprotection reaction needs to be anhydrous, TFA is typically used for this transformation.

The step of removing the Boc group can result in hydrolysis of the substrate and the presence of compound (IMP-1) immediately after the reaction (e.g., before any purification).

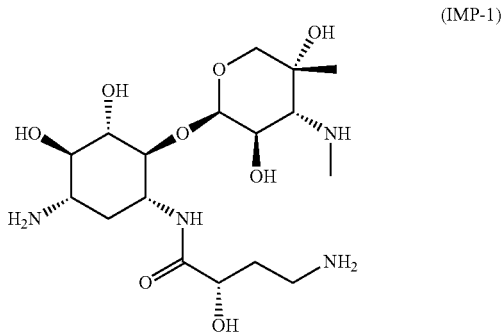 [SMILES: CN[C@@H]1[C@@H](O)[C@@H](O[C@@H]2[C@@H](O)[C@H](O)[C@@H](N)C[C@H]2NC(=O)[C@@H](O)CCN)OC[C@]1(C)O]

(IMP-1)

In certain embodiments, the step of removing the Boc group does not result in substantial hydrolysis and the presence of compound (IMP-1) immediately after the reaction (e.g., before any purification) is minimized. In certain embodiments, the presence or amount of compound (IMP-1) can be determined by HPLC. In certain embodiments, the compound IMP-1 can be present in an amount of 0 to 7%, such as about 0, 0.2, 0.4, 0.6, 0.8, 1, 1.5, 2, 2.5, 3, 3.5, 4, 4.5, 5, 5.5, 6, 6.5, or 7%, immediately after the reaction (e.g., before any purification). When the amount of IMP-1 is 0%, this amount indicates that the specified impurity can be present at levels below the level of detection of typical analytical methods known and routinely used by persons of skill in the art (e.g., HPLC).

In certain embodiments, the acid is TFA or MsOH and the amount of the compound IMP-1 can be about 0 to 7% immediately after the reaction (e.g., before any purification). In some instances, the acid is TFA or MsOH and the amount of the compound IMP-1 can be about 0 to 2.5% immediately after the reaction (e.g., before any purification). In some instances, the acid is TFA and the amount of the compound IMP-1 can be about 0 to 2.5%, such as about 0, 0.2, 0.4, 0.6, 0.8, 1, 1.5, 2, or 2.5%, immediately after the reaction (e.g., before any purification). In some instances, the acid is MsOH and the amount of the compound IMP-1 can be about 0.2 to 2.5%, such as about 0.2, 0.4, 0.6, 0.8, 1, 1.5, 2, or 2.5%, immediately after the reaction (e.g., before any purification).

In some instances, the acid is HCl and the amount of the compound IMP-1 can be about 0 to 1%, such as about 0, 0.2, 0.4, 0.6, 0.8, or 1%, immediately after the reaction (e.g., before any purification).

In some instances, the acid is $H_2SO_4$, and the amount of the compound IMP-1 can be about 0 to 7%, such as about 0, 0.2, 0.4, 0.6, 0.8, 1, 1.5, 2, 2.5, 3, 3.5, 4, 4.5, 5, 5.5, 6, 6.5, or 7%, immediately after the reaction (e.g., before any purification).

When a compound of formula (7), or a salt thereof, or a solvate thereof, or an enantiomer thereof, or a diastereomer thereof, is contacted with various Boc removing reagents, the amounts of IMP-1 can vary, depending on the identity of the Boc removing reagent. The table below shows the amount of IMP-1 from reaction of compound of formula (7), or a salt thereof, or a solvate thereof, or an enantiomer thereof, or a diastereomer thereof, with various Boc removing reagents.

|  | HCl | TFA | MsOH | $H_2SO_4$ |
|---|---|---|---|---|
| Amount of IMP-1 | 0% 0.81% | 0% 0.80% | 0% 2.50% | 0% 4.61% 6.61% 3.80% 5.52% 0.74% (from various reaction conditions) |

In some embodiments, the compound of formula (8) can be used in the next reaction without substantial purification.

In some embodiments, the compound of formula (8), or a salt thereof, or a solvate thereof, or an enantiomer thereof, or a diastereomer thereof, may be a compound of formula (8a):

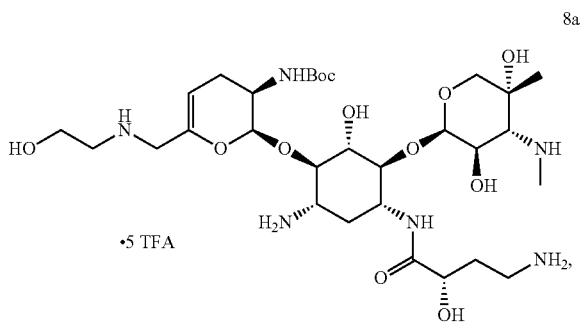 [SMILES: CN[C@@H]1[C@@H](O)[C@@H](O[C@@H]2[C@@H](O)[C@H](O[C@H]3OC(CNCCO)=CC[C@H]3NC(=O)OC(C)(C)C)[C@@H](N)C[C@H]2NC(=O)[C@@H](O)CCN)OC[C@]1(C)O]

or a solvate thereof, synthesized by contacting the compound of formula (7a), or a salt thereof, or a solvate thereof, with a Boc removing reagent.

Synthesis of a Compound of Formula (9)

Salt formation with an acid may be performed to yield a salt of a compound of formula (8), or a solvate thereof, or an enantiomer thereof, or a diastereomer thereof. If the compound of formula (8) is already a salt, such as a TFA salt, the salt may be removed to afford a compound of formula (8), or a solvate thereof, or an enantiomer thereof, or a diastereomer thereof prior to formation of a different salt.

In some embodiments, the acid in the salt formation step is sulfuric acid, thereby yielding a sulfate salt of a compound of formula (9),

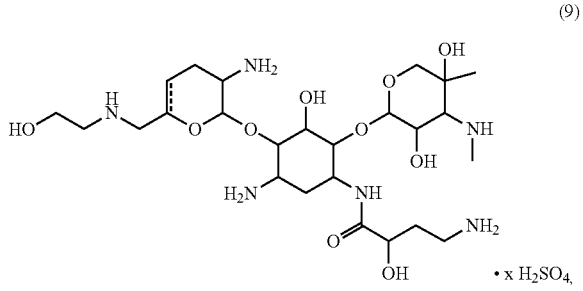

or a solvate thereof, or an enantiomer thereof, or a diastereomer thereof, wherein x is 1 to 5. In some embodiments, x is 2 to 3. The sulfate salt of a compound of formula (9) may have improved stability compared to other salts. In some embodiments, the compound of formula (9), or a salt thereof, or a solvate thereof, or an enantiomer thereof, or a diastereomer thereof, may be plazomicin sulfate:

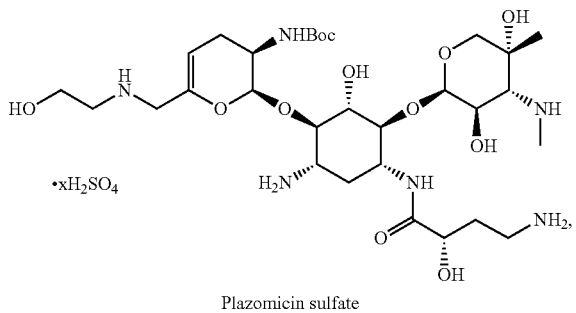 [SMILES: CN[C@@H]1[C@@H](O)[C@@H](O[C@@H]2[C@@H](O)[C@H](O[C@H]3OC(CNCCO)=CC[C@H]3NC(=O)OC(C)(C)C)[C@@H](N)C[C@H]2NC(=O)[C@@H](O)CCN)OC[C@]1(C)O]

Plazomicin sulfate or a solvate thereof, synthesized by doing a salt formation with the compound of formula (8a), or a salt thereof, or a solvate thereof, wherein x is 1 to 5. In some embodiments, x is 2 to 3.

Crystalline Compounds and Preparation and Characterization Thereof:

In an aspect, the disclosure relates to intermediates in a synthetic process that may be used to synthesize the compound of formula (9), or a salt thereof, or a solvate thereof, or an enantiomer thereof, or a diastereomer thereof. These intermediates may be in a crystalline form. The disclosure provides for methods of making crystalline intermediates in the synthetic process that may be used to synthesize the compound of formula (9), or a salt thereof, or a solvate thereof, or an enantiomer thereof, or a diastereomer thereof. The crystalline intermediates of the disclosure may be characterized by x-ray powder diffraction (XRPD), differential scanning calorimetry (DSC), and thermogravimetric analysis (TGA). Methods of collecting XRPD, DSC, and TGA data and the properties of the crystalline intermediates of the disclosure are further illustrated in the Examples below.

Compounds 4 and 4a

In some embodiments, the intermediate in the synthesis of a compound of formula (9), or a salt thereof, or a solvate thereof, or an enantiomer thereof, or a diastereomer thereof, is a compound of formula (4):

tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl) carbamate, or a solvate thereof.

In some embodiments, crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, or a solvate thereof, is characterized by the XRPD pattern in which the peak positions are substantially in accordance with those shown in FIG. 1.

Figure 2:
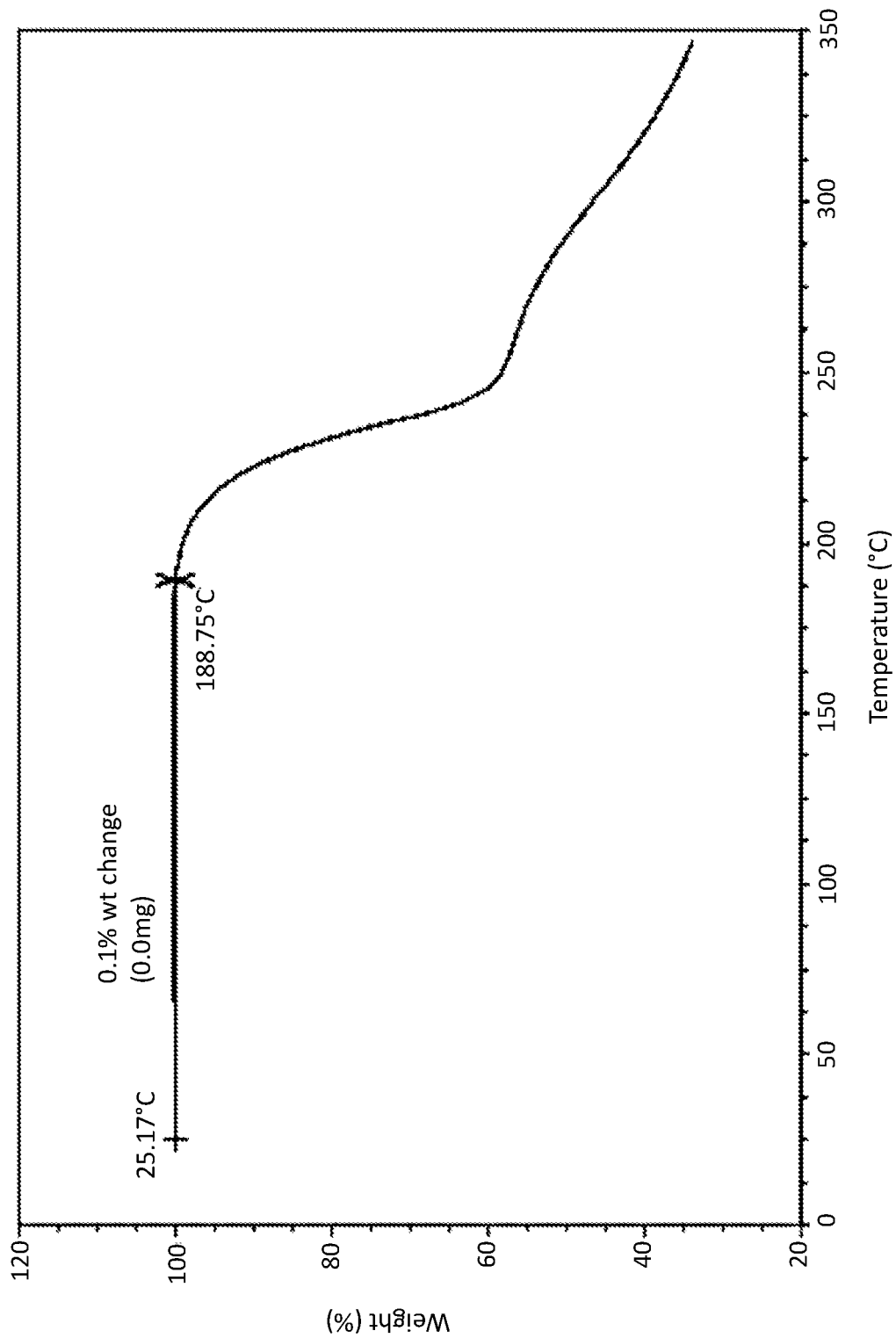

In some embodiments, crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, or a solvate thereof, is characterized by the TGA trace shown in FIG. 2. In some embodiments, crystalline tert-butyl ((2S,3R)-2-(((1R,2S,3S,4R,6S)-6-((tert-butoxycarbonyl)amino)-4-((S)-4-((tert-bu-

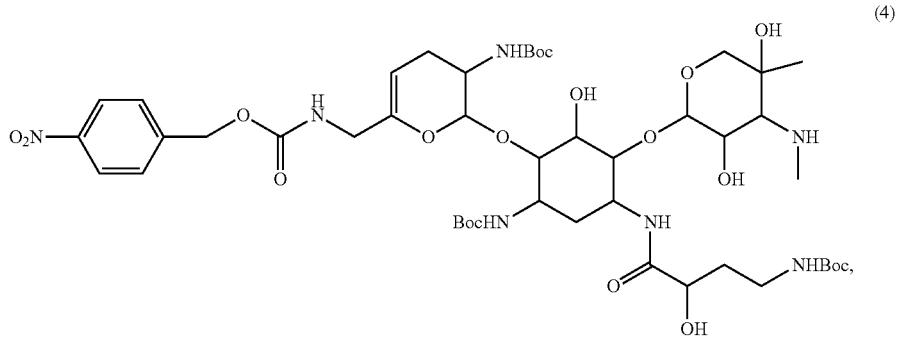

(4)

or a salt thereof, or a solvate thereof, or an enantiomer thereof, or a diastereomer thereof. In certain such embodiments, the compound of formula (4) is of the following formula:

toxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-

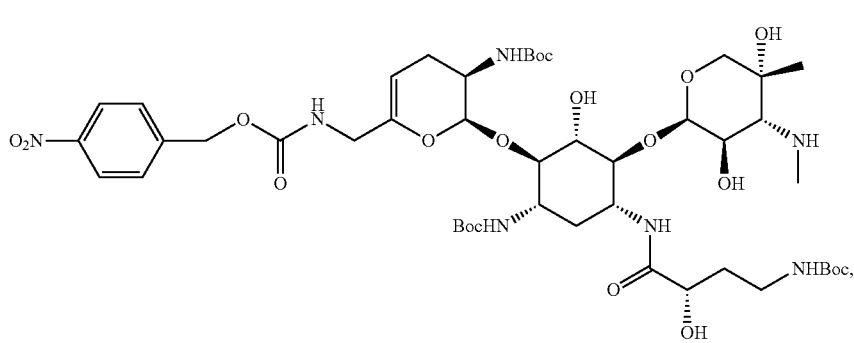

(4a)

or a salt thereof, or a solvate thereof. In certain such embodiments, the compound of formula (4a) is crystalline dihydro-2H-pyran-3-yl)carbamate, or a solvate thereof, is characterized by the DSC profile in FIG. 3.

The disclosure provides a process for preparing crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, Formula (4a), or a solvate thereof, comprising:
(a) treating Formula (4a), or a salt thereof, or a solvate thereof, with acetonitrile to produce a solution;
(b) heating the solution from step (a);
(c) adding water to the heated solution of step (b);
(d) cooling the solution from step (c);
(e) charging the solution from step (d) with a seed crystal; and
(f) isolating the resulting solids to yield crystalline Formula (4a), or a solvate thereof.

In some embodiments of the process for preparing crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, acetonitrile with 1.5% deionized (DI) water at 75±3° C. with seeding followed by cooling may be used for crystallization. Additionally, the crystallization may be performed at 65±3° C. or 70±3° C. followed by cooling. In some embodiments, 1-propanol, with or without deionized (DI) water, may be used instead of acetonitrile for crystallization of tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate. Crystallization conditions screened are summarized in Example 1 and Table 5.

Compound 6a

In some embodiments, the intermediate in the synthesis of a compound of formula (9), or a salt thereof, or a solvate thereof, or an enantiomer thereof, or a diastereomer thereof, is a compound of formula (6a):

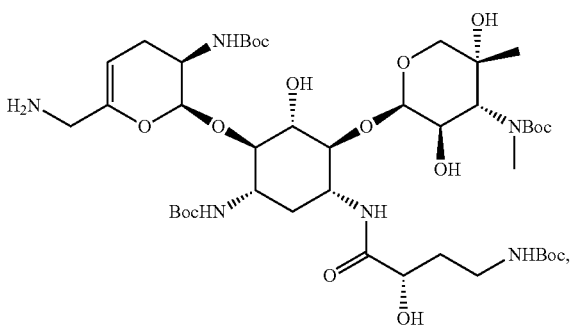

6a or a salt thereof, or a solvate thereof. In certain such embodiments, the disclosure provides for crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof.

Figure 4:
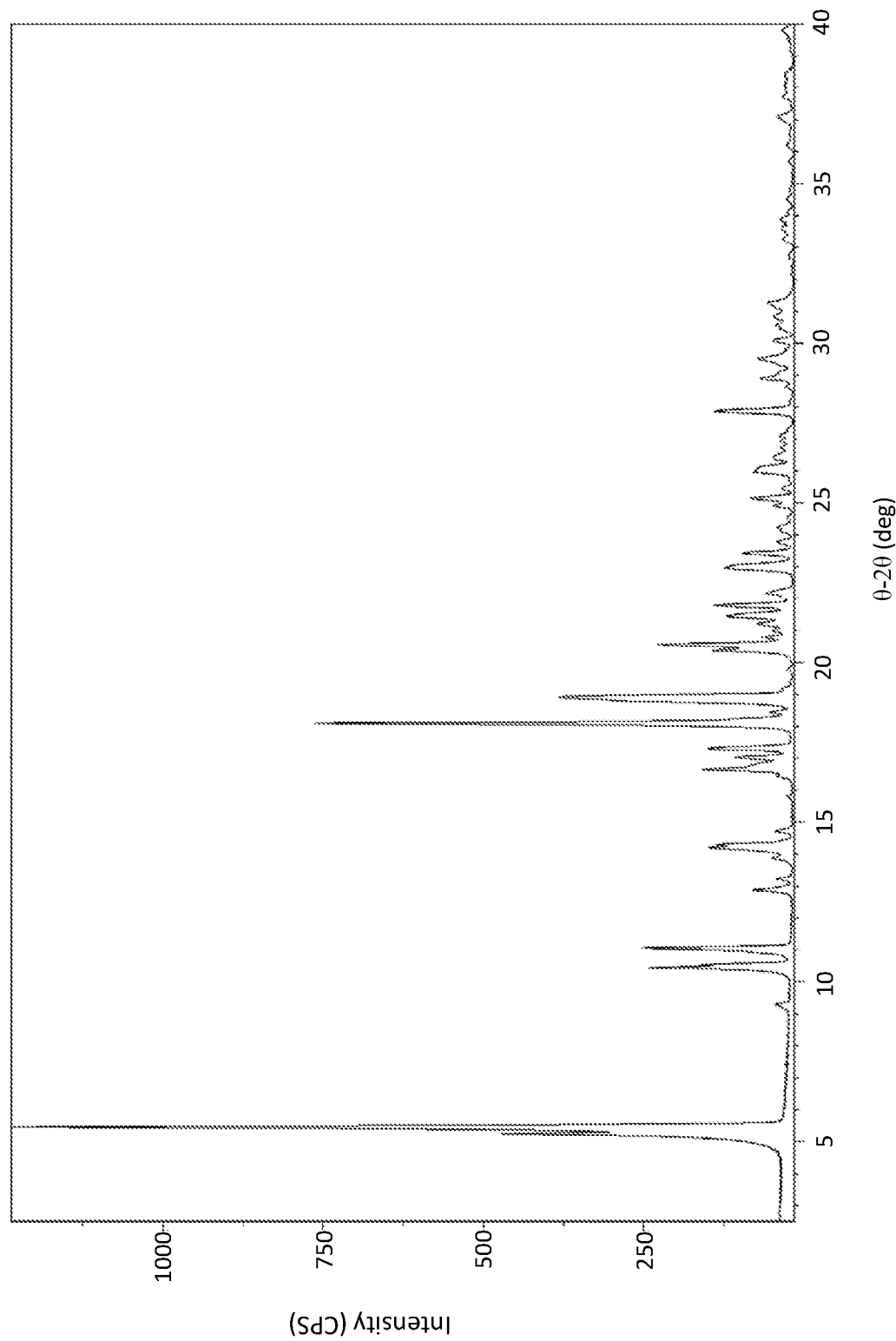

In some embodiments, crystalline tert-butyl((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, or a solvate thereof, is characterized by the XRPD pattern in which the peak positions are substantially in accordance with those shown in FIG. 4 and Table 1. In some embodiments, there is a variability of about ±0.2 °2θ to diffraction angles in XRPD patterns, for example as depicted in Table 1.

TABLE 1

XRPD Data for Crystalline Compound of Formula (6a)

| 2-Theta |
|---------|
| 5.37 |
| 6.10 |
| 10.66 |
| 12.17 |
| 13.08 |
| 14.00 |
| 15.00 |
| 16.65 |
| 17.65 |
| 18.31 |
| 18.55 |
| 20.06 |
| 20.61 |
| 21.41 |
| 22.99 |
| 24.21 |

In certain embodiments, crystalline tert-butyl((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, or a solvate thereof, is characterized by one or more 2θ values at about 6.10, 10.66, 12.17, 17.65; and 18.55 degrees in X-ray powder diffraction, where there is a variability of about ±0.2 °2θ to diffraction angles in XRPD patterns.

Figure 5:
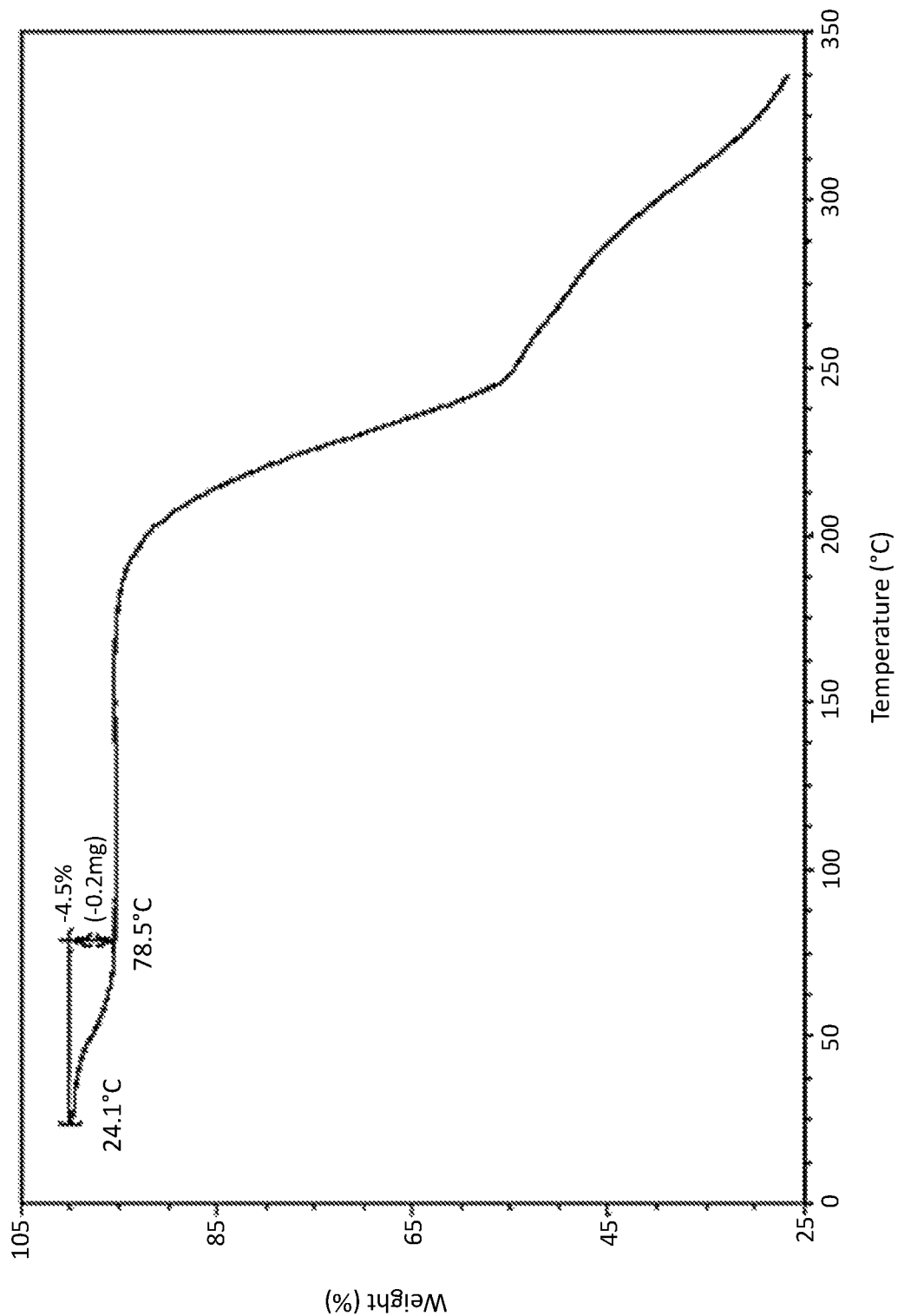
Figure 6:
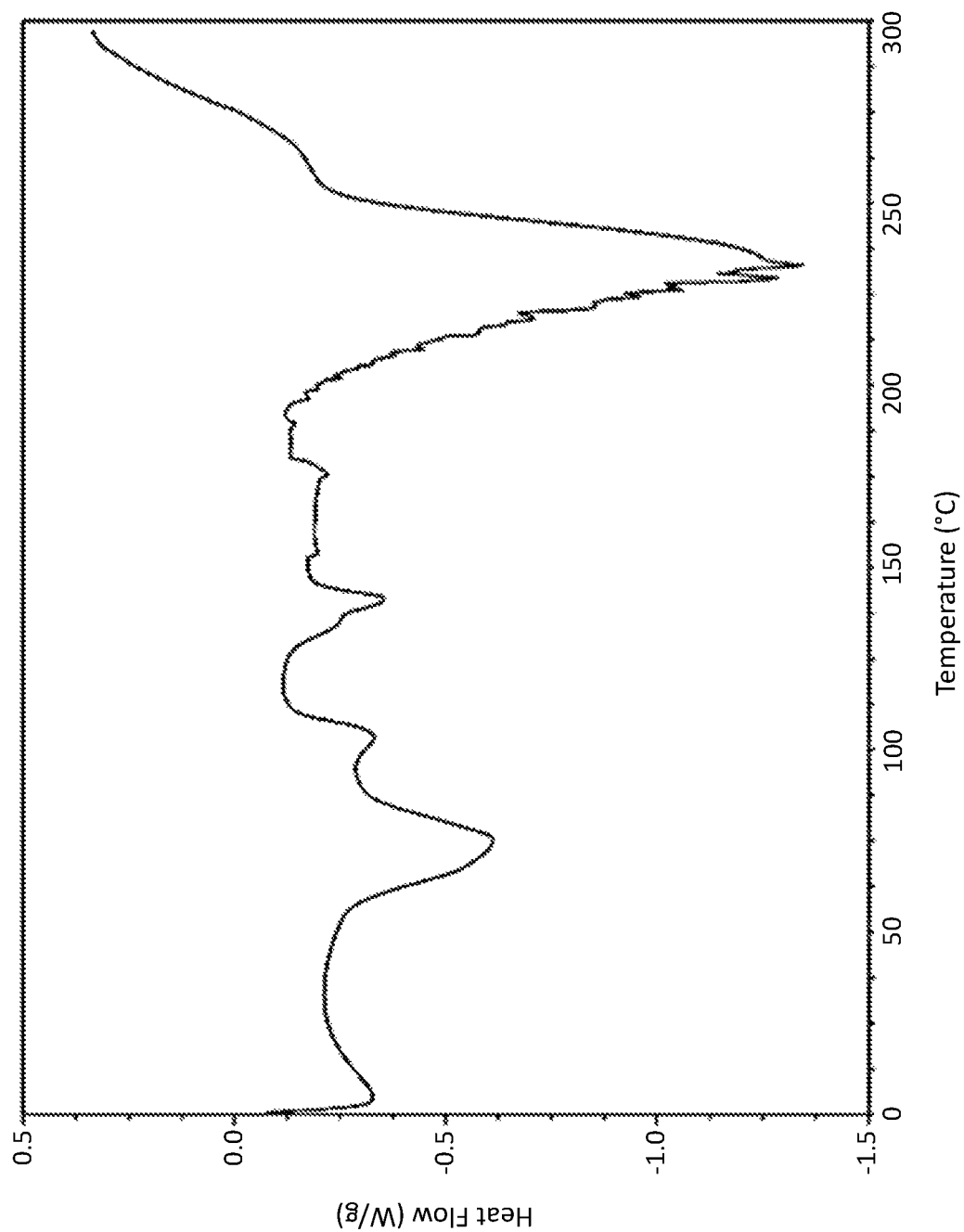

In some embodiments, crystalline tert-butyl((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, or a solvate thereof, is characterized by the TGA trace shown in FIG. 5. The main exothermic event in the DSC of crystalline tert-butyl((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, or a solvate thereof, occurred with a left limit temperature of 231.8° C. and energy of −52.9 kJ/kg (FIG. 6).

The disclosure provides a process for preparing crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof, comprising:
(a) treating Formula (6), or a salt thereof, or a solvate thereof, with isopropyl acetate (IPAc) to produce a solution;
(b) adding water to the solution of step (a) to produce a mixture;
(c) adding dichloromethane to the mixture from step (b) to produce a mixture;
(d) charging the mixture from step (c) with a seed crystal;
(e) isolating the resulting solids to yield crystalline Formula (6a), or a solvate thereof.

In some embodiments, step (d) is performed at a low temperature. In some embodiments, step (d) is performed at about 15-25° C., such as about 15-20° C. or about 20-25° C.

In some embodiments of the process for preparing crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, dichloromethane/isopropyl acetate (50/50 v/v) with 1% water, isopropyl acetate/dichloromethane (71/29 v/v) with 2% water, or isopropyl acetate/dichloromethane (71/29 v/v) with 8% water may be used. In certain such embodiments, dichloromethane/isopropyl acetate (50/50 v/v) with 1% water may be used. Isopropyl acetate is not required for the crystallization, but may be present as an extraction solvent. Filtration may be easier when isolating solids from dichloromethane/isopropyl acetate (50/50 v/v) with 1% water as sticky solids and some deliquescence were observed from solids isolated from isopropyl acetate/dichloromethane (71/29 v/v) with both 2% and 8% water. Further, the material isolated from dichloromethane/isopropyl acetate (50/50 v/v) with 1% water was crystalline. However, the material isolated from isopropyl acetate/dichloromethane (71/29 v/v) with 2% water was disordered, and the material isolated from isopropyl acetate/dichloromethane (71/29 v/v) with 8% water may contain a small amount of x-ray amorphous material. Crystallization conditions screened are summarized in Example 2.

Compounds 7 and 7a

In some embodiments, the intermediate in the synthesis of a compound of formula (9), or a salt thereof, or a solvate thereof, or an enantiomer thereof, or a diastereomer thereof is a compound of formula (7):

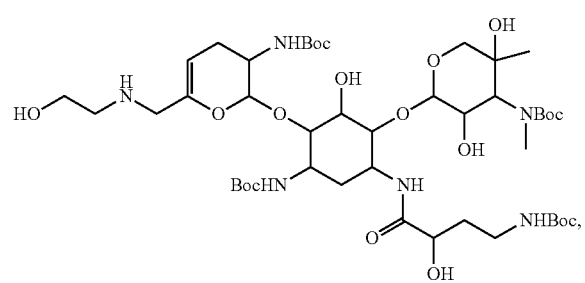

or a salt thereof, or solvate thereof, or an enantiomer thereof, or a diastereomer thereof. In certain such embodiments, the compound of formula (7) is of the following formula:

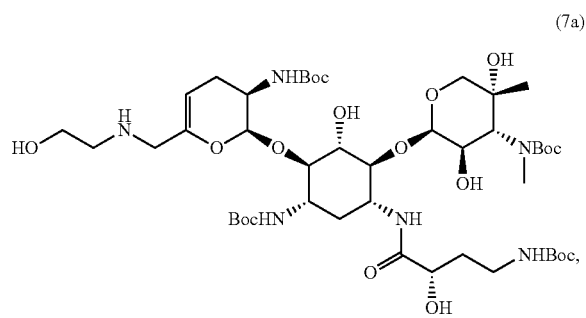 [SMILES: CN(C(=O)OC(C)(C)C)[C@@H]1[C@@H](O)[C@@H](O[C@@H]2[C@@H](O)[C@H](O[C@H]3OC(CNCCO)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

(7a)

or a salt thereof, or a solvate thereof. In certain such embodiments, the compound of formula (7a) is crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, or a solvate thereof.

Figure 7:
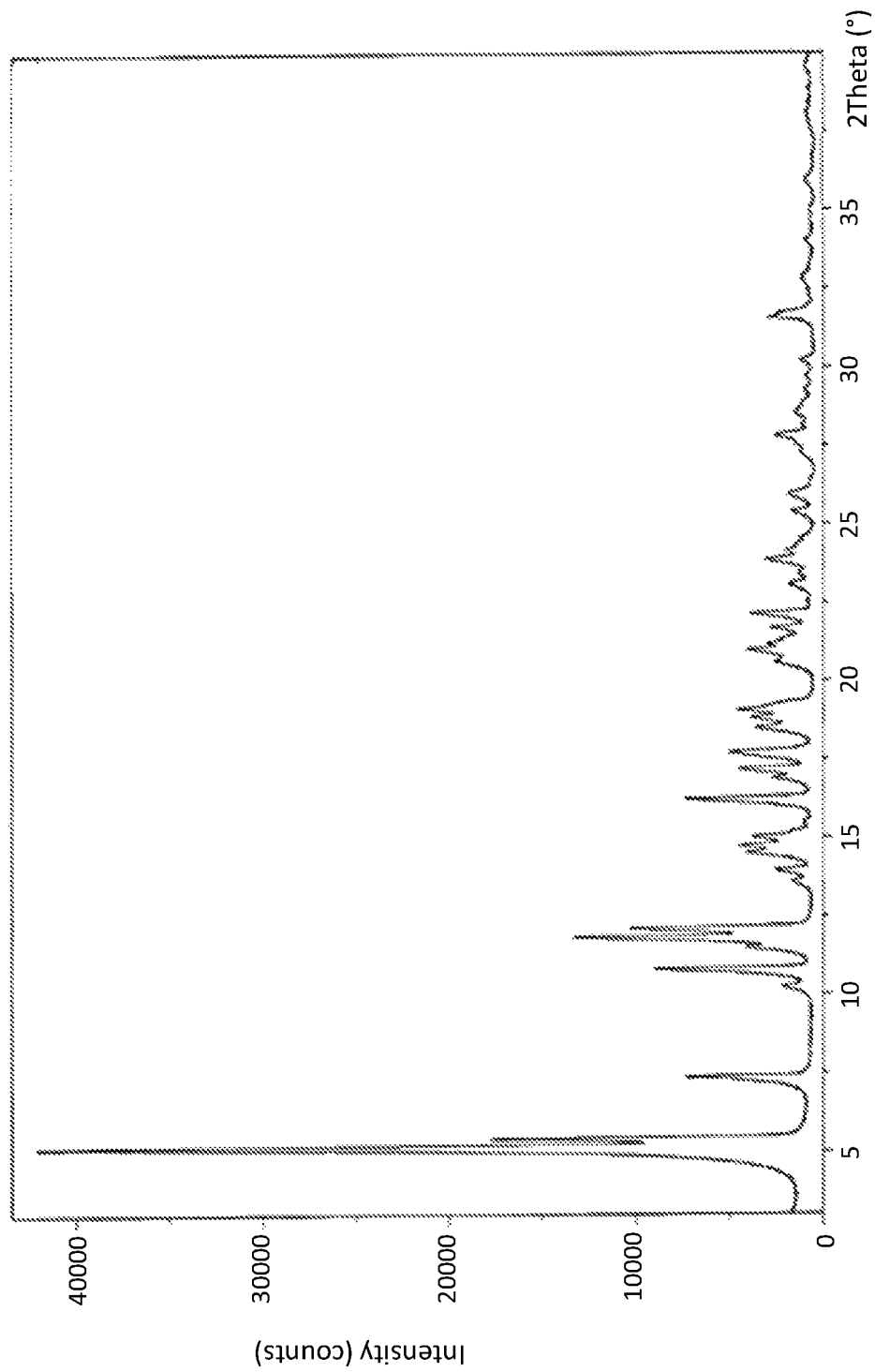

In some embodiments, crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, or a solvate thereof, is characterized by the XRPD pattern in which the peak positions are substantially in accordance with those shown in FIG. 7 and Table 2. In some embodiments, there is a variability of about ±0.2 °2θ to diffraction angles in XRPD patterns, for example as depicted in Table 2.

TABLE 2

| XRPD Data for Crystalline Compound of Formula (7a) |
|---|
| 2-Theta |
| 5.17 |
| 5.45 |
| 7.39 |
| 10.28 |
| 10.85 |
| 11.87 |
| 12.17 |
| 13.58 |
| 13.97 |
| 14.76 |
| 16.28 |
| 17.22 |

TABLE 2-continued

XRPD Data for
Crystalline
Compound
of Formula (7a)

2-Theta 17.79
18.51
19.08
20.58
20.98
21.75
22.18
23.02
23.91
25.90
27.85
31.75
36.00
37.78

In certain embodiments, crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, or a solvate thereof, is characterized by one or more 2θ values at about 5.17, 7.39, 10.85, and 12.17 degrees in X-ray powder diffraction, where there is a variability of about ±0.2 °2θ to diffraction angles in XRPD patterns.

Figure 8:
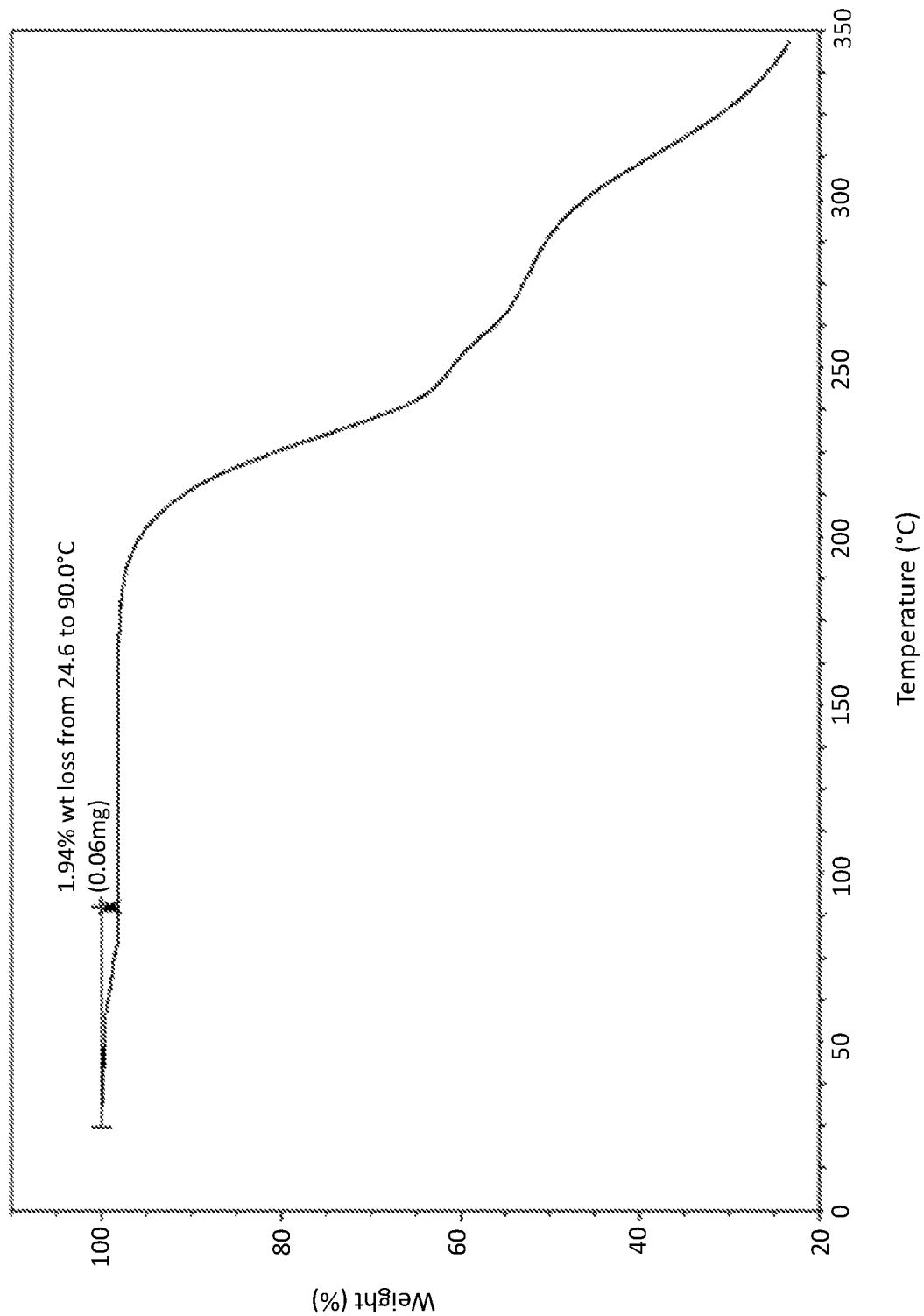
Figure 9:
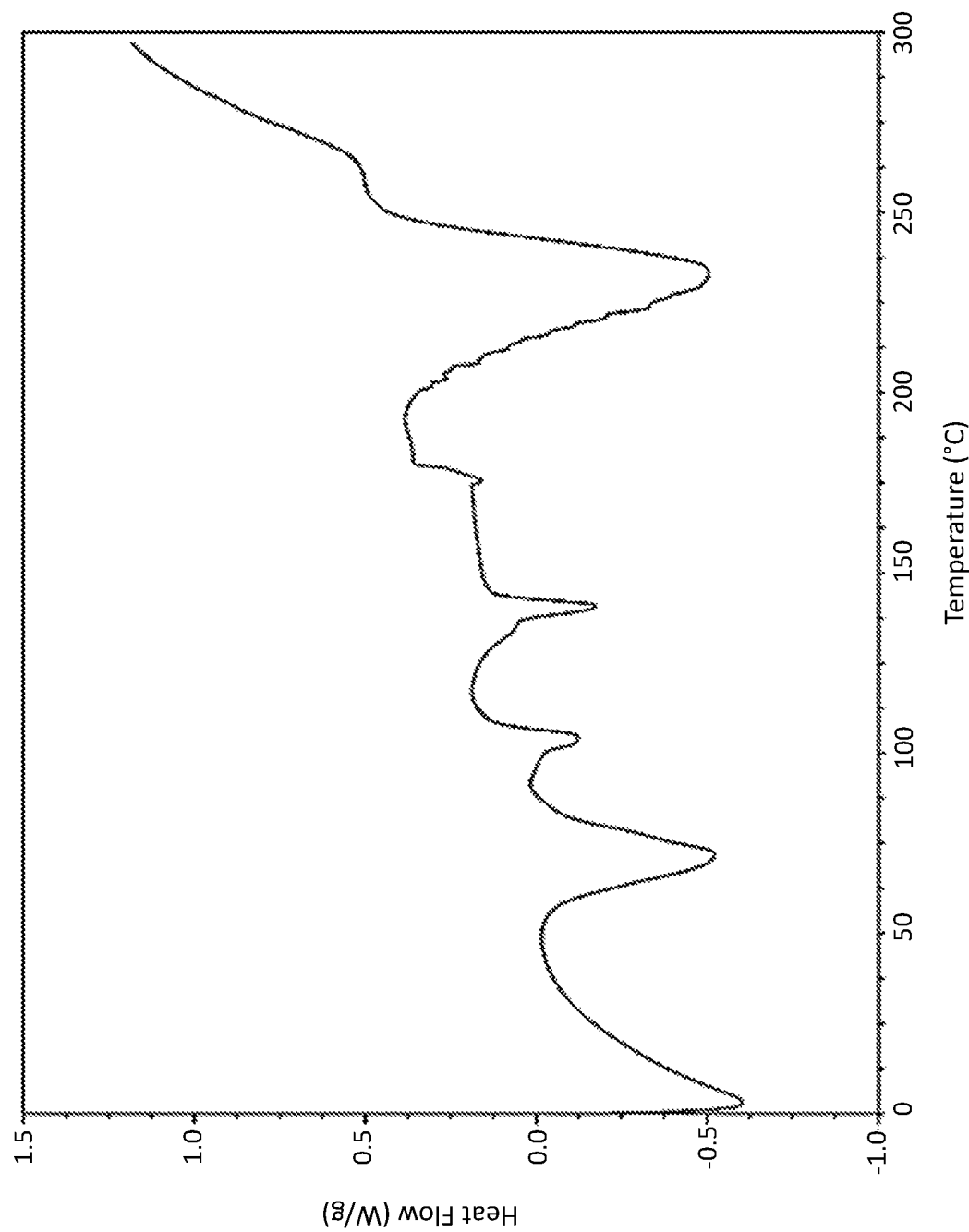

In some embodiments, crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, or a solvate thereof, is characterized by the TGA trace shown in FIG. 8. The DSC profile of crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, or a solvate thereof, is shown in FIG. 9.

The disclosure provides a process for preparing crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof, comprising:

(a) treating Formula (7a), or a salt thereof, or a solvate thereof, with isopropyl acetate (IPAc) to produce a solution;

(b) adding acetonitrile to the solution of step (a) to produce a mixture;

(c) charging the mixture from step (b) with a seed crystal;

(d) isolating the resulting solids to yield crystalline Formula (7a), or a solvate thereof.

In some embodiments of the process for preparing crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, 10% v/v IPAc/ACN doped with 0.75-2% w/w water with seeding may be used. Additionally, a long hold time at seeding temperature (e.g., >2 hours at between 60° C. and 65° C.) and a slow cooling ramp (e.g., 60° C. down to 0° C. at 5-10° C./hour) may be used to get a mobile slurry. Water content may be used in controlling the robustness of the crystallization. Crystallizations with 0.5-2% water added may be more reproducible with a consistent recovery (e.g., generally greater than 80%) and may have an upgrade in purity. This procedure may substantially purge the unreacted compound of formula (6a), a penta-Boc impurity (e.g., 63% purge combined), and the dialkylated by-product (e.g., 36% purge), and may afford readily filterable and washable solid product. Crystallization conditions screened are summarized in Example 3 and Tables 7-11.

EXEMPLARY EMBODIMENTS

Some embodiments of this disclosure are Embodiment I, as follows:

Embodiment I-1

A process for preparing a compound of formula (2), or a salt thereof, or solvate thereof, or an enantiomer thereof, or a diastereomer thereof comprising:

(a) contacting a compound of formula (1):

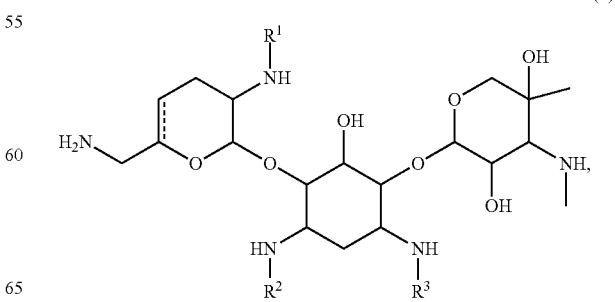

or an enantiomer thereof, or a diastereomer thereof, with 1-{[(p-nitrobenzyl)oxy]carbonyl}-1H-benzotriazole (PNZ-Bt) to form the compound of formula (2):

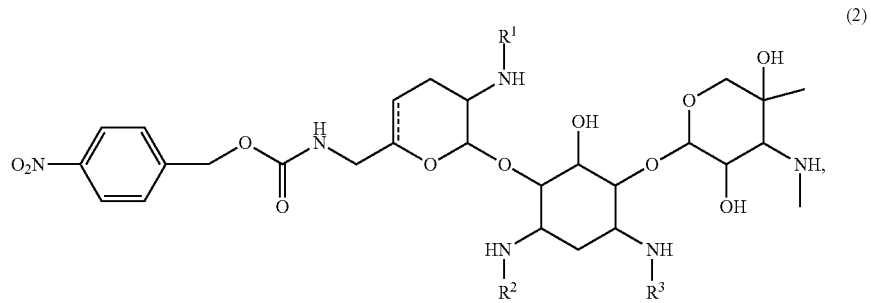

(2)

or a salt thereof, or a solvate thereof, or an enantiomer thereof, or a diastereomer thereof;

wherein === is a single bond or a double bond;

$R^1$ is H or $C_1$-$C_3$ alkyl;

$R^2$ is H or $C_1$-$C_3$ alkyl; and $R^3$ is H or $C_1$-$C_3$ alkyl.

Embodiment I-2

The process of embodiment I-1, wherein step (a) is performed in the presence of a solvent selected from the group consisting of dichloromethane, methanol, and a combination thereof.

Embodiment I-3

The process of embodiment I-1 or I-2, wherein the PNZ-Bt is present in about 1.0 to 1.2 molar equivalents to the compound of formula (1), or an enantiomer thereof, or a diastereomer thereof.

Embodiment I-4

The process of any one of embodiments I-1 to I-3, further comprising step (b1) or (b2):

(b1) wherein when $R^1$, $R^2$, and $R^3$ are H, contacting the compound of formula (2), or a salt thereof, or a solvate thereof, or an enantiomer thereof, or a diastereomer thereof, with a Boc protecting group reagent to yield a compound of formula (3):

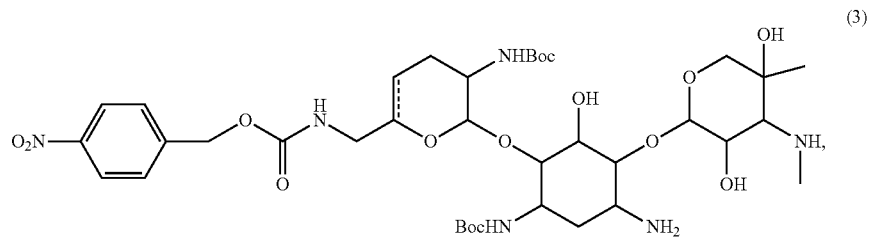

(3)

or a salt thereof, or a solvate thereof, or an enantiomer thereof, or a diastereomer thereof; or (b2) wherein when one or more of $R^1$, $R^2$, or $R^3$ is independently a $C_1$-$C_3$ alkyl, first removing said $C_1$-$C_3$ alkyl, and then contacting the compound of formula (2), or a salt thereof, or a solvate thereof, or an enantiomer thereof, or a diastereomer thereof, with a Boc protecting group reagent to yield a compound of formula (3):

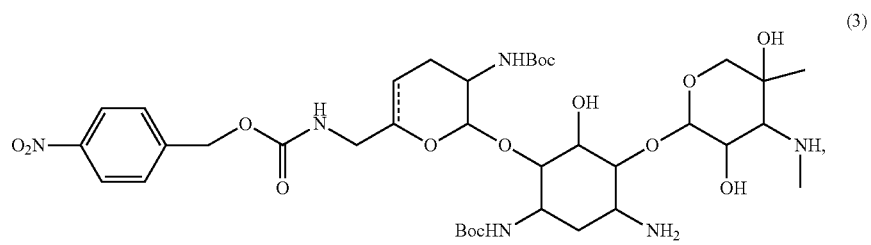

(3)

Embodiment I-5

The process of embodiment I-4, wherein the Boc protecting group reagent is Boc$_2$O or Boc-ONb.

Embodiment I-6

The process of embodiment I-4 or I-5, wherein step (b1) or (b2) is performed in the presence of a Lewis acid.

Embodiment I-7

The process of embodiment I-6, wherein the Lewis acid is Zn(OAc)$_2$, ZnCl$_2$, or Zn(OPiv)$_2$.

Embodiment I-8

The process of embodiment I-6, wherein the Lewis acid comprises a copper ion or a nickel ion.

Embodiment I-9

The process of any one of embodiments I-4 to I-8, wherein step (b1) or (b2) is performed in the presence of triethylamine.

Embodiment I-10

The process of any one of embodiments I-4 to I-8, wherein step (b1) or (b2) is performed in the presence of methanol.

Embodiment I-11

The process of any one of embodiments I-4 to I-10, further comprising:

(c) contacting the compound of formula (3), or a salt thereof, or a solvate thereof, or an enantiomer thereof, or a diastereomer thereof, with

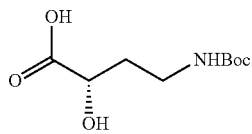 [SMILES: CC(C)(C)OC(=O)NCC[C@H](O)C(=O)O]

to yield a compound of formula (4):

Embodiment I-12

The process of embodiment I-11, wherein step (c) is performed in the presence of an activating reagent and a peptide coupling reagent.

Embodiment I-13

The process of embodiment I-12, wherein the activating reagent is HOBt.

Embodiment I-14

The process of embodiment I-13, wherein the activating reagent is present in about 0.05 to 1.0 molar equivalents to

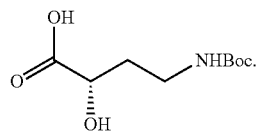 [SMILES: CC(C)(C)OC(=O)NCC[C@H](O)C(=O)O]

Embodiment I-15

The process of embodiment I-12, wherein the peptide coupling reagent is EDAC or PyBOP.

Embodiment I-16

The process of embodiment I-15, wherein the peptide coupling reagent is present in about 1.0 to 1.4 molar equivalents to

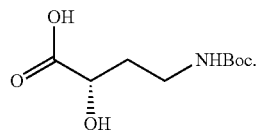 [SMILES: CC(C)(C)OC(=O)NCC[C@H](O)C(=O)O]

Embodiment I-17

The process of any one of embodiments I-11 to I-16, wherein step (c) is performed in an acidic condition.

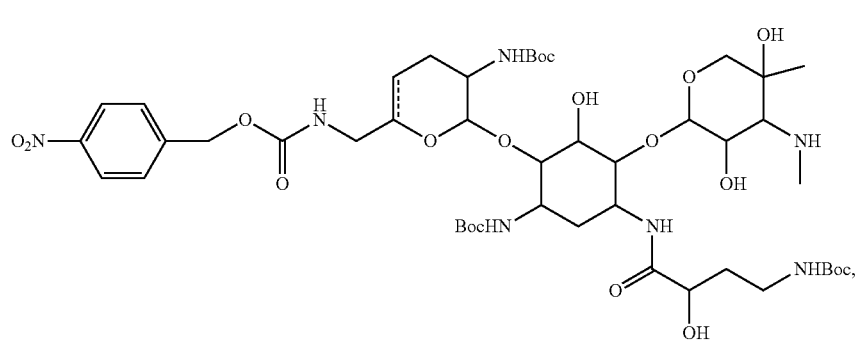

Embodiment I-18

The process of embodiment I-17, the acidic condition is pH between around 4 and 7.

Embodiment I-19

The process of embodiment I-17, the acidic condition is pH around 5.

Embodiment I-20

The process of any one of embodiments I-11 to I-19, further comprising preparing a crystalline form of compound of formula (4), or a salt thereof, or a solvate thereof, or an enantiomer thereof, or a diastereomer thereof.

Embodiment I-21

The process of any one of embodiments I-11 to I-20, further comprising isolating the compound of formula (4), or a salt thereof, or a solvate thereof, or an enantiomer thereof, or a diastereomer thereof.

Embodiment I-22

The process of any one of embodiments I-11 to I-21, further comprising:
(d) contacting the compound of formula (4), or a salt thereof, or a solvate thereof, or an enantiomer thereof, or a diastereomer thereof, with Boc protecting group reagent to yield a compound of formula (5):

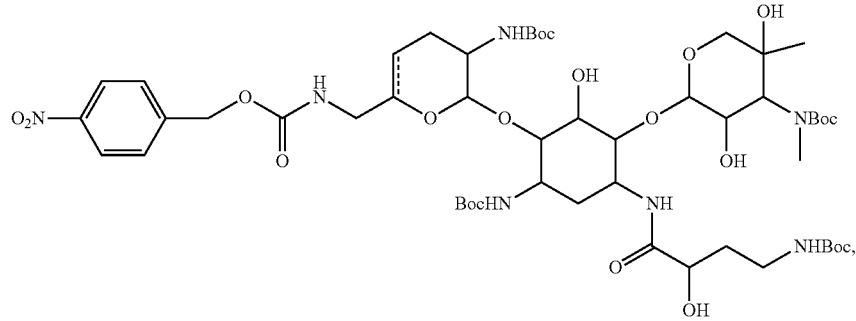

or a salt thereof, or a solvate thereof, or an enantiomer thereof, or a diastereomer thereof.

Embodiment I-23

The process of embodiment I-22, wherein the Boc protecting group reagent is Boc$_2$O.

Embodiment I-24

The process of embodiment I-22 or I-23, wherein step (d) is performed in the presence of an alcohol.

Embodiment I-25

The process of embodiment I-24, wherein the alcohol is methanol.

Embodiment I-26

The process of any one of embodiments I-22 to I-25, wherein step (d) is performed at a temperature of up to about 60° C.

Embodiment I-27

The process of any one of embodiments I-22 to I-26, further comprising:
(e) contacting the compound of formula (5), or a salt thereof, or a solvate thereof, or an enantiomer thereof, or a diastereomer thereof, with a PNZ deprotecting reagent to yield a compound of formula (6):

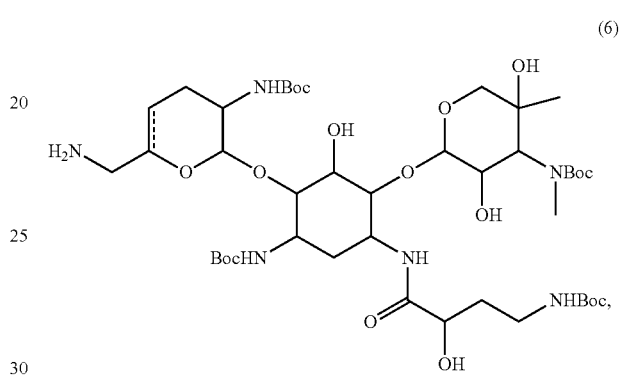

or a salt thereof, or a solvate thereof, or an enantiomer thereof, or a diastereomer thereof.

Embodiment I-28

The process of embodiment I-27, wherein the PNZ deprotecting reagent is sodium dithionite.

Embodiment I-29

The process of embodiment I-27 or I-28, further comprising preparing a crystalline form of compound of formula (6), or a salt thereof, or a solvate thereof, or an enantiomer thereof, or a diastereomer thereof.

Embodiment I-30

The process of any one of embodiments I-27 to I-29, further comprising isolating the compound of formula (6), or a salt thereof, or a solvate thereof, or an enantiomer thereof, or a diastereomer thereof.

Embodiment I-31

The process of any one of embodiments I-27 to I-30, further comprising:

(f) contacting the compound of formula (6), or a salt thereof, or a solvate thereof, or an enantiomer thereof, or a diastereomer thereof, with

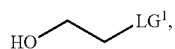

wherein LG¹ is a leaving group, to yield a compound of formula (7):

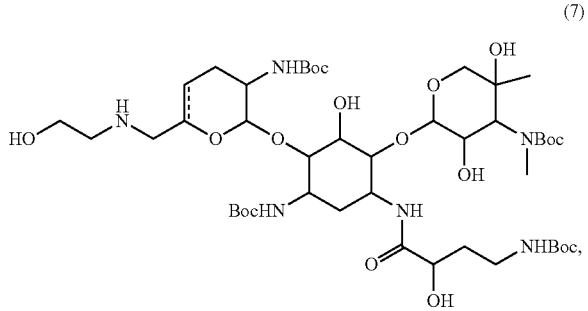

or a salt thereof, or a solvate thereof, or an enantiomer thereof, or a diastereomer thereof.

Embodiment I-32

The process of embodiment I-31, wherein the leaving group is iodo.

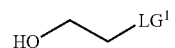

Embodiment I-33

The process of embodiment I-31, wherein the is present in about 1.0 to 1.5 molar equivalents to the compound of formula (6).

Embodiment I-34

The process of any one of embodiments I-31 to I-33, wherein step (f) is performed in conditions substantially free of water.

Embodiment I-35

The process of any one of embodiments I-31 to I-34, wherein step (f) is performed in the presence of a solvent selected from the group consisting of acetonitrile, acetone, and combination thereof.

Embodiment I-36

The process of any one of embodiments I-31 to I-35, wherein step (f) is performed in the presence of NaHCO₃.

Embodiment I-37

The process of any one of embodiments I-31 to I-36, wherein step (f) is performed at a temperature of about 30° C. to 40° C.

Embodiment I-38

The process of any one of embodiments I-31 to I-37, further comprising adding 1,4-diazabicyclo[2.2.2]octane (DABCO) to a reaction mixture.

Embodiment I-39

The process of any one of embodiments I-31 to I-38, further comprising preparing a crystalline form of compound of formula (7), or a salt thereof, or a solvate thereof, or an enantiomer thereof, or a diastereomer thereof.

Embodiment I-40

The process of any one of embodiments I-31 to I-39, further comprising isolating the compound of formula (7), or a salt thereof, or a solvate thereof, or an enantiomer thereof, or a diastereomer thereof.

Embodiment I-41

The process of any one of embodiments I-31 to I-40, further comprising:

(g) contacting the compound of formula (7) with a Boc removing reagent to yield a compound of formula (8):

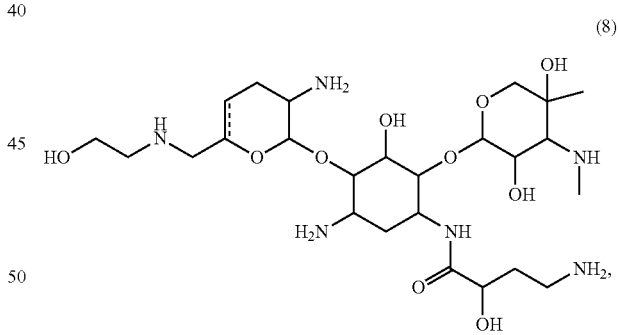

or a salt thereof, or a solvate thereof, or an enantiomer thereof, or a diastereomer thereof.

Embodiment I-42

The process of embodiment I-41, wherein the Boc removing reagent is TFA, thereby yielding a TFA salt of compound of formula (8), or a solvate thereof, or an enantiomer thereof, or a diastereomer thereof.

Embodiment I-42a

The process of embodiment I-41 or I-42, wherein compound (IMP-1)

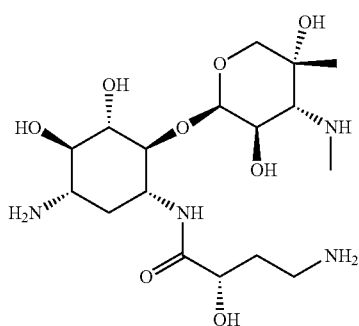

(IMP-1)

is present immediately after the reaction (e.g., before any purification) in an amount of less than 7%.

Embodiment I-42b

The process of embodiment I-41 or I-42, wherein compound (IMP-1)

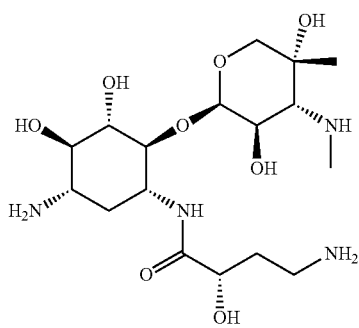

(IMP-1)

is present immediately after the reaction (e.g., before any purification) in an amount of less than 2.5%.

Embodiment I-43

The process of embodiment I-42, further comprising removing the TFA salt to afford a compound of formula (8), or a solvate thereof, or an enantiomer thereof, or a diastereomer thereof.

Embodiment I-44

The process embodiment I-41 or I-43, further comprising:

(h) performing a salt formation with an acid to yield a salt of a compound of formula (8), or a solvate thereof, or an enantiomer thereof, or a diastereomer thereof.

Embodiment I-45

The process of embodiment I-44, wherein the acid in step (h) is sulfuric acid, thereby yielding a sulfate salt of a compound of formula (9):

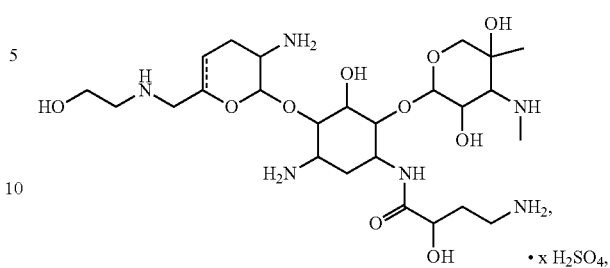

or a solvate thereof, or an enantiomer thereof, or a diastereomer thereof, wherein x is 1 to 5.

Embodiment I-46

The process of any one of embodiments I-1 to I-3, wherein $R^1$, $R^2$, or $R^3$ are H.

Embodiment I-47

The process of any one of embodiments I-1 to I-46, wherein === is a double bond.

Embodiment I-48

The process of any one of embodiments I-1 to I-10, wherein the stereochemistry at carbon atoms 1, 3, 4, 5, 6, 1', 2', 1", 2", 3", and 4" in formulae (1)-(3) are indicated as in formula (X), wherein ∼∼ indicates a point of attachment to hydrogen or a moiety:

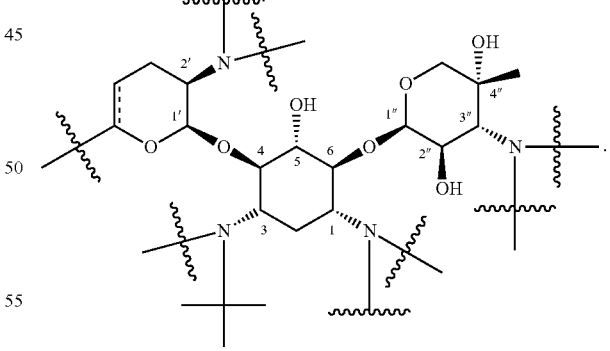

Embodiment I-49

The process of any one of embodiments I-11 to I-47, wherein the stereochemistry at carbon atoms 1, 3, 4, 5, 6, 1', 2', 1", 2", 3", 4", and 1-z in formulae (4)-(9) are indicated as in formula (Y), wherein ∼∼ indicates a point of attachment to hydrogen or a moiety:

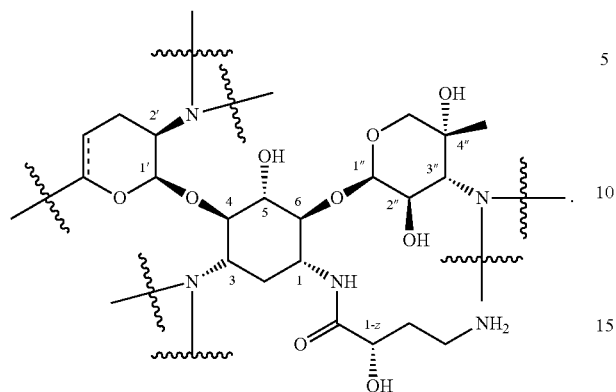

Embodiment I-50

A process for preparing a compound of formula (5):

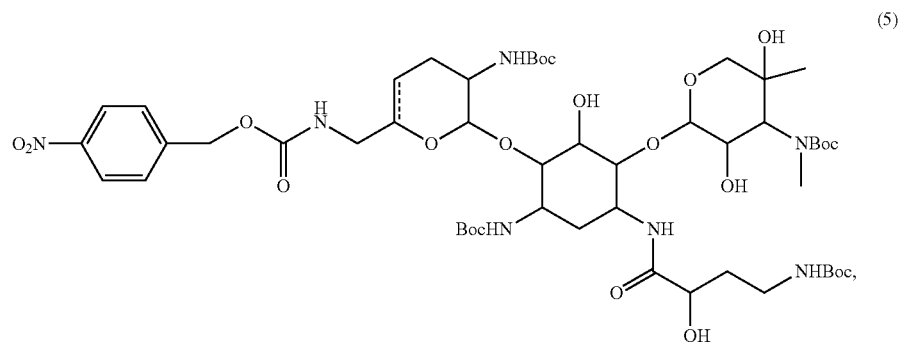

or a salt thereof, or a solvate thereof, or an enantiomer thereof, or a diastereomer thereof, the process comprising:
(a) contacting a compound of formula (4):

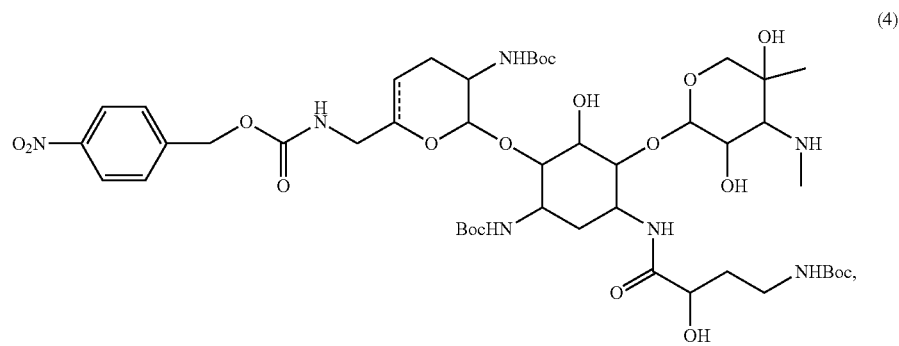

or a salt thereof, or a solvate thereof, or an enantiomer thereof, or a diastereomer thereof, with a Boc protecting group reagent, wherein === is a single bond or a double bond.

Embodiment I-51

The process of embodiment I-50, wherein the compound of formula (4), or a salt thereof, or a solvate thereof, or an enantiomer thereof, or a diastereomer thereof, is prepared by contacting a compound of formula (3):

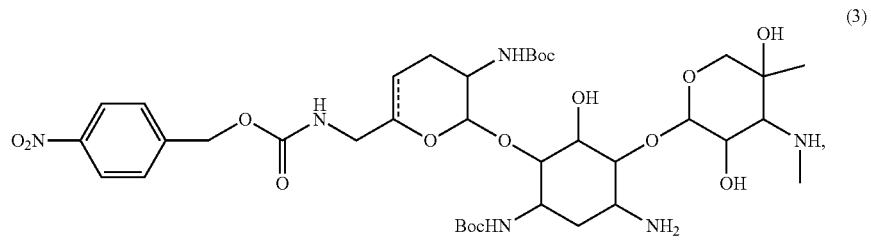

(3)

or a salt thereof, or a solvate thereof, or an enantiomer thereof, or a diastereomer thereof, with

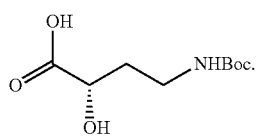 [SMILES: CC(C)(C)OC(=O)NCC[C@H](O)C(=O)O]

Embodiment I-52

The process of embodiment I-51, wherein the compound of formula (3), or a salt thereof, or a solvate thereof, or an enantiomer thereof, or a diastereomer thereof, is prepared by:
(b1) contacting a compound of formula (2a):

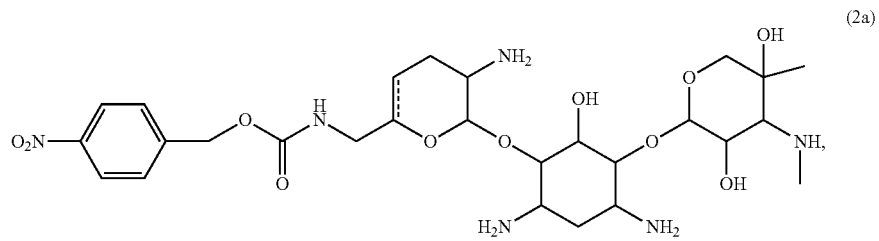

(2a)

or a salt thereof, or a solvate thereof, or an enantiomer thereof, or a diastereomer thereof, with a Boc protecting group reagent; or
(b2) removing $C_1$-$C_3$ alkyl in a compound of formula (2):

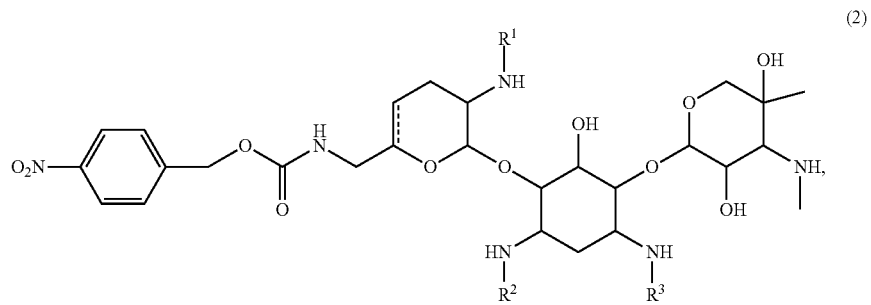

(2)

or a salt thereof, or a solvate thereof, or an enantiomer thereof, or a diastereomer thereof;

wherein $R^1$ is H or $C_1$-$C_3$ alkyl; $R^2$ is H or $C_1$-$C_3$ alkyl; and $R^3$ is H or $C_1$-$C_3$ alkyl, and wherein one or more of $R^1$, $R^2$, or $R^3$ is independently a $C_1$-$C_3$ alkyl; and then contacting the compound of formula (2), or a salt thereof, or a solvate thereof, or an enantiomer thereof, or a diastereomer thereof, with a Boc protecting group reagent.

Embodiment I-53

The process of embodiment I-52, wherein the compound of formula (2), or a salt thereof, or solvate thereof, or an enantiomer thereof, or a diastereomer thereof, is prepared by contacting a compound of formula (1):

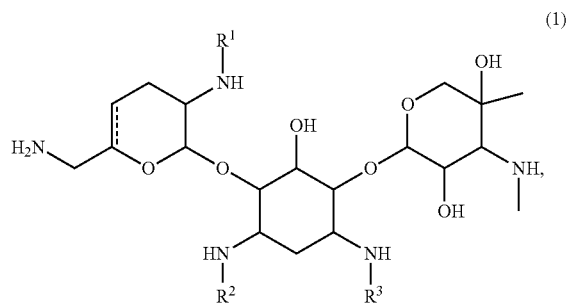

or an enantiomer thereof, or a diastereomer thereof, with 1-{[(p-nitrobenzyl)oxy]carbonyl}-1H-benzotriazole (PNZ-Bt).

Embodiment I-54

The process of any one of embodiments I-50 to I-53, wherein the Boc protecting group reagent is Boc$_2$O.

Embodiment I-55

The process of any one of embodiments I-50 to I-54, wherein step (a), (b1), or (b2) is performed in the presence of an alcohol.

Embodiment I-56

The process of embodiment I-55, wherein the alcohol is methanol.

Embodiment I-57

The process of any one of embodiments I-50 to I-56, wherein step (a), (b1), or (b2) is performed at a temperature of up to about 60° C.

Embodiment I-58

The process of any one of embodiments I-50 to I-57, further comprising:
(e) contacting the compound of formula (5), or a salt thereof, or a solvate thereof, or an enantiomer thereof, or a diastereomer thereof, with a PNZ deprotecting reagent to yield a compound of formula (6):

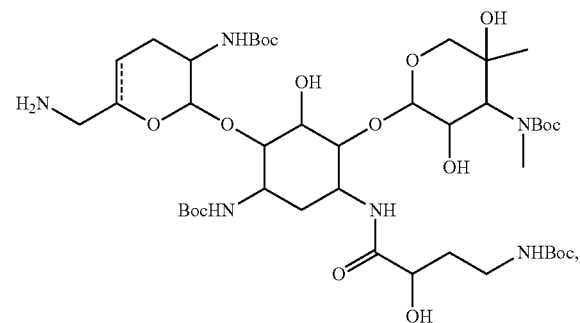

or a salt thereof, or a solvate thereof, or an enantiomer thereof, or a diastereomer thereof.

Embodiment I-59

The process of embodiment I-58, wherein the PNZ deprotecting reagent is sodium dithionite.

Embodiment I-60

The process of any one of embodiments I-50 to I-59, further comprising preparing a crystalline form of compound of formula (6), or a salt thereof, or a solvate thereof, or an enantiomer thereof, or a diastereomer thereof.

Embodiment I-61

The process of any one of embodiments I-50 to I-60, further comprising isolating the compound of formula (6), or a salt thereof, or a solvate thereof, or an enantiomer thereof, or a diastereomer thereof.

Embodiment I-62

The process of any one of embodiments I-50 to I-61, further comprising:
(f) contacting the compound of formula (6), or a salt thereof, or a solvate thereof, or an enantiomer thereof, or a diastereomer thereof, with

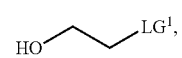

wherein LG$^1$ is a leaving group, to yield a compound of formula (7):

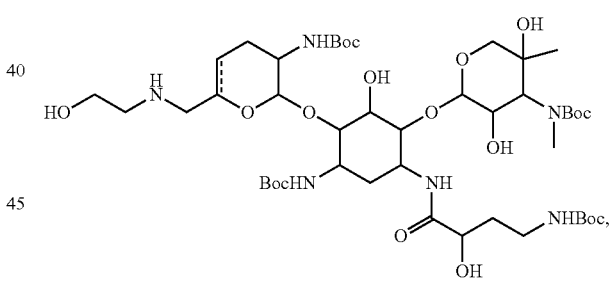

or a salt thereof, or a solvate thereof, or an enantiomer thereof, or a diastereomer thereof.

Embodiment I-63

The process of embodiment I-62, wherein the leaving group is iodo.

Embodiment I-64

The process of embodiment I-62, wherein the

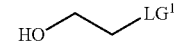

is present in about 1.0 to 1.5 molar equivalents to the compound of formula (6).

Embodiment I-65

The process of any one of embodiments I-62 to I-64, wherein step (f) is performed in conditions substantially free of water.

Embodiment I-66

The process of any one of embodiments I-62 to I-65, wherein step (f) is performed in the presence of a solvent selected from the group consisting of acetonitrile, acetone, and combination thereof.

Embodiment I-67

The process of any one of embodiments I-62 to I-66, wherein step (f) is performed in the presence of $NaHCO_3$.

Embodiment I-68

The process of any one of embodiments I-62 to I-67, wherein step (f) is performed at a temperature of about 30° C. to 40° C.

Embodiment I-69

The process of any one of embodiments I-62 to I-68, further comprising adding 1,4-diazabicyclo[2.2.2]octane (DABCO) to a reaction mixture.

Embodiment I-70

The process of any one of embodiments I-62 to I-69, further comprising preparing a crystalline form of compound of formula (7), or a salt thereof, or a solvate thereof, or an enantiomer thereof, or a diastereomer thereof.

Embodiment I-71

The process of any one of embodiments I-62 to I-70, further comprising isolating the compound of formula (7), or a salt thereof, or a solvate thereof, or an enantiomer thereof, or a diastereomer thereof.

Embodiment I-72

The process of any one of embodiments I-62 to I-71, further comprising:

(g) contacting the compound of formula (7), or a salt thereof, or a solvate thereof, or an enantiomer thereof, or a diastereomer thereof, with a Boc removing reagent to yield a compound of formula (8):

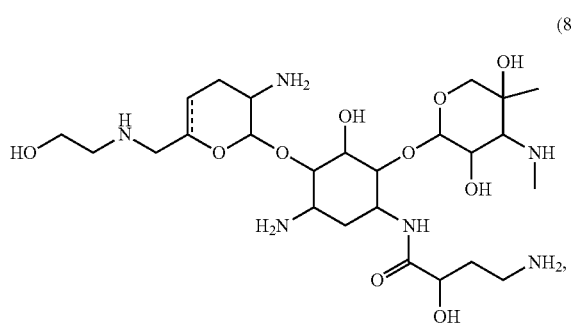

(8)

or a salt thereof, or a solvate thereof, or an enantiomer thereof, or a diastereomer thereof.

Embodiment I-73

The process of embodiment I-72, wherein the Boc removing reagent is TFA, thereby yielding a TFA salt of compound of formula (8), or a solvate thereof, or an enantiomer thereof, or a diastereomer thereof.

Embodiment I-74

The process of embodiment I-73, further comprising removing the TFA salt to afford a compound of formula (8), or a solvate thereof, or an enantiomer thereof, or a diastereomer thereof.

Embodiment I-75

The process of embodiment I-72 or I-74, further comprising:

(h) performing a salt formation with an acid to yield a salt of a compound of formula (8), or a solvate thereof, or an enantiomer thereof, or a diastereomer thereof.

Embodiment I-76

The process of embodiment I-75, wherein the acid in step (h) is sulfuric acid, thereby yielding a sulfate salt of a compound of formula (9):

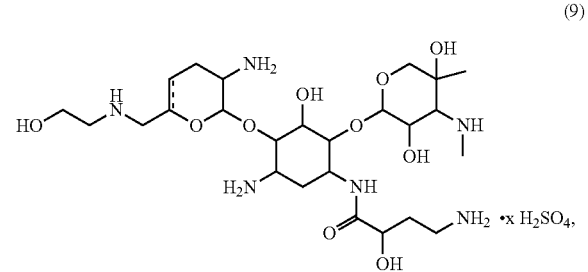

(9)

or a solvate thereof, or an enantiomer thereof, or a diastereomer thereof, wherein x is 1 to 5.

Embodiment I-77

A process for preparing a compound of formula (7):

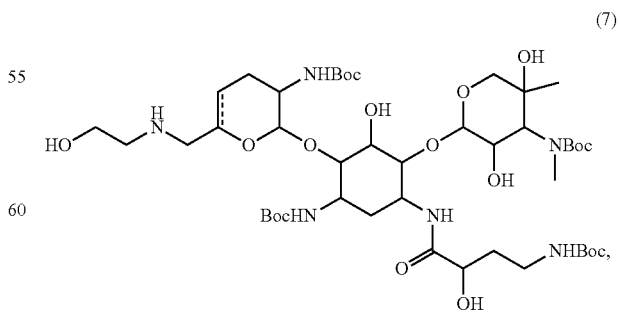

(7)

or a salt thereof, or a solvate thereof, or an enantiomer thereof, or a diastereomer thereof, the process comprising:

(f) contacting a compound of formula (6),

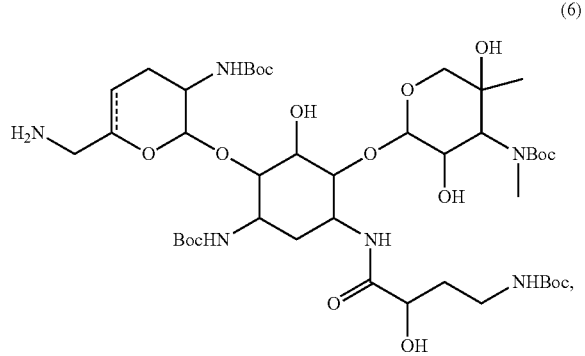

(6)

or a salt thereof, or a solvate thereof, or an enantiomer thereof, or a diastereomer thereof, with

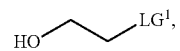

wherein LG$^1$ is a leaving group, and wherein === is a single bond or a double bond.

Embodiment I-78

The process of embodiment I-77, wherein the compound of formula (6), or a salt thereof, or a solvate thereof, or an enantiomer thereof, or a diastereomer thereof, is prepared by contacting a compound of formula (5):

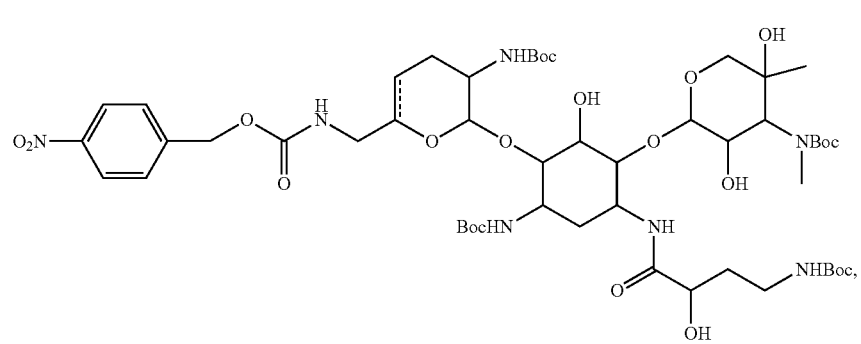

(5)

or a salt thereof, or a solvate thereof, or an enantiomer thereof, or a diastereomer thereof, with a PNZ deprotecting reagent.

Embodiment I-79

The process of embodiment I-78, wherein the compound of formula (5), or a salt thereof, or a solvate thereof, or an enantiomer thereof, or a diastereomer thereof, is prepared by contacting a compound of formula (4):

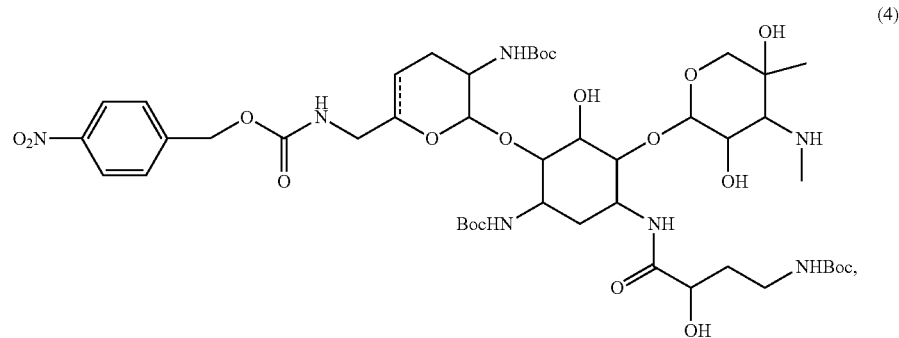

(4)

or a salt thereof, or a solvate thereof, or an enantiomer thereof, or a diastereomer thereof, with Boc protecting group reagent.

Embodiment I-80

The process of embodiment I-79, wherein the compound of formula (4), or a salt thereof, or a solvate thereof, or an enantiomer thereof, or a diastereomer thereof, is prepared by contacting a compound of formula (3):

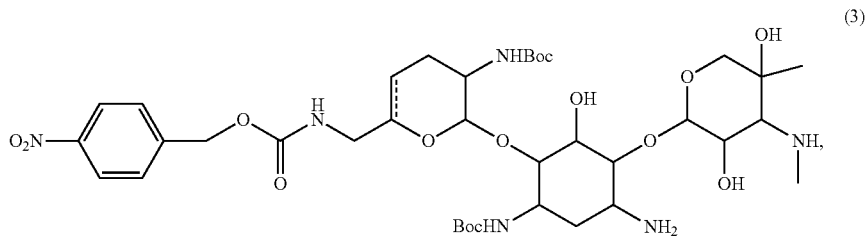
(3)

or a salt thereof, or a solvate thereof, or an enantiomer thereof, or a diastereomer thereof, with

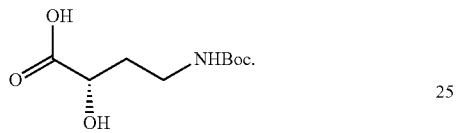

Embodiment I-81

The process of embodiment I-80, wherein the compound of formula (3), or a salt thereof, or a solvate thereof, or an enantiomer thereof, or a diastereomer thereof, is prepared by:

(b1) contacting a compound of formula (2a):

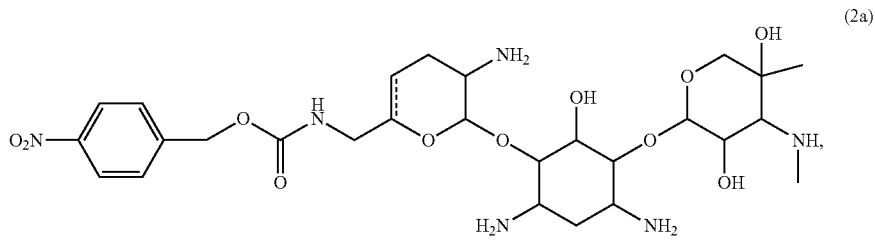
(2a)

or a salt thereof, or a solvate thereof, or an enantiomer thereof, or a diastereomer thereof; with a Boc protecting group reagent; or (b2) removing $C_1$-$C_3$ alkyl in a compound of formula (2):

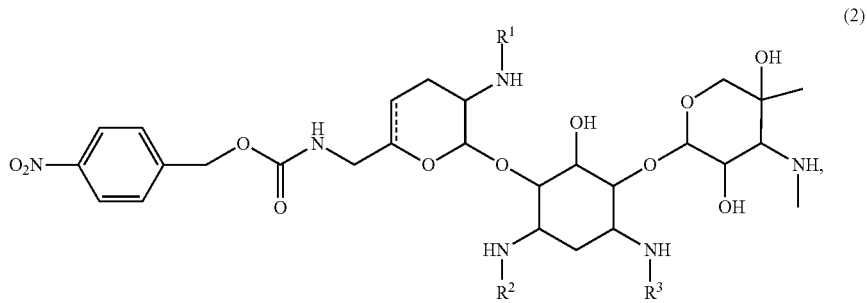
(2)

or a salt thereof, or a solvate thereof, or an enantiomer thereof, or a diastereomer thereof;
wherein $R^1$ is H or $C_1$-$C_3$ alkyl; $R^2$ is H or $C_1$-$C_3$ alkyl; and $R^3$ is H or $C_1$-$C_3$ alkyl, and wherein one or more of $R^1$, $R^2$, or $R^3$ is independently a $C_1$-$C_3$ alkyl; and
then contacting the compound of formula (2) with a Boc protecting group reagent.

Embodiment I-82

The process of embodiment I-81, wherein the compound of formula (2), or a salt thereof, or solvate thereof, or an enantiomer thereof, or a diastereomer thereof, is prepared by contacting a compound of formula (1):

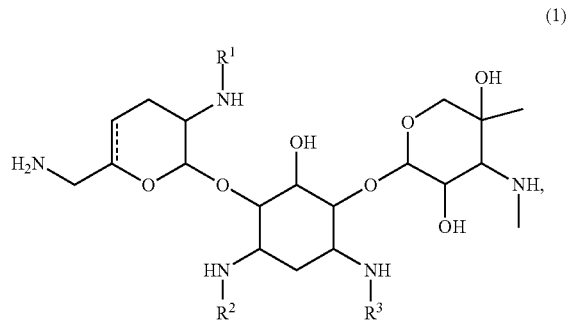

(1)

or an enantiomer thereof, or a diastereomer thereof, with 1-{[(p-nitrobenzyl)oxy]carbonyl}-1H-benzotriazole (PNZ-Bt).

Embodiment I-83

The process of any one of embodiments I-77 to I-82, wherein the leaving group is iodo.

Embodiment I-84

The process of embodiment I-83, wherein the

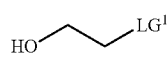

is present in about 1.0 to 1.5 molar equivalents to the compound of formula (6).

Embodiment I-85

The process of any one of embodiments I-77 to I-84, wherein step (f) is performed in conditions substantially free of water.

Embodiment I-86

The process of any one of embodiments I-77 to I-85, wherein step (f) is performed in the presence of a solvent selected from the group consisting of acetonitrile, acetone, and combination thereof.

Embodiment I-87

The process of any one of embodiments I-77 to I-86, wherein step (f) is performed in the presence of $NaHCO_3$.

Embodiment I-88

The process of any one of embodiments I-77 to I-87, wherein step (f) is performed at a temperature of about 30° C. to 40° C.

Embodiment I-89

The process of any one of embodiments I-77 to I-88, further comprising adding 1,4-diazabicyclo[2.2.2]octane (DABCO) to a reaction mixture.

Embodiment I-90

The process of any one of embodiments I-77 to I-89, further comprising preparing a crystalline form of compound of formula (7), or a salt thereof, or a solvate thereof, or an enantiomer thereof, or a diastereomer thereof.

Embodiment I-91

The process of any one of embodiments I-77 to I-90, further comprising isolating the compound of formula (7), or a salt thereof, or a solvate thereof, or an enantiomer thereof, or a diastereomer thereof.

Embodiment I-92

The process of any one of embodiments I-77 to I-91, further comprising:
(g) contacting the compound of formula (7), or a salt thereof, or a solvate thereof, or an enantiomer thereof, or a diastereomer thereof, with a Boc removing reagent to yield a compound of formula (8):

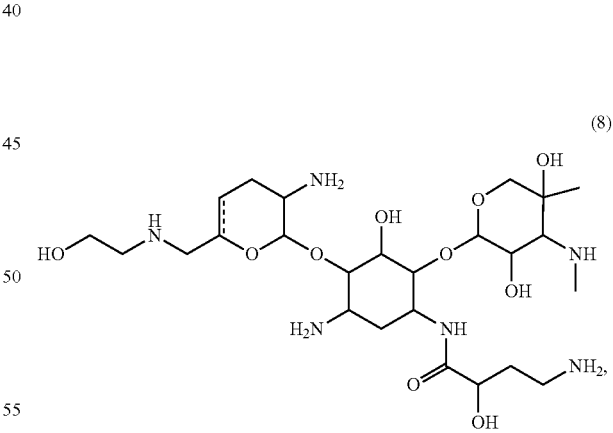

(8)

or a salt thereof, or a solvate thereof, or an enantiomer thereof, or a diastereomer thereof.

Embodiment I-93

The process of embodiment I-92, wherein the Boc removing reagent is TFA, thereby yielding a TFA salt of compound of formula (8), or a solvate thereof, or an enantiomer thereof, or a diastereomer thereof.

Embodiment I-94

The process of embodiment I-93, further comprising removing the TFA salt to afford a compound of formula (8), or a solvate thereof, or an enantiomer thereof, or a diastereomer thereof.

Embodiment I-95

The process of embodiment I-92 or I-94, further comprising:

(h) performing a salt formation with an acid to yield a salt of a compound of formula (8), or a solvate thereof, or an enantiomer thereof, or a diastereomer thereof.

Embodiment I-96

The process of embodiment I-95, wherein the acid in step (h) is sulfuric acid, thereby yielding a sulfate salt of a compound of formula (9):

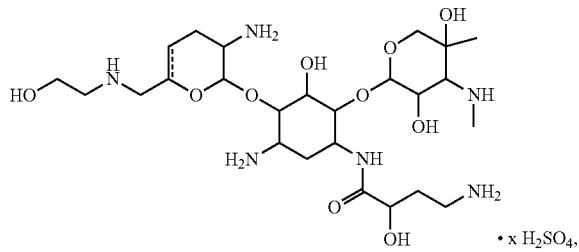

(9)

or a solvate thereof, or an enantiomer thereof, or a diastereomer thereof, wherein x is 1 to 5.

Embodiment I-97

The process of any one of embodiments I-50 to I-96, wherein === is a double bond.

Embodiment I-98

A compound of formula (4):

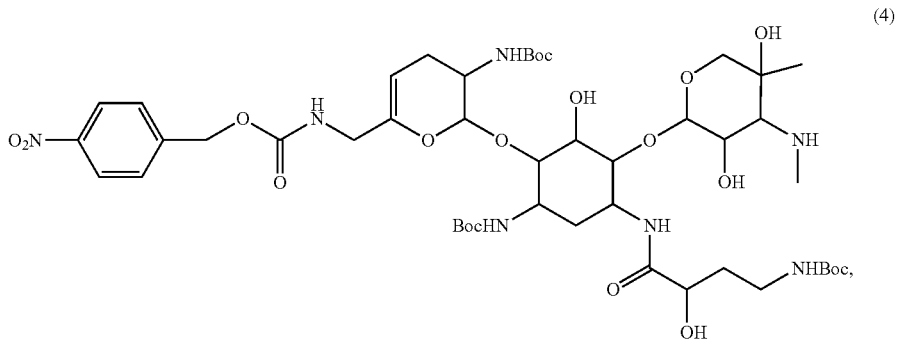

(4)

or a salt thereof, or a solvate thereof, or an enantiomer thereof, or a diastereomer thereof.

Embodiment I-99

The compound of embodiment I-98, wherein the compound of formula (4) is of the following formula:

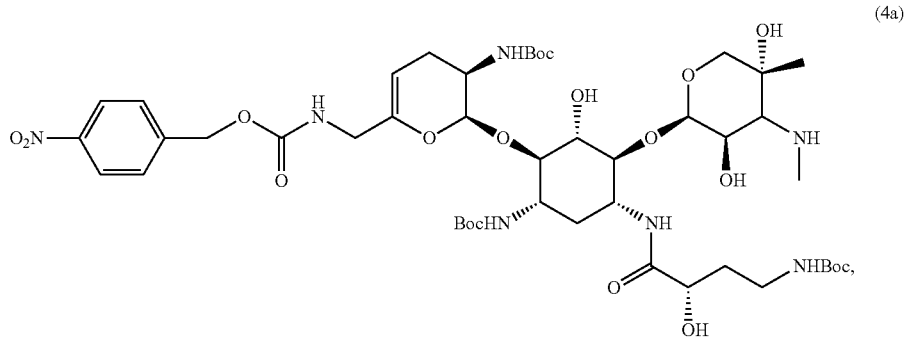

(4a)

or a salt thereof, or a solvate thereof.

87

Embodiment I-100

Crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, Formula (4a), or a solvate thereof.

Embodiment I-101

A process for preparing crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, Formula (4a), or a solvate thereof, comprising:
(a) treating Formula (4a), or a salt thereof, or a solvate thereof, with acetonitrile to produce a solution;
(b) heating the solution from step (a);
(c) adding water to the heated solution of step (b);
(d) cooling the solution from step (c);
(e) charging the solution from step (d) with a seed crystal; and
(f) isolating the resulting solids to yield crystalline Formula (4a), or a solvate thereof.

Embodiment I-102

Crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof.

Embodiment I-103

A process for preparing crystalline tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof, comprising:
(a) treating Formula (6a), or a salt thereof, or a solvate thereof, with isopropyl acetate (IPAc) to produce a solution;
(b) adding water to the solution of step (a) to produce a mixture;
(c) adding dichloromethane to the mixture from step (b) to produce a mixture;
(d) charging the mixture from step (c) with a seed crystal;
(e) isolating the resulting solids to yield crystalline Formula (6a), or a solvate thereof.

Embodiment I-104

The process of embodiment I-103, wherein step (d) is performed at a low temperature.

88

Embodiment I-105

A compound of formula (7):

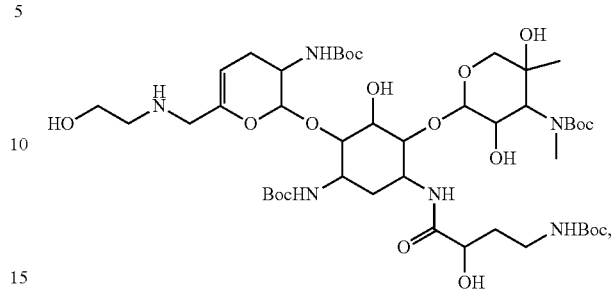

or a salt thereof, or solvate thereof, or an enantiomer thereof, or a diastereomer thereof.

Embodiment I-106

The compound of embodiment I-105, wherein the compound of formula (7) is of the following formula:

(7a)

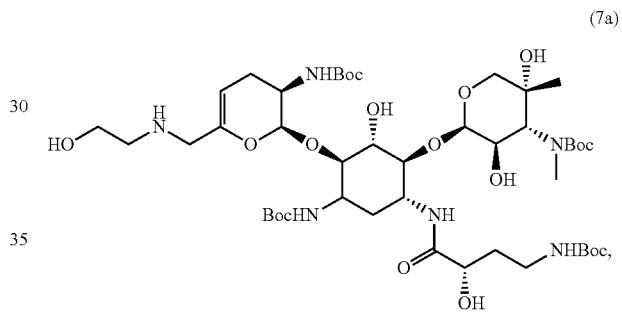

or a salt thereof, or a solvate thereof.

Embodiment I-107

Crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof.

Embodiment I-108

A process for preparing crystalline tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof, comprising:
(a) treating Formula (7a), or a salt thereof, or a solvate thereof, with isopropyl acetate (IPAc) to produce a solution;
(b) adding acetonitrile to the solution of step (a) to produce a mixture;

(c) charging the mixture from step (b) with a seed crystal;
(d) isolating the resulting solids to yield crystalline Formula (7a), or a solvate thereof.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Unless otherwise noted, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

Sisomicin freebase is a fermented glycoside and was obtained from Zhejiang Zhenyuan Pharmaceutical Co. Ltd. Boc-(S)-HABA was obtained from Senn Chemicals AG or Porton Fine Chemicals Inc. PNZ-Bt was obtained from Luxembourg BioTechnologies LTD (KINSY S.L.) or Porton Fine Chemicals Inc. 2-Iodoethanol was obtained from Dona Chemicals, Poland.

The following abbreviations have the following meanings unless otherwise indicated and any other abbreviations used herein and not defined have their standard generally accepted meaning:
% a/a: area normalized percent
Ac: acetate
ACN: acetonitrile
Boc: tert-butoxycarbonyl
$BocO_2$: di-tert-butyl dicarbonate or Boc anhydride
Boc-ONb: tert-butyl ((4R,7S)-1,3-dioxo-1,3,3a,4,7,7a-hexahydro-2H-4,7-methanoisoindol-2-yl) carbonate
DABCO: 1,4-diazabicyclo[2.2.2]octane
DBU: 1,8-diazabicyclo[5.4.0]undec-7-ene
DCM: dichloromethane
DI: deionized water
DIPE: diisoproyl ether
DIPEA: N,N-diisopropylethylamine
DMF: dimethylformamide,
DSC: differential scanning calorimetry
EDAC: N-(3-dimethylaminopropyl)-N'-ethylcarbodiimide hydrochloride
EtOH: ethanol
GC: gas chromatography
h or hr: hour(s)
HABA: 4-amino-2-hydroxy-butanoic acid
HCl: hydrochloric acid
HOBt: 1-hydroxybenzotriazole hydrate
HPLC: high performance liquid chromatography
IPA: isopropyl alcohol
IPAc: isopropyl acetate
LC/MS: liquid chromatography/mass spectrometry
MeCN: acetonitrile
MeOH: methanol
min: minute(s)
MTBE: methyl tert-butyl ether
NaOH: sodium hydroxide
PNZ-Bt: 1-{[(p-nitrobenzyl)oxy]carbonyl}-1H-benzotriazole
ppm: parts per million
PrOH: propanol
PyBOP: (benzotriazol-1-yloxy)tripyrrolidinophosphonium hexafluorophosphate
RT or rt: room temperature
TBDMS: tert-butyldimethylsilyl
TEA: triethylamine
TFA: trifluoroacetic acid
TGA: thermogravimetric analysis
THF: tetrahydrofuran
UPLC: ultra performance liquid chromatography
UV: ultraviolet
v/v: volume by volume
vol or vols: volume(s)
% w/w: weight for weight percent
wt: weight
XRPD: x-ray power diffraction
$Zn(OPiv)_2$: zinc pivalate X-Ray Power Diffraction XRPD patterns were collected with a PANalytical X'Pert PRO MPD diffractometer using an incident beam of Cu radiation produced using an Optix long, fine-focus source. An elliptically graded multilayer mirror was used to focus Cu Kα x-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3 μm-thick films and analyzed in transmission geometry. A beam-stop, short antiscatter extension, and antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Thermal Analysis

Differential scanning calorimetry (DSC) was performed using a TA Instruments DSC with a temperature ramp from 0° C. to 300° C. at a rate of 10° C./minute. Standard aluminum pans were used.

Thermogravimetric analysis (TGA) was performed using a TA Instruments 2950 thermogravimetric analyzer. Temperature calibration was performed using nickel and Alumel™. Each sample was placed in a platinum pan and inserted into the TG furnace. The furnace was heated under a nitrogen purge.

Example 1—Synthetic Protocol for Compound 4a

Detailed below is a general synthetic protocol for Compound 4a.

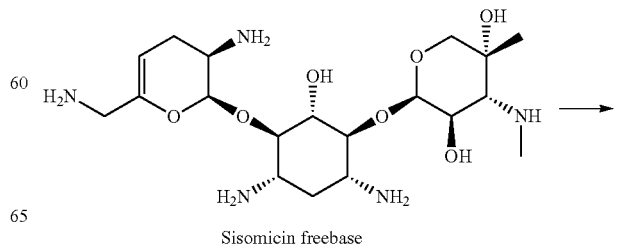

Sisomicin freebase

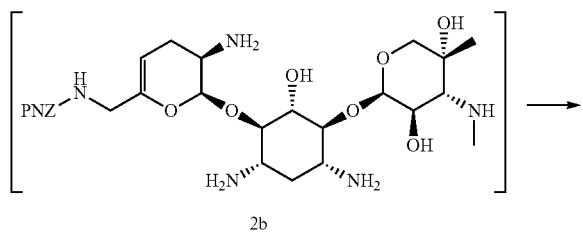

2b

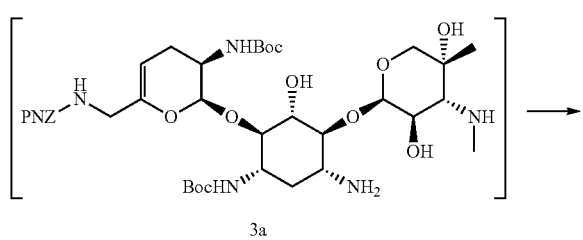

3a

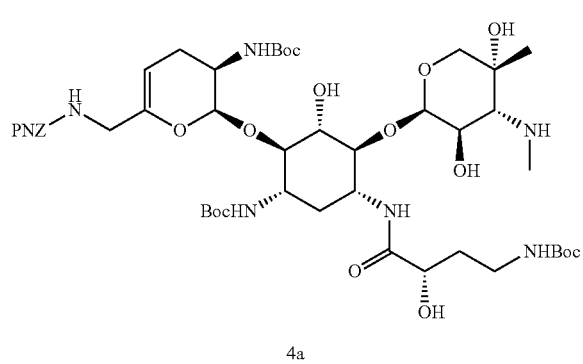

4a

Part 1: Synthesis of Compound 2b

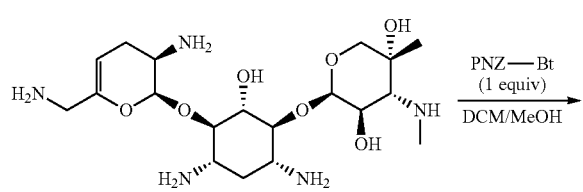

2b

Sisomicin freebase (1.0 kg±1%, 2.23 mol) is charged into a reactor, followed by MeOH (3.96 kg±5% or 5 L±5%) and then DCM (6.64 kg±5% or 5 L±5%). The temperature is then stabilized to 15±5° C. and the mixture is agitated to achieve full dissolution. The temperature can be increased to about 30° C. in order to aid dissolution. After dissolution, the mixture is cooled to a temperature of 15±5° C. In a separate mixing tank, PNZ-Bt [(0.696 kg)±1%, 2.33 mol)] is dissolved in DCM (18.59 kg±5% or 14 L±5%). The PNZ-Bt solution is charged to the reactor over a period of about 1 to about 4 hours, while maintaining a batch temperature of 15±5° C. When preparing the PNZ-Bt solution, the charging tank jacket is not heated to more than or equal to about 35° C. to facilitate the dissolution of PNZ-Bt. Complete dissolution of PNZ-Bt is not required.

The charging system used for the charge of the PNZ-Bt solution is rinsed with DCM (1.33 kg±5% or 1 L±5%) and the rinse is fed into the reactor ($T_{Batch}$=15±5° C.). The batch is agitated at 15±5° C. and the contents sampled for reaction completion. The reaction is deemed complete when the content of sisomicin is not more than or equal to about 2.0% in area as assessed by HPLC analysis (see Table 3 for the HPLC method used). The first sample is taken approximately from 15 minutes to 12 hours after completion of the PNZ-Bt charge. In some embodiments, the first sample is taken approximately 30 minutes after completion of the PNZ-Bt charge. Additional PNZ-Bt in a DCM solution is charged as needed to complete the reaction. The amount of additional PNZ-Bt charged is calculated with the following formula: Charge=P1*D1/(100−D1±1%, where P1=the quantity of PNZ-Bt in kg initially charged and D1=the quantity of unconsumed sisomicin in % area by HPLC. Once the reaction is complete, the batch is concentrated under vacuum with a jacket temperature of no more than or equal to about 40° C. (e.g., 10 to 40° C.) until the residual volume is 5 L±5%.

The reactor containing Compound 2b is then charged with MeOH (5.54 kg±5% or 7.00 L±5%). The mixture can be maintained at a temperature no more than or equal to about 25° C. (e.g., 0 to 25° C.) for no more than or equal to about 48 hours (e.g., 0 to 48 hours) before the next reaction (Part 2).

TABLE 3

| HPLC Method for Part 1 of Example 1 | |
|---|---|
| Column | Waters X-Bridge C18, 3.5 μm 150 mm × 4.6 mm |
| Column Temperature | 40° C. |
| Flow Rate | 1 mL/min |
| Detection Wavelength | 210 nm |
| Mobile Phases | 0.25 M NH₄OH in water |
| | 0.25 M NH₄OH in methanol |
| Gradient | Time (min) % Mobile Phase A % Mobile Phase B |
| | 0.00    85    15 |
| | 28.0    15    85 |
| | 30.0    15    85 |
| | 30.1    85    15 |
| | 40.0    85    15 |
| Run Time | 40 min |
| Injection Volume | 10 μL |

Part 2: Synthesis of Compound 3a

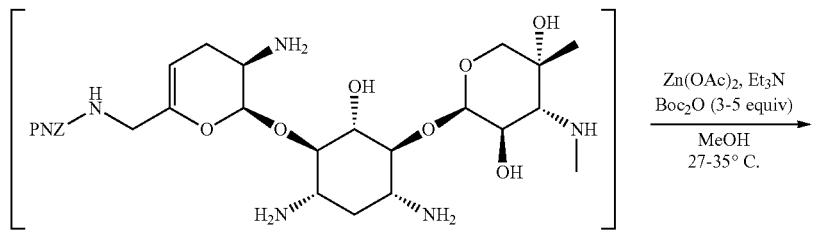

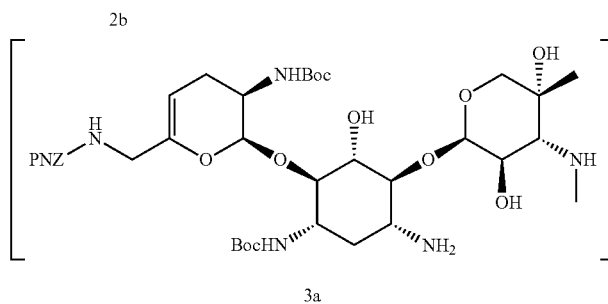

Triethylamine [(1.48 L)±2% or (1.08 kg±2%)] is charged to the reactor containing Compound 2b referred to at the end of Part 1 while maintaining a batch temperature of about 27° C. to about 35° C. (target about 33° C.). The charging system used for the charge of triethylamine is rinsed with MeOH (2.38 kg±5% or 3.00 L±5%), and the rinse is added to the reaction mixture. The batch temperature is stabilized to about 27° C. to about 35° C. (target about 33° C.). Zn(OAc)$_2$·2H$_2$O (1.63 kg±2%) is charged to the batch and the charging system used for the charge of zinc acetate dihydrate is rinsed with MeOH (2.38 kg±5% or 3.00 L±5%), and the rinse is added to the reaction mixture. The mixture is agitated from about 30 minutes to 12 hours at about 27° C. to about 35° C. (target about 33° C.). In certain embodiments, the mixture is agitated no longer than or equal to about 60 minutes at about 27° C. to about 35° C. (target about 33° C.).

In a separate mixing tank, a solution of Boc$_2$O [(2.55 kg)±2%, 11.7 mol] in MeOH (1.58 kg±5% or 2.00 L±5%) is prepared. The Boc$_2$O solution prepared is charged to the reactor over about 15 minutes to 12 hours while maintaining a batch temperature of about 27° C. to about 35° C. (target about 33° C.). In certain embodiments, the Boc$_2$O solution prepared is charged to the reactor over no longer than or equal to about 1 hour while maintaining a batch temperature of about 27° C. to about 35° C. (target about 33° C.). The charging system used for the Boc$_2$O solution is rinsed with methanol (0.16 kg±5% or 0.20 L±5%) and the rinse is added to the reactor.

The batch is held at a target temperature of about 20 to 40° C. for about 3 to 24 hours and the sample the contents sampled for reaction completion. In certain embodiments, the batch is held at a target temperature of about 33° C. for no longer than or equal to about 5 hours and the sample the contents sampled for reaction completion. The reaction is deemed complete when the content of a mono-Boc-Compound 2b intermediate:

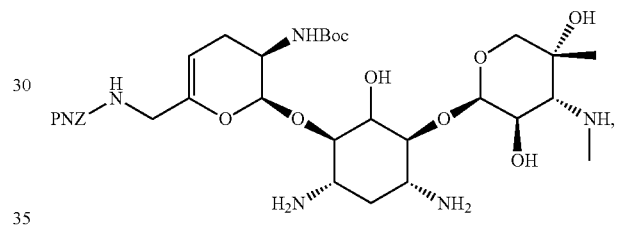

relative to Compound 3a is no more than or equal to about 2.0% in area by HPLC analysis (see Table 4 for the HPLC method used). The first sample taken to check for reaction completion is taken after about 15 minutes to 12 hours. In certain embodiments, the first sample taken to check for reaction completion is taken after not less than or equal to about 5 hours and subsequent samples (if needed) are taken at intervals of approximately 3 hours. The batch temperature during this hold does not deviate outside the range of about 27–35° C. In certain instances, additional Boc$_2$O is charged to complete the reaction. The charge is made with the same concentration of Boc$_2$O used in the Boc$_2$O solution prepared above. The amount of Boc$_2$O to be charged is calculated according to the following formula: Charge=P2*2*D2/[100−(2*D20]±2%, where: P2=the quantity of Boc$_2$O in kg initially charged and D2=the quantity of remaining mono-Boc-Compound 2b in % area by HPLC.

Once the reaction is complete, the reaction mixture is concentrated under vacuum at a jacket temperature of no more than or equal to about 40° C. (e.g., 20 to 40° C.) until the residual volume is 12 L±5%. Ammonia at about 25% w/w (5.46 kg±5% or 6.00 L±5%) is charged while maintaining a batch temperature of about 20° C. to about 30° C. and held for about 15 minutes to 12 hours at this temperature range. In certain embodiments, ammonia at about 25% w/w (5.46 kg±5% or 6.00 L±5%) is charged while maintaining a batch temperature of about 20° C. to about 30° C. and held for no longer than or equal to about 1 hour at this temperature range. The addition is exothermic.

DCM (13.28 kg±5% or 10.00 L±5%) is charged to the batch and the contents agitated for about 12 minutes to 12 hours at 25±5° C. In certain embodiments, DCM (13.28 kg±5% or 10.00 L±5%) is charged to the batch and the contents agitated for no longer than or equal to about 30 minutes at 25±5° C. The contents are allowed to settle and separate for about 30 minutes to 12 hours. In certain embodiments, the contents are allowed to settle and separate for at least or equal to about 45 minutes. The organic phase (lower phase) is transferred into a receiver and the aqueous phase is discharged for disposal. The product is in the organic phase.

The organic phase is charged back to the reactor. Ammonia at about 25% w/w (2.28 kg±5% or 2.50 L±5%) and DI water (2.5 kg±5% or 2.5 L±5%) mixed in a mixing tank are charged to the organic phase and agitated for about 15 minutes to 12 hours at 25±5° C. In certain embodiments, ammonia at about 25% w/w (2.28 kg±5% or 2.50 L±5%) and DI water (2.5 kg±5% or 2.5 L±5%) mixed in a mixing tank are charged to the organic phase and agitated for no longer than or equal to about 30 minutes at 25±5° C. The contents are allowed to settle and separate for about 30 minutes to 12 hours. In certain embodiments, the contents are allowed to settle and separate for at least or equal to about 45 minutes. The organic phase (lower phase) is transferred into a receiver and the aqueous phase is discharged for disposal. The product is in the organic phase.

The organic phase is charged back to the reactor and MeOH (0.79 kg±5% or 1.00 L±5%) is charged to the organic phase and stirred for about 15 to about 30 minutes at 25±5° C. DI water (5.0 kg±5% or 5.0 L±5%) is charged to the mixture and stirred about 15 minutes to 12 hours at 25±5° C. In certain embodiments, DI water (5.0 kg±5% or 5.0 L±5%) is charged to the mixture and stirred for no longer than or equal to about 30 minutes at 25±5° C. The contents are allowed to settle and separate for about 30 minutes to 12 hours. In certain embodiments, the contents are allowed to settle and separate for at least or equal to about 1 hour. The organic phase (lower phase) is transferred into a receiver and the aqueous phase is discharged for disposal. The product is in the organic phase.

The organic phase is charged back to the reactor. MeOH (1.98 kg±5% or 2.50 L±5%) is charged to the organic phase and stirred for about 15 to about 30 minutes at 25±5° C. DI water (5.0 kg±5% or 5.0 L±5%) is charged to the mixture and stirred for about 15 minutes to 12 hours at 25±5° C. In certain embodiments, DI water (5.0 kg±5% or 5.0 L±5%) is charged to the mixture and stirred for no longer than or equal to about 30 minutes at 25±5° C. The contents are allowed to settle and separate for about 30 minutes to 12 hours. In certain embodiments, the contents are allowed to settle and separate for at least or equal to about 2 hours. The organic phase (lower phase) is transferred into a receiver and the aqueous phase is discharged for disposal. The product is in the organic phase. The batch is under vacuum at a jacket temperature of no more than or equal to about 40° C. (e.g., 20 to 40° C.) until the residual volume is approximately 9 L±5%. The mixture can be maintained at a temperature no more than or equal to about 25° C. (e.g., 0 to 25° C.) for no more than or equal to about 48 hours (e.g., 0 to 48 hours).

TABLE 4

HPLC Method for Parts 2 and 3 of Example 1

| Column | Waters X-Bridge C18, 3.5 μm 150 mm × 4.6 mm | | |
|---|---|---|---|
| Column Temperature | 40° C. | | |
| Flow Rate | 1 mL/min | | |
| Detection Wavelength | 274 nm | | |
| Mobile Phases | 0.25 M NH$_4$OH in water | | |
| | 0.25 M NH$_4$OH in methanol | | |
| Gradient | Time (min) | % Mobile Phase A | % Mobile Phase B |
| | 0 | 90 | 10 |
| | 5.0 | 50 | 50 |
| | 35.0 | 10 | 90 |
| | 40.0 | 10 | 90 |
| | 40.1 | 90 | 10 |
| | 45.0 | 90 | 10 |
| Run Time | 45 min | | |
| Injection Volume | 10 μL | | |

Part 3: Synthesis of Compound 4a

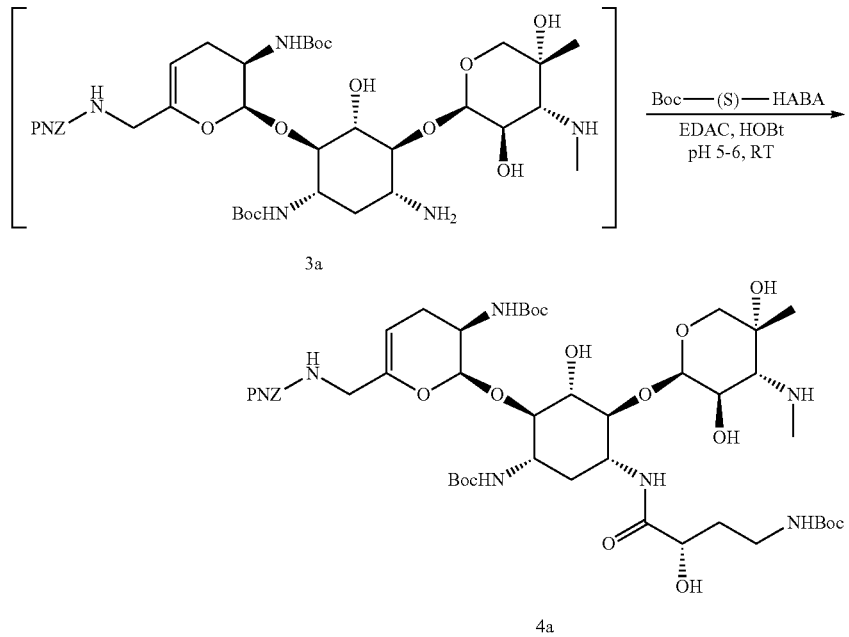

DI water (0.5 kg±5% or 0.5 L±5%) is charged to the mixture from Part 2 comprising Compound 3a while maintaining a reaction temperature of 20±5° C. Boc-(S)-HABA [(0.512 kg)±2%, 2.34 mol] is charged to the reaction mixture and the temperature is maintained within the 20±5° C. range. The charging system used for the charge of the Boc-(S)-HABA is rinsed with DCM (0.27 kg±5% or 0.20 L±5%) and the rinse is added to the reaction mixture. The mixture is agitated at a batch temperature of 20±5° C.

1-Hydroxybenzotriazole monohydrate (HOBt.H$_2$O, 0.057 kg±2%, 0.42 mol) is charged while maintaining a reaction temperature of 20±5° C. The charging system used for the charge of the HOBt.H$_2$O is rinsed with DCM (0.27 kg±5% or 0.2 L±5%) and the rinse is added to the reaction mixture.

The pH of the batch is adjusted to 5.0±0.2 while maintaining a temperature range of 20±5° C. The batch pH is adjusted by the addition of 2 M HCl solution (as needed). The required acidic solution is prepared in a separate suitable vessel by adding concentrated HCl (1.392 kg±5% or 1.18 L±5%) to DI water (6.00 kg±5% or 6.00 L±5%). The pH adjustment typically requires a charge of about 3.5 to about 4.5 L/kg. In certain instances, if the pH drops below about 4.8 (e.g., about 5.0+/−0.2), a solution of 2 M NaOH is added (as needed) to bring the batch pH within the specified 5.0±0.2 range. In certain instances, if needed, the basic solution is prepared in a suitable vessel from NaOH (0.56 kg±5%) and DI water (7.0 kg±5% or 7.0 L±5%).

EDAC [(0.447 kg)±2%, 2.33 mol] is charged to the batch while maintaining a temperature range of 20±5° C. The charging system used for the charge of the EDAC is rinsed with DCM (0.27 kg±5% or 0.20 L±5%) and the rinse is added to the reaction mixture. The mixture is agitated at a reaction temperature of 20±5° C. for about 15 minutes to 6 hours and sampled for reaction completion. In certain embodiments, the mixture is agitated at a reaction temperature of 20±5° C. for no longer than or equal to about 1 hour and sampled for reaction completion. The reaction can be considered complete when the content of Compound 3a relative to Compound 4a is no more than or equal to about 1.0% in area by HPLC analysis (method summarized in Table 4). The pH is checked at each sampling and adjusted as required, maintaining a pH between about 4.8 to about 6.0. In certain instances if needed, HCl or NaOH solutions are added as described above. The first sample is collected after about 15 minutes to 6 hours hold time. In certain embodiments, the first sample is collected after approximately 1 hour hold time. In certain embodiments, additional samples are collected at intervals of approximately 3 hours. If the reaction is not complete after two samples are collected, additional EDAC and Boc-(S)-HABA are charged to complete the reaction according to the following formula: Charge=P3*D3/(100−D3), where: P3=the quantity of EDAC or Boc-(S)-HABA in kg initially charged and D3=the quantity of unconsumed Compound 3a in a/a %.

Once complete, MeOH (1.58 kg±5% or 2.00 L±5%) is charged to the reaction while maintaining a reaction temperature of 20±5° C. DCM (15.94 kg±5% or 12.00 L±5%) is then charged to the reaction while maintaining a batch temperature of 20±5° C. DI water (5.0 kg±5% or 5.0 L±5%) is then charged to the reaction while maintaining a batch temperature of 20±5° C. The pH of the batch is adjusted between about 9.0 and about 10.0 by adding a 2 M NaOH solution (as needed) while maintaining a temperature of 25±5° C. The pH adjustment typically requires a 2 M NaOH charge of about 3.5 to about 4.5 L/kg. If the batch pH exceeds 10.0, a 2 M HCl solution is charged to achieve the specified range. The mixture is agitated at a temperature of about 20° C. to about 38° C. for about 15 minutes to 12 hours. In certain embodiments, the mixture is agitated at a temperature of about 20° C. to about 38° C. for no longer than or equal to about 30 minutes. The contents are then allowed to settle and separate for about 30 minutes to 12 hours. In certain embodiments, the contents are then allowed to settle and separate for at least or equal to about 1 hour. The organic phase (lower phase) is transferred into a receiver and the aqueous phase is discharged for disposal. The product is in the organic phase. The organic phase is charged back to reactor followed by MeOH (2.38 kg±5% or 3.00 L±5%), while maintaining the batch temperature between about 20° C. and about 38° C. DI water (7.0 kg±5% or 7.0 L±5%) is then charged to the mixture and it is agitated at a temperature between about 20° C. and about 38° C. for about 15 minutes to 12 hours. In certain embodiments, DI water (7.0 kg±5% or 7.0 L±5%) is then charged to the mixture and it is agitated at a temperature between about 20° C. and about 38° C. for no longer than or equal to about 30 minutes. The contents are allowed to settle and separate for about 30 minutes to 12 hours. In certain embodiments, the contents are allowed to settle and separate for at least or equal to about 1 hour. The organic phase (lower phase) is transferred into a receiver and the aqueous phase is discharged for disposal. The product is in the organic phase. The batch is concentrated under vacuum at a jacket temperature of no more than or equal to about 40° C. (e.g., 20 to 40° C.) until the residual volume is approximately 10 L±5%.

Part 4: Crystallization of Compound 4a

Acetonitrile (7.87 kg±5% or 10.00 L±5%) is charged to the batch from Part 3 for about 5 minutes to 4 hours. In certain embodiments, acetonitrile (7.87 kg±5% or 10.00 L±5%) is charged to the batch from Part 3 in no less than or equal to about 10 minutes. The mixture is concentrated under vacuum at a jacket temperature of no more than or equal to about 40° C. (e.g., 20 to 40° C.) to give a final residual volume of approximately 10 L±5%. Acetonitrile (7.87 kg±5% or 10.00 L±5%) is charged to the batch and is concentrated under vacuum at a jacket temperature of no more than or equal to about 40° C. (e.g., 20 to 40° C.) to give a final residual volume of approximately 10 L±5%. Acetonitrile (variable quantity) is then charged to achieve a final batch volume of approximately 25 L±5%. The contents of the reactor are a thick opaque slurry of white solids.

The batch is then heated to reflux (~82° C.) and held for about 5 minutes to 12 hours. In certain embodiments, the batch is then heated to reflux (~82° C.) and held for no longer than or equal to about 15 minutes. During the hold period, it is expected that not all of the solids will dissolve. The mixture is charged with DI water (0.375 kg±5% or 0.375 L±5%) while maintaining reflux. The batch is agitated for about 30 to about 60 minutes to achieve a homogeneous solution. If a homogeneous solution is not obtained within about 30-60 minutes, additional portions of DI water (0.125 kg±5% or 0.125 L±5%) are charged to dissolve the remaining solids. Adding more water typically has a minor beneficial effect on quality, but may give a lower yield. Once a homogeneous solution is obtained, the batch is cooled to a temperature of 75±3° C. over about 15 minutes to 12 hours. In certain embodiments, once a homogeneous solution is obtained, the batch is cooled to a temperature of 75±3° C. over no longer than or equal to about 1 hour.

The batch is charged with Compound 4a seed (0.01 kg±2%) while maintaining a temperature of 75±3° C. The seed slurry charge vessel and lines are rinsed with acetonitrile (0.08 kg±5% or 0.10 L±5%) and the rinse is added to the batch. The batch is then agitated for about 15 minutes to 12 hours. In certain embodiments, the batch is then agitated for no less than or equal to about 30 minutes. The batch is cooled to a temperature of 50±5° C. over 30 minutes to 12 hours and held for an additional about 2-12 hours with moderate agitation to give a thick slurry. In certain embodiments, the batch is cooled to a temperature of 50±5° C. over no less than or equal to about 2 hours and held for an additional about 2-12 hours with moderate agitation to give a thick slurry. The batch is cooled to a temperature range between about −5 and about 5° C. over about 1 to 24 hours and held for an additional about 4-12 hours. In certain embodiments, the batch is cooled to a temperature range between about −5 and about 5° C. over no less than or equal to about 1 hour and held for an additional about 4-12 hours. The batch is filtered and deliquored and the filter cake is washed with 0±5° C. acetonitrile (0.79 kg±5% or 1.00 L±5%) and deliquored.

The product is dried under vacuum at a temperature no more than or equal to about 55° C. (e.g., 0 to 55° C.). The drying is deemed complete when the loss on drying is no more than or equal to about 1% w/w. The product is dried under a sweep of dry nitrogen. Post drying the product may be de-lumped with a suitable sieving operation. The yield over the three steps from sisomicin freebase to Compound 4a is about 65%.

A seeded crystallization in acetonitrile with 1.5% DI water at 75±3° C. followed by cooling may be selected because of the high yield of ~70%, high purity of at least or equal to about 88.08% (the purity of the material before crystallization was about 77.75%), and ease of filtering the mixture. However, several crystallization procedures were tested before acetonitrile with 1.5% DI water at 75±3° C. followed by cooling was selected. These are detailed in Table 5. Use of water (about 1.5%) as a cosolvent with acetonitrile may reduce the processing volume required for the crystallization.

TABLE 5

| Crystallization Conditions Tested for Compound 4a | | |
|---|---|---|
| Solvent (v/v) | Conditions[a,b] | Observation |
| EtOH | 20 vols (clear solution at 69° C.). Filtered. Cooled to 55° C. and held 1 hr (clear solution w/solids above liquid line). Scraped down solids. 1 hr hold (thin suspension). Slow cooled to RT. Stirred for 5 days. 59% yield. | Opaque aggregates and fines with no distinct morphology. |
| IPA | 20 vols (thin suspension at 82° C.). Filtered. Cooled to 55° C. and held 1 hr (white slurry). 1 hr hold. Slow cooled to RT. Stirred for 5 days. 56% yield. | Opaque aggregates and fines with no distinct morphology. |
| 2:1 MeOH: water | 15 vols (clear solution with slight haze at 61° C.). Filtered (clear solution). Cooled to 55° C. and held 1 hr (clear solution w/solids above liquid line). Scraped down solids. Cooled to 40° C. and held 1 hr (cloudy suspension). Slow cooled to RT. Stirred for 1 day. 52% yield, 89.07% purity. | Slow filtration; Opaque aggregates and fines with no distinct morphology. |
| 1-PrOH | 20 vols (clear solution at 75° C.). Filtered. Cooled to 55° C. and held 1 hr (clear solution w/solids above liquid line). Scraped down solids. 1 hr hold (thin suspension). Slow cooled to RT. Stirred for 5 days. 71% yield, 92.31% purity. | Opaque aggregates and fines with no distinct morphology. |
| 1-PrOH | 10 vols (clear solution at 89° C.). Filtered. Cooled to 82° C. and held 1 hr (clear solution w/solids above liquid line). Scraped down solids. Seeded with ~1 wt % Compound 4a. 1 hr hold (thick white slurry). Slow cooled to RT. Stirred for 1 day. 81% yield, 91.22% purity. | Slow filtration; Opaque aggregates and fines with no distinct morphology. |
| THF | 20 vols 2% aqueous THF (clear solution at 35° C.). Filtered. Distilled to ~10 vols. Added additional 10 vols of THF. Distilled to ~10 vols (clear solution with solids above liquid line). Solids scraped down and held at ~63° C. (thin suspension). Stirred 30 min. Slow cooled to RT. Stirred for 1 day. 60% yield, 90.36% yield. | Slow filtration; Opaque aggregates and fines with no distinct morphology. |
| 1:1 THF: ACN | 20 vols (clear solution with slight haze at 65° C.). Filtered (clear solution). Cooled to 55° C. and held 1 hr (clear solution w/solids above liquid line). Scraped down solids. Cooled to 40° C. and held 1 hr (cloudy suspension). Slow cooled to RT. Stirred for 1 day. 64% yield. | Opaque aggregates and fines with no distinct morphology. |
| 1:1 THF: heptane | 20 vols THF (clear solution at ~65° C.). Filtered. Distilled to ~7 vols (clear solution w/solids above liquid line). Scraped down solids. Seeded with ~1 wt % Compound 4a. 0.5 hr hold (thin slurry). Slow cooled to RT. Stirred for 2 days (white slurry). Added 10 vols heptane (white slurry). Stirred 1 hour. 87% yield, 90.81% purity. | Opaque aggregates and fines with no distinct morphology. |

TABLE 5-continued

Crystallization Conditions Tested for Compound 4a

| Solvent (v/v) | Conditions[a,b] | Observation |
| --- | --- | --- |
| 1:1 THF: IPAc | 20 vols THF (clear solution at ~65° C.). Filtered. Distilled to ~7 vols (clear solution w/solids above liquid line). Scraped down solids. Seeded with ~1 wt % Compound 4a. 0.5 hr hold (thin slurry). Slow cooled to RT. Stirred for 2 days (white slurry). Add 7 vols IPAc (white slurry). Stirred 1 hour. 76% yield, 92.03% purity. | Opaque aggregates and fines with no distinct morphology. |
| 1:1 THF: IPAc | 10 vols 1% aqueous THF (clear solution at ~54° C.). Filtered. Distilled to ~5 vols (clear solution w/solids above liquid line). Scraped down solids at ~63° C. 0.5 hr hold (thick white slurry). Added 5 vols IPAc. Stirred 1 hr. Slow cooled to RT. Stirred for 1 day (white slurry). 78% yield. | Slow filtration; Opaque aggregates and fines with no distinct morphology. |
| 2:3 THF: water | 20 vols (thin suspension at 65° C.). Filtered (oiling). Cooled to 55° C. and held 1 hr (milky suspension). Cooled to 40° C. and held 1 hr. Milky solution (formed 2 layers upon standing) Slow cooled to RT. Stirred for 1 day (sticky gel and cloudy solution). Sonicated. Stirred 5 hours. | Sticky, gummy mass |
| 5% aqueous 1-PrOH | 20 vols 5% aqueous 1-PrOH (clear solution at 54° C.). Filtered. Distilled to ~10 vols. Cooled to 85° C. and seeded (dissolved). Cooled to 79° C. and seeded (dissolved). Cooled to 71° C. and seeded with Compound 4a (thin suspension). Stirred 30 min. Slow cooled to RT. Stirred 1 day (white slurry). 50% yield, 85.81% purity. | Slow filtration. Aggregates and fines. |
| 10 vols 1-PrOH | 10 vols 1-PrOH (slightly hazy solution at 90° C.). Filtered. Cooled to 85° C. and seeded (dissolved), Cooled to 79° C. and seeded with Compound 4a (thin suspension). Stirred 30 min. Cooled to 71° C. and held 30 min. Slow cooled to RT. Stirred 1 day (white slurry). 53% yield. | Slow filtration. Aggregates and fines with no distinct morphology. |
| Aqueous ACN | 20 vols. of 1% aqueous ACN seeded at 75° C. The mixture was filtered and cooled to the specified seeding temperature after being heated to ~80° C. ~1 wt % of Compound 4a was used for seeding. The mixture was allowed to slow cool to RT and stirred overnight before solids were isolated. ~70% yield, 88.08% purity. | Opaque aggregates and fines with no distinct morphology. |
| Aqueous ACN | 20 vols. of 1% aqueous ACN seeded at 70° C. The mixture was filtered and cooled to the specified seeding temperature after being heated to ~80° C. ~1 wt % of Compound 4a was used for seeding. The mixture was allowed to slow cool to RT and stirred overnight before solids were isolated. ~69% yield. | Opaque aggregates and fines with no distinct morphology. |
| Aqueous ACN | 20 vols. of 1% aqueous ACN seeded at 65° C. The mixture was filtered and cooled to the specified seeding temperature after being heated to ~80° C. ~1 wt % of Compound 4a was used for seeding. The mixture was allowed to slow cool to RT and stirred overnight before solids were isolated. ~67% yield. | Opaque aggregates and fines with no distinct morphology. |
| Aqueous ACN | 20 vols. of 1% aqueous ACN heated to 75° C. (unseeded). The mixture was filtered and cooled to the specified seeding temperature after being heated to ~80° C. The mixture was allowed to slow cool to RT and stirred overnight. Precipitation was observed at ~54° C. and the slurry produced from initial precipitation was not very mobile. ~67% yield, 88.96% purity. | Opaque aggregates and fines with no distinct morphology. |

[a]The purity of the material before crystallization was 77.75%.
[b]All concentrations, temperatures, yields (by total mass), and times reported are approximate.

Part 5: Characterization Data for Compound 4a

Figure 3:
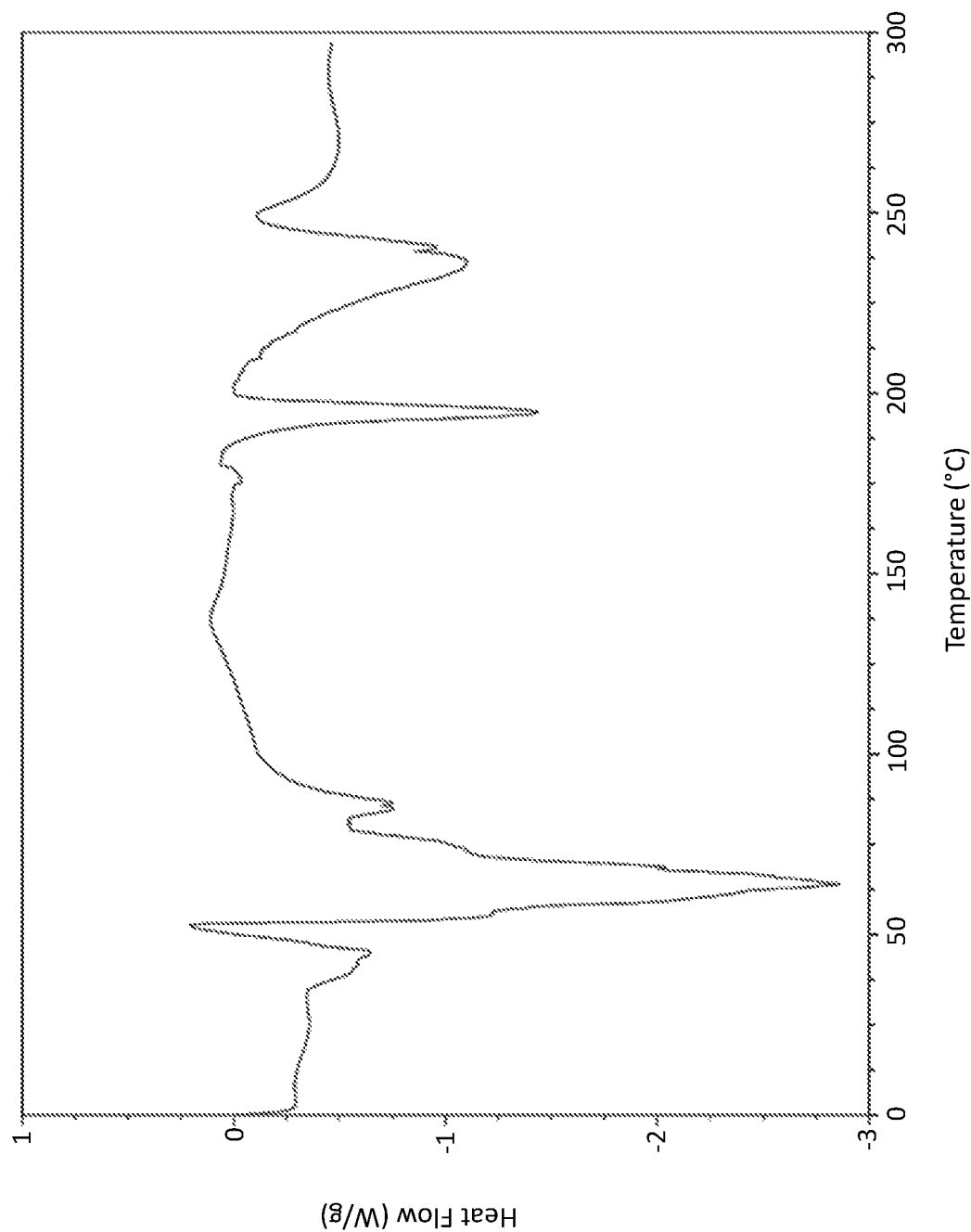

The XRPD spectrum of Compound 4a is shown in FIG. 1. TGA of Compound 4a was consistent with an anhydrous/non-solvated material, as there was only a 0.1 wt % change from 25 to 189° C., suggesting a low volatile content (FIG. 2). The DSC profile of Compound 4a is shown in FIG. 3.

Example 2—Synthetic Protocol for Compound 6a

Detailed below is a general synthetic protocol for Compound 6a.

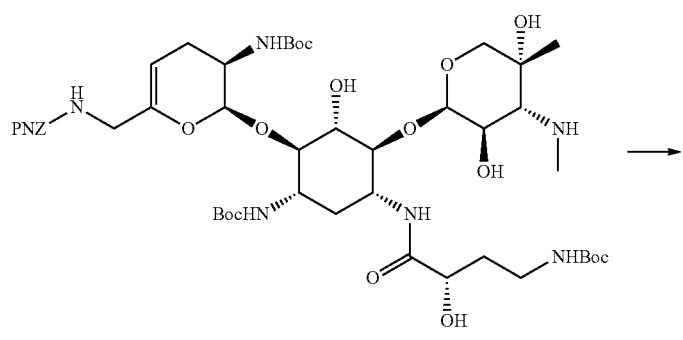

4a

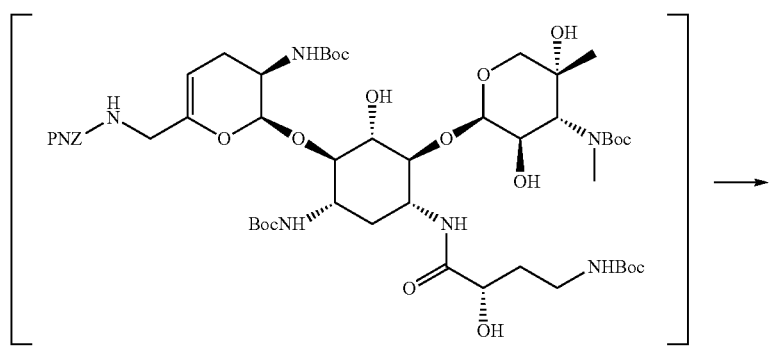

5a

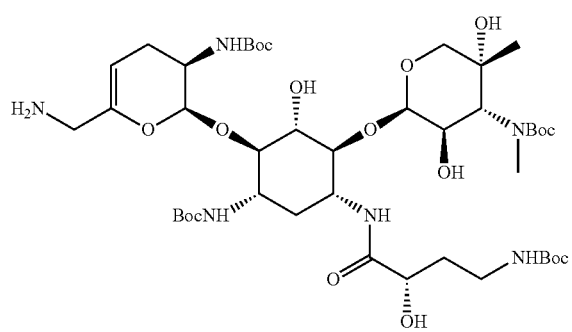

6a

Part 1: Synthesis of Compound 5a

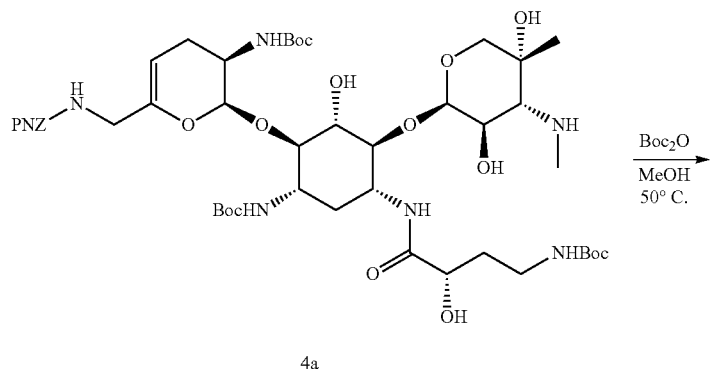

4a

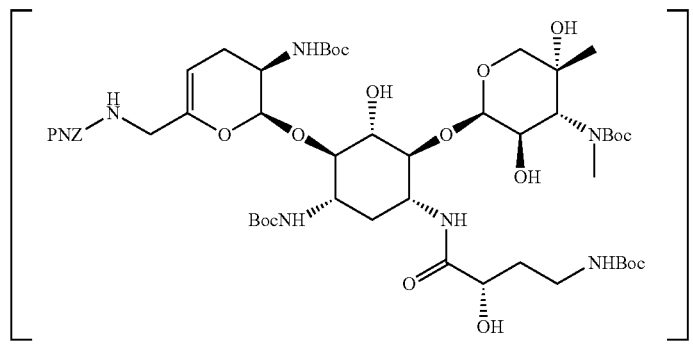

5a

Compound 4a (1.0 kg±1%) and MeOH (7.92 kg±5% or 10.00 L±5%) are charged into a reactor. The mixture is heated to a temperature of 50±5° C. A solution of Boc$_2$O (0.255 kg±2%) in methanol (0.20 kg±5% or 0.25 L±5%) is added to the reactor while maintaining the temperature of 50±5° C. The charging system used for the charge of the Boc$_2$O solution with methanol (0.20 kg±5% or 0.25 L±5%) is rinsed and the rinse is added to the reaction mixture while maintaining the temperature between 50±5° C. The batch is held at 50±5° C. until reaction completion. The reaction can be considered complete when the content of Compound 4a is lower than, or equal to, about 3.0% in area by HPLC (see Table 6 for the HPLC method used). The first sample for analysis is collected after about 15 minutes to 12 hours of reaction time. In certain embodiments, the first sample for analysis is collected after 3 hours of reaction time and subsequent samples, if required, are collected at about 3 hour intervals. If required to complete the reaction, additional Boc$_2$O in methanol solution is added to the reaction mixture. The addition quantity is calculated according to the following formula: Charge=P1×(A2/[100−A2])±1%, where: P1=the quantity of Boc$_2$O (kg) charged earlier in the reaction and A2=the quantity of unconsumed Compound 4a in a/a % in the last sample.

Once the reaction is complete, the batch is stabilized to 20±5° C. The batch can be held at this temperature range for up to about 55 hours (e.g., 0 to 55 hours).

TABLE 6

HPLC Method for Parts 1 and 2 of Example 2

| Column | Waters X-Bridge C18, 3.5 μm 150 mm × 4.6 mm |
|---|---|
| Column Temperature | 40° C. |
| Flow Rate | 1.2 mL/min |
| Detection Wavelength | 210 nm |
| Mobile Phases | 0.25 M NH$_4$OH in water |
| | 0.25 M NH$_4$OH in acetonitrile |
| Gradient | Time (min) % Mobile Phase A % Mobile Phase B |
| | 0.00 70 30 |
| | 28.0 35 65 |
| | 30.0 35 65 |
| | 30.1 70 30 |
| | 40.0 70 30 |
| Run Time | 40 min |
| Injection Volume | 20 μL |

Part 2: Synthesis of Compound 6a

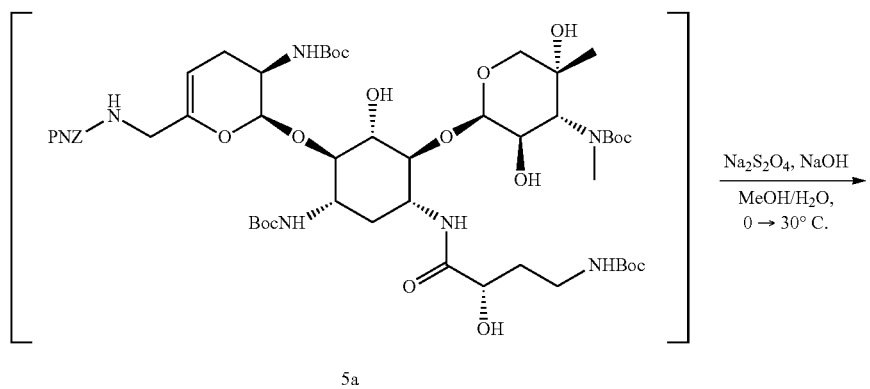

5a

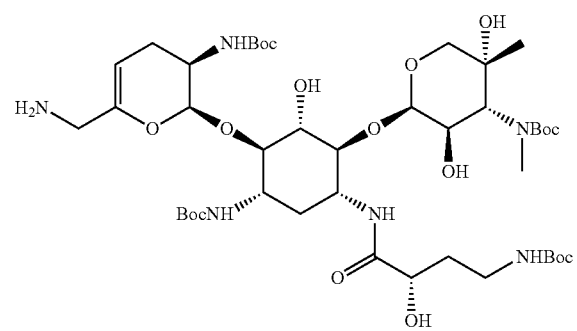

6a

Deionized water (7.78 kg±5% or 7.78 L±5%) is charged into a reactor and solid sodium hydroxide (0.39 kg±1%) is added followed by agitation until visually dissolved. Part of the deionized water may be charged after the charge of sodium hydroxide and/or after the charge of the sodium dithionite and used to rinse the charging device used for the charge of these materials. The temperature is stabilized to about 0-5° C. Sodium dithionite (1.196 kg±1%) is added to the basic aqueous solution while maintaining the temperature of the solution at between about 0° C. and about 5° C. Higher temperatures during the addition may afford lower product purity. The mixture is agitated for about 5 minutes to 12 hours at about 0-5° C. In certain embodiments, the mixture is agitated for not longer than or equal to about 15 minutes at about 0-5° C. The dithionite solution should be used within about 0 to 4 hours of the $Na_2S_2O_4$ charge. In certain embodiments, the dithionite solution should be used within about 90 minutes of the $Na_2S_2O_4$ charge.

The reaction mixture from Part 1 is added to the basic sodium dithionite solution over about 1-8 hours (e.g., 1-4 hours), while maintaining the temperature of the mixture below about −5° C. to below about 15° C. In certain embodiments, the reaction mixture from Part 1 is added to the basic sodium dithionite solution over about 1-4 hours, while maintaining the temperature of the mixture below about 10° C. The addition is exothermic and faster additions provide gummy solids. The charging system used for the charge of the reaction mixture is rinsed with methanol (0.40 kg±5% or 0.50 L±5%) and the rinse is added to the batch. The batch is heated to a temperature between about 25° C. and about 30° C. over a period of about 1 to 4 hours. In certain embodiments, the batch is heated to a temperature between about 25° C. and about 30° C. over a period of about 2 hours. Typically, a maximum jacket temperature is about 25 to 35° C. and a ΔT between the jacket and the batch temperature of not more than or equal to about 10° C. (e.g., 0 to 10° C.) is maintained. In certain embodiments, a maximum jacket temperature is about 30° C. and a ΔT between the jacket and the batch temperature of not more than or equal to about 10° C. is maintained. The batch is agitated at a temperature of about 25-30° C. until reaction completion. Higher reaction temperatures may lead to higher amounts of impurities.

The reaction is deemed complete when the content of the peak with relative retention time of 0.43:

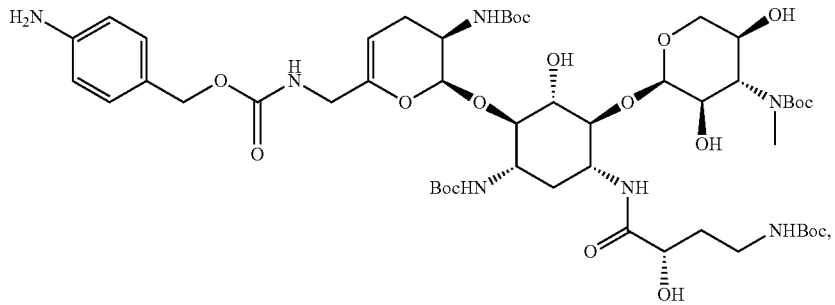

is lower than, or equal to, about 3.0% a/a by HPLC (same method as that detailed in Table 6). In certain embodiments, The first sample is taken at the end of the heating period and subsequent samples are taken in about 3 hour intervals.

Once the reaction is complete, the mixture is distilled under vacuum at a jacket temperature of about 20 to 40° C. until a final volume of 13 L±5%. In certain embodiments, once the reaction is complete, the mixture is distilled under vacuum at a jacket temperature of not more than or equal to about 35° C. until a final volume of 13 L±5%. IPAc (3.49 kg±5% or 4.00 L±5%) is charged to the batch while maintaining the temperature between about 25-40° C. Deionized water (7.0 kg±5% or 7.0 L±5%) is then charged to the batch while maintaining the temperature between about 25-40° C. The mixture is agitated for about 15 minutes to 12 hours at a temperature of about 30-40° C. In certain embodiments, the mixture is agitated for not less than or equal to about 20 minutes at a temperature of about 30-40° C. Complete dissolution of the salts is not required as long as the phase separation could proceed without problems with the presence of some undissolved salts.

Agitation is halted and the layers allowed to separate for about 30 minutes to 12 hours. In certain embodiments, agitation is halted and the layers allowed to separate for not less than or equal to about 1 hour. The aqueous phase (aqueous phase 1) is transferred into a receiver. The product rich organic phase (organic phase 1) is transferred into another receiver. IPAc (1.74 kg±5% or 2.00 L±5%) is charged to aqueous phase 1, maintaining the temperature between about 25-40° C. The mixture is agitated for about 15 minutes to 12 hours at a temperature of 35±5° C. In certain embodiments, the mixture is agitated for not less than or equal to about 20 minutes at a temperature of 35±5° C. Salts may precipitate below about 30° C. Agitation is halted and the layers are allowed to separate for about 30 minutes to 12 hours. In certain embodiments, agitation is halted and the layers are allowed to separate for not less than or equal to about 1 hour. The lower aqueous phase (aqueous phase 2) is sent to waste.

Organic phases 1 and 2 are combined in a suitable receiver. An approximately 6.5% w/w of sodium bicarbonate aqueous solution is prepared by the dissolution of NaHCO$_3$ (0.42 kg±5%) in deionized water (6.00 kg±5% or 6.00 L±5%). The temperature of this solution is stabilized to 25±5° C. Approximately 2 to 6 L of the 6.5% w/w NaHCO$_3$ solution is charged to the combined organic phases. In certain embodiments, approximately 3 L of the 6.5% w/w NaHCO$_3$ solution is charged to the combined organic phases. The solution is agitated for about 15 minutes to 12 hours at a temperature of 25±5° C. In certain embodiments, the solution is agitated for not less than or equal to about 20 minutes at a temperature of 25±5° C. Agitation is then halted and the layers are allowed to separate for about 0 to 48 hours. In certain embodiments, agitation is then halted and the layers are allowed to separate for not less than or equal to about 1 hour. The lower aqueous phase is sent to waste. The organic phase (organic phase 3) may be maintained at not more than or equal to about 25° C. (e.g., 0 to 25° C.) for about 0 to 48 hours In certain embodiments, the lower aqueous phase is sent to waste. The organic phase (organic phase 3) may be maintained at not more than or equal to about 25° C. for up to about 24 hours.

Approximately 2 to 6 L of the 6.5% w/w NaHCO$_3$ solution is charged to organic phase 3. In certain embodiments, approximately 3 L of the 6.5% w/w NaHCO$_3$ solution is charged to organic phase 3. The mixture is agitated for about 30 minutes to 12 hours at a temperature of 25±5° C. In certain embodiments, the mixture is agitated for not less than or equal to about 20 minutes at a temperature of 25±5° C. Agitation is then halted and the layers are allowed to separate for not less than or equal to about 1 hour. The lower aqueous phase is discharged to waste. The organic phase (organic phase 4) may be maintained at not more than or equal to about 20 to 25° C. for up to about 24 hours. In certain embodiments, the organic phase (organic phase 4) may be maintained at not more than or equal to about 25° C. for up to about 24 hours.

Organic phase 4 is distilled under vacuum at a jacket temperature of not more than or equal to about 50° C. (e.g., 20 to 50° C.) until a final volume of 3 L±5%. IPAc (2.62 kg±5% or 3.00 L±5%) is charged to the batch. The mixture is distilled under vacuum at a jacket temperature of not more than or equal to about 50° C. (e.g., 20 to 50° C.) until a final volume of 3 L±5%. IPAc (2.62 kg±5% or 3.00 L±5%) is charged to the batch. The mixture is then distilled under vacuum at a jacket temperature of not more than or equal to about 50° C. (e.g., 20 to 50° C.) until a final volume of 4.5 L±5%. Deionized water (0.135 kg±5% or 0.135 L±5%) is then charged to the batch while maintaining the temperature between about 35-40° C. The temperature of the batch is adjusted to between about 15 and about 30° C. DCM (5.98 kg±5% or 4.50 L±5%) is charged to the batch while maintaining a temperature of about 15-30° C. In some cases, the mixture is turbid even though full dissolution of the Compound 6a was achieved.

The Compound 6a seed (0.02 kg±2%) is charged to the batch solution while maintaining a temperature of about 20-25° C. Crystallization is observed, however, the rate of crystallization may be slow. The mixture is stirred at a temperature between about 20-25° C. over about 1-2 hours and a slurry appears. If no slurry is observed, the mixture is cooled to a temperature between about 15-20° C. and an additional Compound 6a seed (0.02 kg±2%) is added to the batch solution while maintaining a temperature of about 15-20° C., for about 1 to about 2 hours. A slurry then appears. Lower temperatures during and after seeding may give lower purities but higher yields.

The batch is cooled to about 15-25° C. and agitated at this temperature range for approximately 18-24 hours. The batch is cooled to a temperature between about 5° C. and about −5° C. over about 1 to 12 hours and held at this temperature range with agitation for about 6-12 hours. In certain embodiments, the batch is cooled to a temperature between about 5° C. and about −5° C. over about 2 hours and held at this temperature range with agitation for about 6-12 hours. This aging time is important to the yield. The batch is discharged to a suitable filter and deliquored. The wetcake is washed with an approximately 5° C. to −5° C. solution of DCM (1.33 kg±5% or 1.00 L±5%) and subsequently deliquored. The product is dried under vacuum at not more than or equal to about 45° C. (e.g., 0 to 45° C.). The drying is complete when the loss on drying is not more than or equal to about 1% w/w. The product may be dried under vacuum with a nitrogen sweep. The product may be sieved after the drying operation. The yield over the two steps from Compound 4a to Compound 6a is about 85%. Tightening some of the variables, such as the final volume of distillation, DCM quantity, water content, seeding and aging temperature, and aging times after seeding, may provide a typical crystallization with typical purity results. Water may have an impact on the yield, but appears to have no relationship to product quality.

Part 3: Optimization of Crystallization Conditions for Compound 6a

The solubility of Compound 6a in dichloromethane/isopropyl acetate (50/50 v/v) with about 1% water, isopropyl acetate/dichloromethane (71/29 v/v) with about 2% water, and isopropyl acetate/dichloromethane (71/29 v/v) with about 8% water exhibits a strong dependence on temperature. At elevated temperatures, limited solubility may be observed in dichloromethane/isopropyl acetate (50/50 v/v) with about 1% water, and intermediate solubility may be observed in isopropyl acetate/dichloromethane (71/29 v/v) with about 2% water and isopropyl acetate/dichloromethane (71/29 v/v) with 8% water. Cloud points all occur once the reactor reaches the lowest temperatures of approximately 6-8° C., possibly indicative of a large metastable zone width under all conditions. At about 7.9 mg/mL in dichloromethane/isopropyl acetate (50/50 v/v) with about 1% water, cloud points do not occur until approximately 3 and 8 hours at about 6-8° C. These results may indicate that without the use of seeding, inconsistencies may be expected in terms of the timing of the main nucleation event (spontaneous nucleation). Additionally, nucleation consistently occurs at high supersaturation levels, sometimes resulting in poor crystallinity, crystal defects such as solvent inclusions, and/or formation of small particles.

Selected samples from each solvent system from the solubility and metastable zone width determination experiments are isolated by vacuum filtration. No filtration issues are noted when isolating solids from dichloromethane/isopropyl acetate (50/50 v/v) with about 1% water. However, sticky solids and some deliquescence are observed from solids isolated from isopropyl acetate/dichloromethane (71/29 v/v) with both about 2% and about 8% water. The material isolated from dichloromethane/isopropyl acetate (50/50 v/v) with about 1% water is crystalline. The material isolated from isopropyl acetate/dichloromethane (71/29 v/v) with about 2% water is disordered, and the material isolated from isopropyl acetate/dichloromethane (71/29 v/v) with about 8% water may contain a small amount of x-ray amorphous material.

Part 4: Characterization Data for Compound 6a

The XRPD spectrum of Compound 6a is shown in FIG. 4 and the peak positions are substantially in accordance with those listed in Table 1. TGA of Compound 6a indicated 4.5 wt % loss between 24.1-78.6° C. (FIG. 5). The main exothermic event in the DSC of Compound 6a occurred with a left limit temperature of 231.8° C. and energy of −52.9 kJ/kg (FIG. 6).

Example 3: Synthetic Protocol for Compound 7a

Detailed below is a general synthetic protocol for Compound 7a.

Part 1: Synthesis of Compound 7a

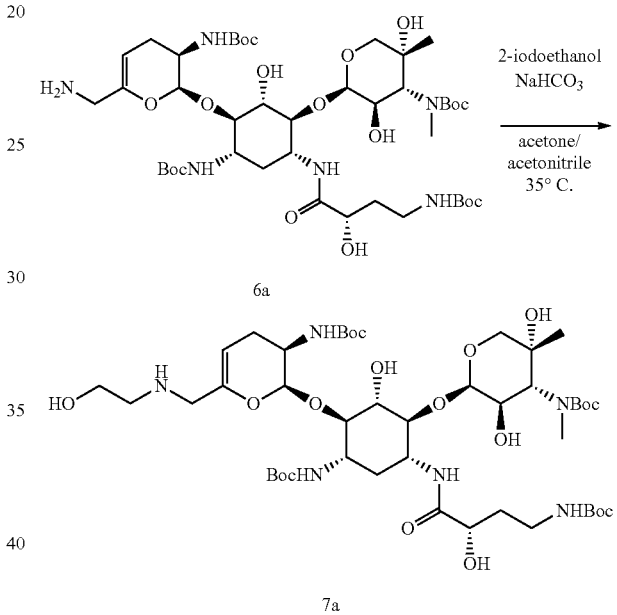

Compound 6a (1.0 kg±1%) and acetonitrile (3.94 kg±5%< >5.00 L±5%) are charged into the reactor. The temperature is stabilized at between about 15° C. to about 30° C. with stirring. The solution may be turbid. The mixture is distilled under vacuum at a maximum temperature of about 45° C. (e.g., 20 to 45° C.) until a final volume of 2 L±5%.

A sample is taken for determination of the water content by Karl Fischer. If the water content is lower than, or equal to, about 0.30% w/w, the reaction proceeds to the next step. Otherwise, acetonitrile (2.36 kg±5%< >3.00 L±5%) is charged into the reactor and the distillation is repeated until the content of water in the solution after the distillation is lower than, or equal to, about 0.30% w/w by Karl Fischer.

The reaction mixture is cooled to a temperature between about 30° C. and about 15° C. and acetone (3.94 kg±5%< >5.00 L±5%) is charged into the reactor. Note, part of the acetone may be charged after the sodium bicarbonate and/or 2-iodoethanol charges and used to rinse the charging system used for these charges.

The reaction mixture is heated to a temperature between about 33° C. and about 37° C., with a target of about 35° C. Sodium bicarbonate (0.177 kg±2%) is charged to the reactor while maintaining the temperature of the reaction mixture between about 33° C. and about 37° C., with a target of about 35° C. 2-Iodoethanol (0.226 kg±2%< >0.102 L±2%) is charged to the reaction mixture, while maintaining the temperature of the reaction mixture at between about 33° C. and about 37° C., with a target of about 35° C. The reaction mixture is stirred at a temperature between about 33° C. and about 37° C., with a target of about 35° C., until the content of Compound 6a relative to Compound 7a was lower than, or equal to, about 2.5% in area by HPLC. If required to complete the reaction, additional 2-iodoethanol is added to the reaction mixture. The quantity of additional 2-iodoethanol in kg is calculated using the following formula: [P2×D/(100-D)]±2%, where: P2 is the quantity of 2-iodoethanol in kg charged initially in the reaction and D is the content of unconsumed Compound 6a in % area by HPLC in the last in-process control sample. Area percent is determined by HPLC-UV: Zorbax SB-CN, 3.5 µm, 150×4.6 mm, A: 25 mM $K_2HPO_4$; B: acetonitrile. Gradient: 5-80% B in 25 minutes, hold for 5 minutes; re-equilibrate for 5 minutes, flow rate: 1.0 mL/min, UV: 210 nm, column temp: 30° C.

Once complete, the reaction mixture is cooled to a temperature between about 25° C. and about 20° C. 1,4-Diazabicyclo[2.2.2]octane (DABCO, 0.24 kg±2%) is charged to the reaction mixture while maintaining the temperature between about 20° C. and about 25° C. and is stirred at this temperature range until the content of 2-iodoethanol by GC is lower than the loss on drying of the method (<0.003% w/w). The GC method uses a 50 cm DB-1 column with an I.D. of 0.32 mm. The initial oven temperature is about 70° C. with a hold of about 1 minute followed by a ramp of about 10° C./minute to about 250° C.). Deionized water (5.00 kg±5%< >5.00 L±5%) is added to the mixture, maintaining the temperature between about 15° C. and about 30° C. This addition is exothermic. Isopropyl acetate (4.36 kg±5%< >5.00 L±5%) is added while maintaining the temperature between about 15° C. and about 30° C. and the mixture is stirred for about 5 minutes to 12 hours at a temperature between about 15° C. and about 30° C. In certain embodiments, isopropyl acetate (4.36 kg±5%< >5.00 L±5%) is added while maintaining the temperature between about 15° C. and about 30° C. and the mixture is stirred not less than or equal to about 20 minutes at a temperature between about 15° C. and about 30° C. Stirring is then stopped and the layers are allowed to separate for about 30 minutes to 12 hours. In certain embodiments, stirring is then stopped and the layers are allowed to separate for at least or equal to about 30 minutes. The aqueous phase 1 (lower phase) is discharged and organic phase 1 is discharged into a receiver. The product is in the organic phase.

Isopropyl acetate (2.62 kg±5%< >3.00 L±5%) is added to aqueous phase 1 and the mixture is stirred for about 15 minutes of 12 hours at a temperature between about 15° C. and about 30° C. In certain embodiments, isopropyl acetate (2.62 kg±5%< >3.00 L±5%) is added to aqueous phase 1 and the mixture is stirred not less than or equal to about 20 minutes at a temperature between about 15° C. and about 30° C. Stirring is stopped and the layers are allowed to separate for at least or equal to about 30 minutes (e.g., 30 minutes to 12 hours). The aqueous phase 2 (lower phase) is discharged for disposal. Organic phase 2 is discharged into a receiver. The product is in the organic phase and organic phases 1 and 2 are combined.

An aqueous sodium chloride solution is prepared by the dissolution of sodium chloride (technical) (2.00 kg±1%) in deionized water (5.80 kg±5%< >5.80 L±5%). About 2 to 6 L of the aqueous solution of sodium chloride is charged to the combined organic phases and the mixture is stirred for about 15 minutes to 12 hours at a temperature between about 15° C. and about 30° C. In certain embodiments, about 3 L of the aqueous solution of sodium chloride is charged to the combined organic phases and the mixture is stirred not less than or equal to about 20 minutes at a temperature between about 15° C. and about 30° C. Stirring is stopped and the layers are allowed to separate for about 15 minutes to 12 hours. In certain embodiments, stirring is stopped and the layers are allowed to separate for at least or equal to about 30 minutes. The aqueous phase 3 (lower phase) is discharged for disposal. Organic phase 3 containing the product is discharged into a receiver.

About 2 to 6 L of the aqueous solution of sodium chloride is charged to the combined organic phases and the mixture is stirred for about 15 minutes to 12 hours at a temperature between about 15° C. and about 30° C. In certain embodiments, about 3 L of the aqueous solution of sodium chloride is charged to the combined organic phases and the mixture is stirred not less than or equal to about 20 minutes at a temperature between about 15° C. and about 30° C. Stirring is stopped and the layers are allowed to separate for at least or equal to about 30 minutes (e.g., 30 minutes to 12 hours). The aqueous phase 4 (lower phase) is discharged for disposal. Organic phase 4 containing the product is discharged into a receiver.

The organic phase is distilled under vacuum at a maximum jacket temperature of about 20-50° C. (e.g., 50° C.) until a final volume of 2 L±5%. Acetonitrile (8.03 kg±5%< >10.20 L±5%) is charged to the mixture and the mixture is distilled under vacuum at a maximum jacket temperature of about 20-50° C. (e.g., 50° C.) until a final volume of 7.2 L±5%. Isopropyl acetate (0.70 kg±5%< >0.80 L±5%) and deionized water (0.095 kg±2%< >0.095 L±2%) are charged to the solution and the solution is heated to a temperature between about 70° C. and about 80° C. to ensure total dissolution of Compound 7a.

The Compound 7a solution is cooled to a temperature between about 65° C. and about 60° C. If crystallization occurs before addition of the seeds, the mixture may be heated again to a temperature between about 70° C. and about 80° C. until complete dissolution. Before the addition of the seed, the mixture is cooled to a temperature between about 65° C. and about 60° C. Compound 7a seeds (0.02 kg±5% kg) are charged to the Compound 7a solution while maintaining the temperature between about 60° C. and about 65° C. The charging system used for the charge of the Compound 7a seed is rinsed with acetonitrile (0.04 kg±5%< >0.05 L±5%) and the rinse is added to the reaction mixture. The mixture is stirred at a temperature between about 60° C. and about 65° C. for about 4 to about 6 hours. A very thick suspension formed.

The mixture is cooled to a temperature between about 5° C. and about 0° C. over about 12 hours and is stirred at this temperature range for about 1 to about 2 hours. The target cooling rate is about 5-10° C./hour. The product is filtered and washed with acetonitrile (2.83 kg±5%< >3.60 L±5%) previously cooled to a temperature between about 0° C. and about 5° C. The product is then dried, under vacuum, at a temperature lower than, or equal to, about 45° C. (e.g., 0 to 45° C.) until the loss on drying is lower than, or equal to, about 1% w/w. The product is dried with a nitrogen sweep. The product may be sieved during or after the drying. The yield of Compound 7a is about 90%.

Part 2: Optimization of the 6' Amine Alkylation with Haloethanol

Several conditions for the 6' amino alkylation were tested before selecting azeotropic distillation of ACN followed by addition of acetone, 2-iodoethanol, and sodium bicarbonate, and use of DABCO to quench the reaction.

Two approaches were initially investigated to alkylate the 6' amine with haloethanol. In the first approach, the 6' amine was activated using o-nitro benzene sulfonyl chloride (nosyl-Cl) to afford the corresponding 6' amino nosylate. The subsequent alkylation of the nosylate using 2-iodo- or 2-bromoethanol, with or without TBDMS hydroxyl protection, was not optimal and was little improved by changes in solvent (e.g., THF, ACN, or DMF), base (e.g., DIPEA or $K_2CO_3$) and temperature (e.g., ambient to about 80° C.). The second approach, direct 6' amine alkylation using 2-bromoethanol in the presence of NaI and $Na_2CO_3$ at ambient temperature possibly provided a more complete conversion and a cleaner crude product. The 2-bromoethanol, sodium iodide, and sodium carbonate conditions were selected for further evaluation and development.

Between about 2 and about 3 molar equivalents of 2-bromoethanol were found to improve the reaction conditions, with slightly less dialkylated by-product formed at about 2 equivalents. The range of conversion was about 51-68%, with about 1-2 equivalents of NaI required to achieve >65% conversion. However, bromoethanol and sodium iodide were identified as possible significant contributors of water to the reaction mixture. Water in the reaction mixture was not optimal to the outcome and was possibly correlated with higher levels of the dialkylated by-product. Compound 6a also potentially contributed significant water to the batch, but this could be removed by azeotropic distillation using acetonitrile. Other azeotropic solvents were potentially less effective, such as ethanol, or later impacted product precipitation (isopropanol). Acetone was identified as a possible preferred solvent for the alkylation reaction. The intermediacy of a potential acetone iminium species, which, while not being limited by theory, may have prevented over alkylation, was postulated on the basis of LC/MS evidence. While not being limited by theory, it is possible that water in the batch inhibited the formation of or destabilized this postulated imine, which enabled formation of the dialkylated by-product. While not being limited by theory, the role of sodium carbonate as drying agent may be significant as it afforded higher yields than lithium carbonate, potassium carbonate, cesium carbonate, sodium bicarbonate, sodium sulfate, sodium phosphate, and DIPEA. A reaction temperature of about 35° C., compared to about −10° C., about 0° C., and about 23° C., provided the greatest relative extent of conversion with the least relative amount of dialkylated by-product. Higher reaction temperatures (e.g., about 50° C.) may lead to formation of more dialkylated by-product.

However, because bromoethanol and sodium iodide were potentially the chief contributors of water in the reaction mixture, leading to by-product formation, and were used to generate 2-iodoethanol in situ, 2-iodoethanol was also tested. Bromoethanol also afforded a much slower reaction than 2-iodoethanol. The use of about 1.2 molar equivalents of 2-iodoethanol in acetone was sufficient to afford an approximately 86% yield of Compound 7a in about 24 hours at about 35° C., with only about 2% of Compound 6a and about 2.6% of the dialkylated impurity. The use of about 1.1 molar equivalents of 2-iodoethanol afforded an approximately 83% yield of Compound 7a, with about 6.9% Compound 6a and about 1.5% dialkylated impurity and the use of about 1.5 molar equivalents of 2-iodoethanol afforded an approximately 87% yield of Compound 7a, with about 1.9% Compound 6a and about 2.3% dialkylated impurity. Longer reaction times (about 41 or about 48 hours) may cause a decrease of Compound 7a with no further consumption of Compound 6a. $NaHCO_3$ was tested as the base for the reaction and may be preferred over $Na_2CO_3$, $Na_2SO_4$, trimethylamine, trimethyl orthoformate, and hexamethyldisilazane. $Na_2CO_3$ resulted in a relatively higher terminal pH and higher amounts of dialkylated by-product at the end of the reaction as compared with $NaHCO_3$ and $Na_2SO_4$, and $Na_2SO_4$ resulted in the appearance of a new impurity in the isolated product. DABCO may be the preferred quench agent for excess 2-iodoethanol as the other scavengers tested, such as dimethylamine, trimethylamine, diethanolamine, aqueous sodium hydroxide, DBU, cysteine, and MeOH, showed an increase in dialkylated by-product of about 63-1030% between the in-process and isolated product levels, suggesting that residual 2-iodoethanol may not have been destroyed.

It was found that azeotropic drying of Compound 6a in about 5 volumes of ACN worked well for the amine alkylation reaction using acetone, 2-iodoethanol, and sodium bicarbonate followed by DABCO to quench the reaction. The combined condition of about 5 volumes of acetone, $NaHCO_3$, and the about 1.2 molar equivalents of 2-iodoethanol with an approximately 20 to 40° C. reaction temperature achieved <2% Compound 6a with low levels dialkylated by-product. In certain embodiments, the combined condition of about 5 volumes of acetone, $NaHCO_3$, and the about 1.2 molar equivalents of 2-iodoethanol with an approximately 35° C. reaction temperature achieved <2% Compound 6a with low levels dialkylated by-product. Further, it was found that the quality of Compound 7a prepared using a simplified workup with brine and no acid and base extractions may be superior than a lengthier work-up with acid and base extractions. Also, the replacement of water washes with brine washes was correlated with an approximately 15 percentage point increase in molar yield with no loss of product quality.

Part 3: Optimization of Crystallization Conditions for Compound 7a

Several crystallization procedures were tested before crystallization of crude Compound 7a from about 8 volumes of 10% v/v IPAc/ACN doped with about 0.75-2% w/w water with seeding was selected (see Tables 7-11). Additionally, a long hold time at seeding temperature (>2 hours at between about 60° C. and about 65° C.) and a slow cooling ramp (about 60° C. down to about 0° C. at about 5-10° C./h) may be best to get a mobile slurry. This procedure substantially purge unreacted Compound 6a, a penta-Boc impurity (about 63% purge combined), and the dialkylated by-product (about 36% purge), and may afford readily filterable and washable solid product. The deliquoring properties of crystalline Compound 7a from IPAc/ACN may improve removal of impurities in the mother liquors as the product afforded needle-like or rod-like crystals. In contrast, experiments with IPAc and n-heptane produced an amorphous material that filtered and deliquored slowly, leaving impurities in the product.

TABLE 7

Early Crystallization Attempts for Compound 7a (Not Seeded)

| Scale (g) | Solvent system | Vol | Temp °C. | Time to initiate/total | % recovery | % Purity Compound 7a$^a$ (Compound 6a) |
|---|---|---|---|---|---|---|
| 1 | ACN | 2$^a$ | RT | 0.4 h/1 h | 83 | 91 (88) |
| 1 | ACN | 5$^a$ | RT | 0.5 h/2 h | 80 | 93 (88) |
| 0.5 | ACN | 10$^a$ | RT | 1 h/18 h | 77 | 94 (88) |
| 5 | ACN | 10$^a$ | RT | 1.5 h/22 h | 76 | 92.5 (87) |
| 1 | ACN | 10$^a$ | RT | 0.5 h/17 h | 87 | 98 (92) |
| 1 | ACN | 10$^a$ | RT | 1 h/18 h | 64 | 91 (76) |
| 1 | ACN | 20 | RT | 2 h/17 h | 68 | 95 (87) |

$^a$Thick, un-stirrable slurry. Added additional solvent (generally 5 volumes) to enable filtering.

TABLE 8

Crystallizations Using Different Solvent/Antisolvent Combinations

| Mass (g) | Solvent(s) | Vol (mL) | Temp °C. | Time to initiate/total | Seeded yes/no | Recovery (%) | % Purity Compound 7a (Compound 6a) |
|---|---|---|---|---|---|---|---|
| 1 | ACN | 20 | RT | 2 h/4 h/15 h | yes$^e$ | 68 | 96 (87) |
| 1 | 5:95 IPA/H$_2$O$^a$ | 20 | 60 | 48 h | slurry | 78 | 91 (87) |
| 1 | 10:1 ACN/IPAC | 11 | RT | 2/72 | yes | 64 | — (87) |
| 1 | 1:1 ACN/heptane$^b$ | 20$^a$ | 60 to RT | 18 h | no | 67 | 95 (87) |
| 58 | ACN | 20 | RT | 6.5/72 | yes/no$^d$ | 67 | 96+ (85) |
| 1 | 3:1 ACN/H$_2$O | 10 | RT | — | yes | no solids | — |
| 1 | 1:1 ACN/DIPE | 10$^a$ | RT | >2 h/72 h | yes | 71% | 95 (87) |
| 1 | 1:1 ACN/MTBE | 10 | RT | 18 h | no | 54% | 96 (87) |
| 1 | 10:4 ACN/IPAc | 14 | RT | 1.5 h/24 h | no | 69 | 96 (87) |
| 1 | 3:1 ACN/MTBE$^c$ | 12 | RT | 2 h/24 h | no | 62 | — (87) |

$^a$Slurry $^b$Acetonitrile and heptane are immiscible at RT. $^c$Thick, un-stirrable slurry. Added additional solvent (generally 5 volumes) to enable filtering. $^d$Solid Compound 7a was added, but did not serve as seeds. $^e$Crystallization was allowed to form crystals for 4 h, then heated to near reflux to dissolve solids. The solution was cooled to RT and stirred 15 h before collecting solids. When the crystallization process was cooled slowly, the product obtained had a thin needle-like morphology.

TABLE 9

Larger Scale Seeded Crystallizations Using Various ACN/IPAc Solvent Systems

| Scale (g) | Solvent System | Vol | Temp (°C.) | Time to initiate/total | Seeded yes/no % load | Recovery (%) | % Purity Compound 7a (Compound 6a) |
|---|---|---|---|---|---|---|---|
| 53 | 3:1 ACN/IPAc | 11 | RT | 4 h/72 h | yes | 65 | >96 (85) |
| 1 | 3:1 ACN/IPAc | 20 | 40 | 1 h/24 h | yes | 61 | >96 (86) |
| 10.75 | 3:1 ACN/IPAc | 7.5 (5) | 55 | 2 h/24 h | yes | 75+ | >94 (85) |
| 100 | 3:1 ACN/IPAc | 8 (10) | 55 | 3 h | yes | 47 | 95.8 (84) |
| 2 | ACN | 25 | 65 to RT | 24 h | form seed | — | — |
| 52 | 3:1 ACN/IPAc | 10 | 40-0 | 1/26 | 4% | 71.5 | 95 (84) |
| 52 | 100% ACN | 10 | 40-0 | 1.5/26 | 4% | 75 | 95.8 (85) |
| 1 | DCM | 10 | RT-0 | 24/72 | no | 50 | 93 (87) |
| — | ACN | — | 65-RT | 3 d | no | na | 90 |
| 2 | ACN | 10-25 | 65-RT | 3 h/96 | form seed | — | — |
| 52.7 | 9:1 ACN/IPAc | 10 | 40-0 | 2/26 | 4% | 73.2 | 95.9 (84.6) |
| 1 | ACN | 25 | RT | 3 d | form seed | — | — |
| 13.2 | ACN | 10 | 40-0 | 2/24 | ~4% | 76.8 | 95.5 (84.6) |
| 1.25 | ACN | 10-25 | 65-30 | 3/24 | form seed | — | — |
| 1.25 | ACN | 25 | RT | slurry | form seed | — | — |

(a) Solid mass in 1L reactor.

TABLE 10

Seeded Crystallizations with the Water Content Adjusted to 0.5-1%

| Scale (g) | ACN/IPAc ratio v/v | Vol | Temp °C. | Time to initiate/total | Seed Load (%) | Recovery (%) | % Purity Compound 7a (Compound 6a) |
|---|---|---|---|---|---|---|---|
| 8.2 | 9:1$^a$ | 8 | 55-0 | 0.5/26 | 2% | 94.3 | 97.5 (94.8) |
| 63 | 9:1$^a$ | 8 | 55-0 | 0.5/26 | 1.6% | 81.1 | 93.1 (84.3) |
| 51 | 9:1$^a$ | 9 | 55-0 | 0.5/26 | 2%$^d$ | 82.3 | 93.9 (85.1) |
| 5 | 9:1$^b$ | 8 | 50-0 | 0.5 | not seeded | 79 | 94 (87.2) |
| 48 | 9:1$^a$ | 9 | 70-0$^d$ | 0.25 | 1%$^e$ | 94.3 | 97.1 (95.4) |

TABLE 10-continued

Seeded Crystallizations with the Water Content Adjusted to 0.5-1%

| Scale (g) | ACN/IPA c ratio v/v | Vol | Temp ° C. | Time to initiate/total | Seed Load (%) | Recovery (%) | % Purity Compound 7a (Compound 6a) |
|---|---|---|---|---|---|---|---|
| 57 | 9:1[a] | 9 | 65-0 | 0.5 | 2%[e] | 82.5 | 93.2 (83.6) |
| 56 | 9:1[a] | 9 | 65-0 | 1 | 2%[f] | 81.8 | 93.4 (83.7) |
| 52 | 9:1[c] | 9 | 65-0 | 1/26 | 5% | 85.8 | 95.1 (88.6) |

[a]Water content adjusted to 0.5% [b]Water content adjusted to 1% [c]Water content adjusted to 2.7% [d]Three temperature cycles 65-40, 70-40, 70-0; crystals formed were "rod-like" [e]Dry seeds used [f]Seeded with Compound 7a "rods" rather than needles.

TABLE 11

Compound 6a to Compound 7a Process with a ACN-IPAc Crystallization

| Scale (g) | Ratio, v/v | Vol | Temp ° C. | Time to initiate/total | Seeded Yes/No | Recovery (%) | % Purity Compound 7a (Compound 6a) |
|---|---|---|---|---|---|---|---|
| 5 | ~2:1 | ~15 | RT | 1.5 h/16 h | no | 64 | 92.3 (83) |
| 6 | 10:4 | 14 | RT | ~4 h/44 h | no | 49 | 94 (82) |
| 4 | 9:1 | 8 | 40-0 | 6 h/98 h | yes | various | 94 (81) |
| 6.6 | 9:1[a] | 8 | 40-0 | 2.5 h/20 h | 2 × 2% | 48.5 | 94.8 (72) |
| 8.2 | 9:1[a] | 8 | 40-RT | 0.5 h/22 h | 3% | 63 | 93.6 (67) |
| 12 | 9:1[b] | ~9 | 50-0 | 0.25 h/24 h | 2% | 75 | 95.2 (81) |
| 30 | 9:1[b] | ~9 | 55-0 | 0.5 h/26 h | 2% | 65 | 94.0 (81) |
| 36 | 9:1[b] | 9 | 55-0 | 0.5 h/26 h | 2% | 71 | 94.2 (81.5) |
| 10 | 9:1[c] | 9 | 60-5 | 1 h/26 h | 2% | 58 | 95.7 (88.0) |
| 41.6 | 9:1[c] | ~9 | ~62-2 | <0.5/20 h | 2% | 82 | 94.5 (97.5) |
| 30.0 | 9:1 | ~9 | ~62-2 | <0.5/20 h | 2% | 78 | 96.0 (98.3) |
| 44.2 | 9:1[d] | ~9 | ~62-2 | <0.5/22 h | 2% | 85 | 95.4 (98.4) |

[a]Water content adjusted to ca. 0.3% [b]Water content adjusted to ca. 0.5% [c]Low recovery presumably due to improper adjustment of water content. [d]Water content adjusted to 3.5%. This entry used the brine wash procedure instead of an acid/base work-up to screen for the loss of product and removal of reagents. The other entries in the table used only a water wash procedure instead of an acid/base work-up.

Water content may be important in controlling the robustness of the crystallization. There was a varying metastable zone determination with about 0-2% added water. An "anhydrous" run with about 0% added water (approximately 0.2-0.3% water content) produced a wide metastable zone with the clear point at about 55-60° C., and the cloud point at below ambient temperature (about 8-15° C.). With the addition of about 0.5-2% water, the metastable zone tightened considerably with the clear point at a higher temperature. The observation suggested that some level of water in the mixture (initially about 0.5-1%) may make the crystallization more reproducible and robust. Karl-Fischer water determination after the azeotropic drying solvent swap from IPAc to ACN during Compound 6a to Compound 7a workup showed the solution to be nearly dry (~200 ppm water), such that crystallizations performed after the azeotropic drying were operating in the anhydrous mode with a very wide metastable zone. This may result in very slow de-saturation and increased chance of spontaneous nucleation. Crystallizations with about 0.5-2% water added may be more reproducible with a consistent recovery (generally greater than about 80%) and an upgrade in purity.

Part 4: Characterization Data for Compound 7a

The XRPD spectrum of Compound 7a is shown in FIG. 7 and the peak positions are substantially in accordance with those listed in Table 2. The TGA profile of Compound 7a is shown in FIG. 8. The DSC profile of Compound 7a is shown in FIG. 9.

Example 4: Synthesis of Plazomicin Sulfate

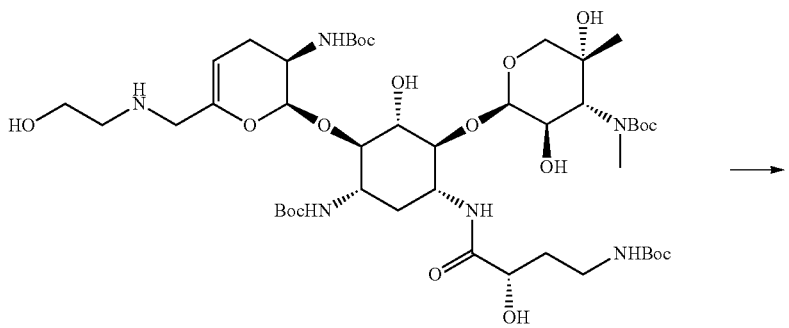

7a

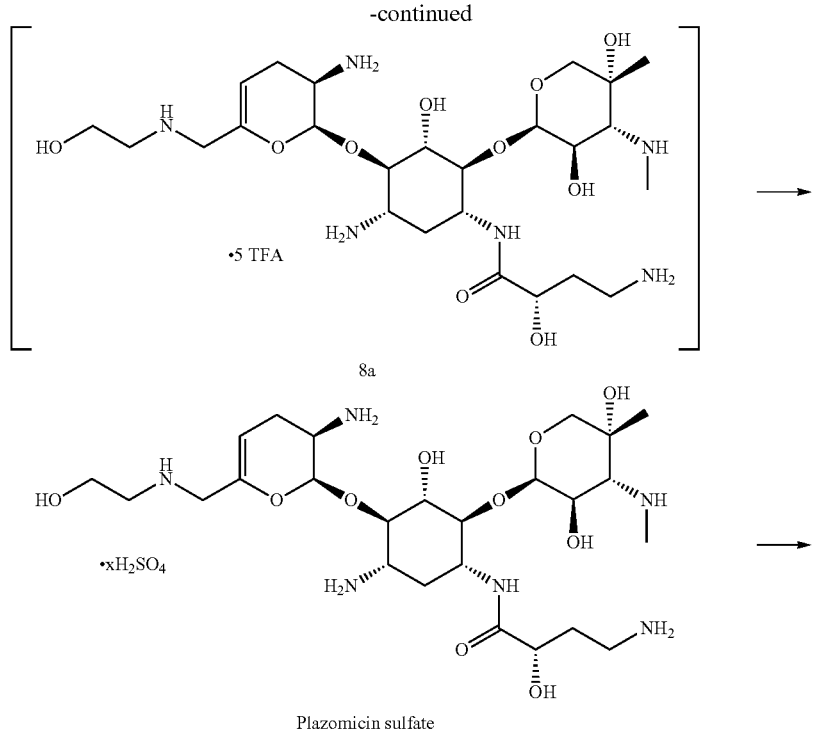

8a

Plazomicin sulfate

30

Part 1: Synthesis of Compound 8a

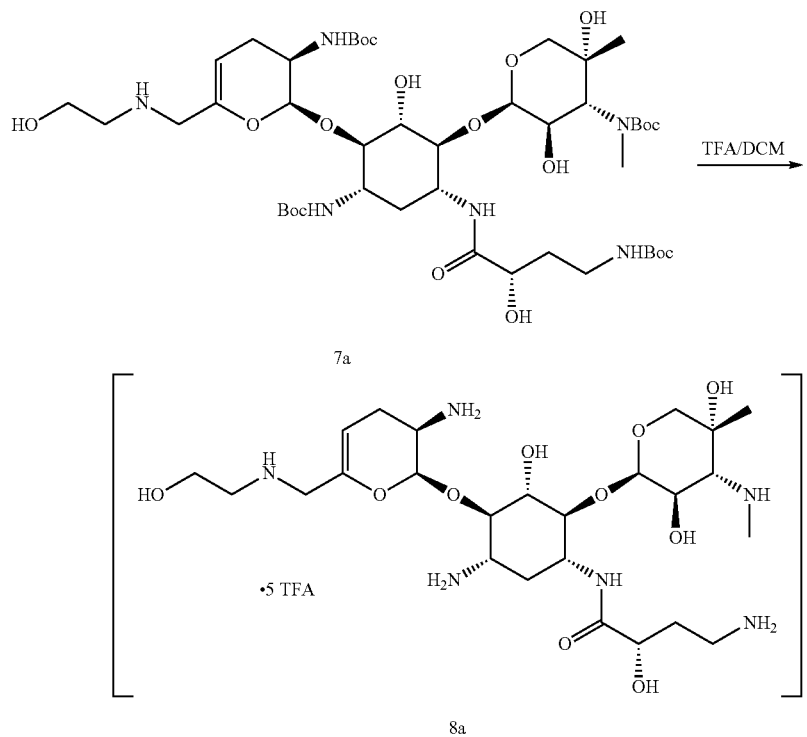

Compound 7a (1.0 kg±1%, 1.00 mol) is charged into a reactor. Dichloromethane (5.0 L±5%) is charged and the mixture is cooled to about 0-5° C. Trifluoroacetic acid (TFA, 3.0 L±5%, 39.5 mol) is charged to the mixture at a rate to maintain the temperature between about 0-5° C. The mixture is then heated to about 20-25° C. and stirred for about 1-2 hours. The mixture is then distilled under vacuum maintaining a reactor jacket temperature of about 20 to 40° C. to a final volume of 3 L±5%. In certain embodiments, the mixture is then distilled under vacuum maintaining a reactor jacket temperature of about 30° C. to a final volume of 3 L±5%. The mixture is then cooled to about 20-25° C. and then stirred for about 1-4 hours before cooling to about 0-10° C. The resulting solution is then charged to a reactor charged with water (about 2.5 L, previously cooled to about 0-5° C.) maintaining a temperature between about 0-10° C.

The reactor is charged with isopropyl acetate (IPAc, 3.0 L±5%) and the mixture is stirred for about 20-30 minutes before the stirring is stopped and the layers are allowed to separate. The lower aqueous layer (aqueous phase 1) is discharged and the organic phase is extracted twice by charging with water (about 0.5 L±5%) and the mixture is stirred for about 15 minutes to 12 hours before the stirring is stopped and the layers are allowed to separate. In certain embodiments, the lower aqueous layer (aqueous phase 1) is discharged and the organic phase is extracted twice by charging with water (about 0.5 L±5%) and the mixture is stirred for about 30 minutes before the stirring is stopped and the layers are allowed to separate. Each lower aqueous layer (aqueous phase 2 and 3) is collected and combined with aqueous phase 1. The combined aqueous phases are then washed with IPAc three times to remove TFA by charging with IPAc (3.0 L±5%) and stirring for about 20-30 minutes before stopping the stirring and allowing the layers to separate. The lower aqueous phase layer is discharged, and the pH is measured to assure the pH>2.0. If the pH is ≤2.0 the IPAc wash is repeated until the pH is greater than about 2.0.

Part 2: Synthesis of Plazomicin Sulfate nia (4 kg±5%) into water (96 kg±5%)) until the pH is between about 5.8 and about 6.2. The conductivity is measured to assure the conductivity is less than or equal to about 20 mS/cm (e.g., 0 to 20 mS/cm). If the conductivity is above 20 mS/cm, additional water is added to bring the conductivity less than or equal to about 20 mS/cm (e.g., 0 to 20 mS/cm).

The crude Compound 8a TFA salt solution is purified by ion exchange chromatography by charging the solution to an ion exchange column containing Amberlite CG-50 (Type 1) resin (2.17 kg) previously converted to the ammonia form. The column is eluted with water (1 column volume±5%) to elute ammonium trifluoroacetate and then is eluted with an aqueous ammonia solution (prepared by diluting about 25% ammonia (2.0 kg±5%) into water (96.0 kg±5%)). The chromatography is monitored by UV absorption. Fractions are collected and analyzed by UPLC, pooling the fractions with greater than about 95% (by area) Compound 8a freebase (the compound without the TFA salt).

The combined chromatography fractions are passed through a filter (porosity 5 microns) and the filter is rinsed with water (1 L±5%). The resulting solution is concentrated by nanofiltration through Dow Filmtec XLE membrane to a final volume of 16 L±5%, maintaining the temperature between about 0-10° C. The ammonia is then removed by diafiltration through a Dow Filmtec XLE membrane.

The solution of Compound 8a freebase is cooled to about 0-5° C. and treated with an aqueous solution of sulfuric acid (prepared by dissolving pure sulfuric acid (0.51 kg±5%) in DI water (0.72 L±5%)) until the pH is between about

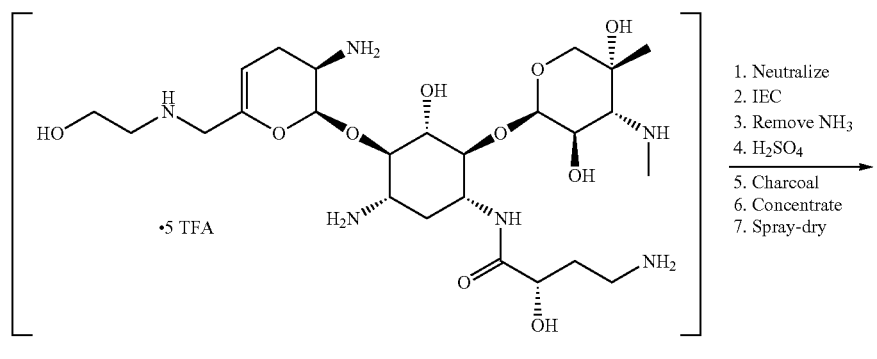

8a

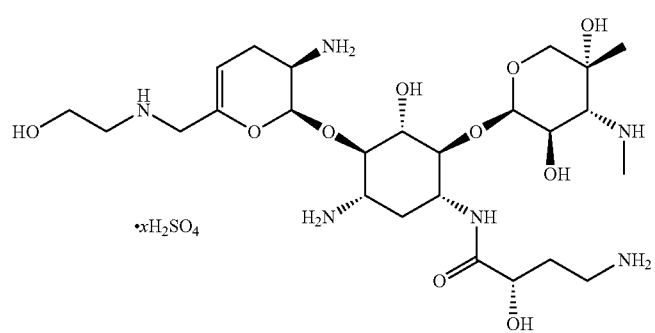

Plazomicin sulfate

The aqueous phase from Part 1 is then diluted with water to a final volume of 9.0 L±5% and treated with an aqueous ammonia solution (prepared by diluting about 25% ammo- 6.0-6.5. The resulting solution of plazomicin sulfate is passed through an activated carbon filter (R55SP) and the filter is washed with water.

The solution is concentrated by nanofiltration using a Dow Filmtec XLE membrane, and then filtered through a 0.22 micron filter. The resulting solution is then fed to a spray dryer, maintaining the spray dryer outlet temperature between about 60-100° C. to collect plazomicin sulfate as an amorphous solid.

Example 5: Example Procedures for the Preparation of 4-nitrobenzyl ((((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, Formula (4a), from Sisomicin

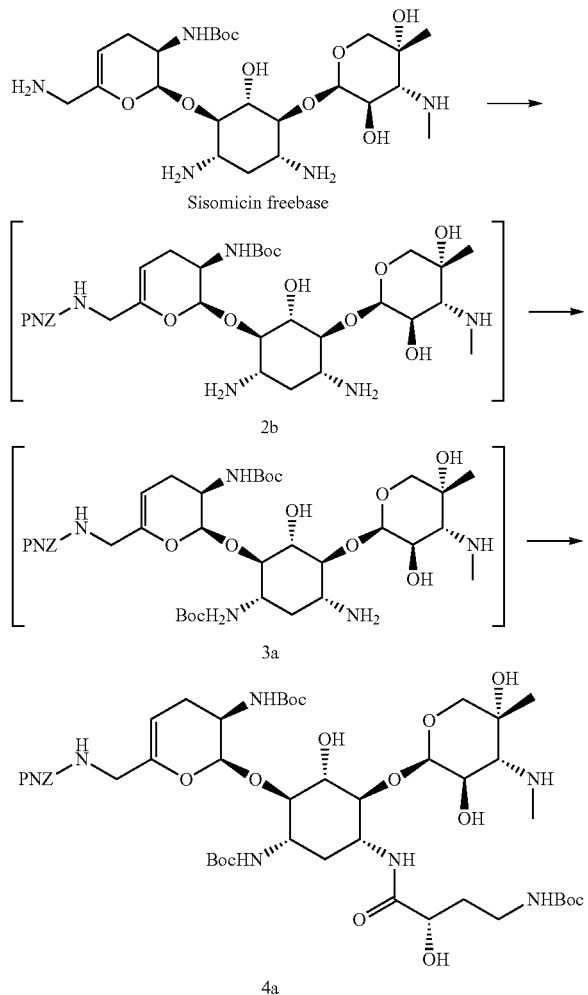

Example 5a

To a jacketed glass reactor equipped with overhead stirring was charged sisomicin freebase (300.0 g, 0.670 mol, KF=5.65) followed by methanol (1500 mL) and dichloromethane (1500 mL). After dissolution the reaction temperature was stabilized at 15° C. A solution of p-nitrobenzyl benzotriazole carbamate (207 g, 0.694 mol, 1.04 equiv) in dichloromethane (4200 mL) was added to the reactor over three hours maintaining the reaction temperature at ca 15° C. The addition was completed with a rinse of dichloromethane (300 mL). After 30 minutes the reaction was sampled and deemed complete by HPLC analysis (consumption of sisomicin). The crude reaction mixture was concentrated under vacuum to a final volume of 1500 mL. Methanol (4500 mL) was charged to the reaction mixture and a second concentration under vacuum was performed to a volume target of 4500 mL.

Methanol (900 mL) was charged to the reaction mixture and the temperature was stabilized at 27.5° C. Triethylamine (442 mL, 3.189 mol, 4.76 equiv) and zinc acetate dihydrate (487 g, 2.219 mol, 3.31 equiv) were charged successively and the mixture was stirred for 1 h. A previously prepared solution of di-tert-butyl-dicarbonate (759 g, 3.478 mol, 5.19 equiv) in methanol (600 mL) was added to the reaction solution over 70 minutes. The transfer was completed with a rinse of methanol (60 mL). After the addition the reaction was stirred for 9.5 h at 27.5° C. when it was sampled and deemed complete by HPLC analysis (consumption of 4-nitrobenzyl ((((2S,3R)-3-amino-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate and mono-Boc protected intermediate=4-nitrobenzyl ((((2S,3R)-3-((tert-butoxycarbonyl)amino)-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate). The crude reaction mixture was concentrated under vacuum to a final volume of 3600 mL. The temperature was stabilized between 20 and 30° C. and the reaction quenched with the addition of 25% ammonia (1800 mL) over 1.5 h (Caution: exothermic addition, addition rate controlled to maintain the reaction temperature between 20 and 30° C.). Dichloromethane (3000 mL) was added and the biphasic mixture was stirred for 20 minutes after which the agitation was stopped and the layers were allowed to separate. The lower product rich organic layer (OP1) was transferred to a receiver while the upper depleted aqueous layer (AQ1) was transferred to waste. OP1 was transfer back into the reactor to which was charged water (750 mL) and 25% ammonia (750 mL). The layers were mixed by agitation and then allowed to separate after which the lower product rich organic layer (OP2) was transferred to a receiver while the upper aqueous layer (AQ2) was transferred to waste. OP2 was transferred back into the reactor to which was charged methanol (300 mL) and water (1500 mL). The layers were mixed by agitation and then allowed to separate after which the lower product rich organic layer (OP3) was transferred to a receiver while the upper aqueous layer (AQ3) was transferred to waste. OP3 was transferred back into the reactor to which was charged methanol (300 mL) and water (1500 mL). The layers were mixed by agitation and then allowed to separate after which the lower product rich organic layer (OP4) was transferred to a receiver while the upper aqueous layer (AQ4) was transferred to waste. The final washed organic phase (OP4) was returned to the reactor and concentrated under vacuum to a volume of 2700 mL.

Water (150 mL), Boc-(S)-HABA (153 g, 0.698 mol, 1.04 equiv), and 1-hydroxybenzotriazole (17 g, 0.125 mol, 0.19 equiv) were added to the reactor. After each solid charge (Boc-(S)-HABA and 1-hydroxybenzotriazole) dichloromethane (60 mL) was used to rinse forward the charging system. The pH of the reaction mixture was adjusted to 5.5 using 2 M hydrochloric acid (1250 mL). After pH adjustment, 1-ethyl-3-(3'diemthylaminopropyl)carbodiimide hydrochloric acid (133 g, 0.694 mol, 1.03 equiv) was charged to the reaction mixture. Dichloromethane (60 mL) was used to rinse forward the solid charge. After 70 minutes, the reaction was sampled and deemed complete by HPLC (consumption of 4-nitrobenzyl (((2S,3R)-2-(((1R,2R,3S,4R,6S)-4-amino-6-((tert-butoxycarbonyl)amino)-3-(((2R,3R,4R,5R)-3,5-dihydroxy-5-methyl-4-(methylamino)tetrahydro-2H-pyran-2-yl)oxy)-2-hydroxycyclohexyl)oxy)-3-((tert-butoxycarbonyl)amino)-3,4-dihydro-2H-pyran-6-yl) met). Methanol (600 mL) was charged to the reaction mixture followed by dichloromethane (3600 mL) and water (1500 mL). The pH was adjusted to 9.5 using sodium hydroxide (1200 mL). The layers were mixed by agitation and then allowed to separate after which the lower product rich organic layer (OP5) was transferred to a receiver while the upper aqueous layer (AQ5) was transferred to waste. OP5 was returned to the reactor followed by water (2100 mL). The layers were mixed by agitation and then allowed to separate after which the lower product rich organic layer (OP6) was transferred to a receiver while the upper aqueous layer (AQ6) was transferred to waste. OP6 was returned to the reactor and concentrated under vacuum to a final volume of 3000 mL. Acetonitrile (3000 mL) was charged to the reactor and the mixture was concentrated under vacuum to a final volume target of 3000 mL. Acetonitrile (3000 mL) was charged to the reactor and the mixture was concentrated under vacuum to a final volume target of 3000 mL. Acetonitrile (ca 4500 mL) was charged to the reaction mixture to a final volume target of 7500 mL.

The mixture was heated to reflux (83° C.) and two portions of water (75 mL and 38 mL) were added successively to produce a solution. The solution was cooled to 75° C. after which 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), seeds (3 g, 0.0029 mol, 0.004 equiv) were charged to the reaction mixture. The newly formed slurry was cooled to 3° C. over 5 h and stirred between 0-5° C. over an additional 4 h. The mixture was filtered, washed with acetonitrile (two portions of 300 mL) and dried under vacuum to afford 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (345.19 g 50% molar yield).

Example 5b

To a jacketed glass reactor equipped with overhead stirring was charged sisomicin freebase (300.0 g, 0.670 mol, 1 equiv, KF=5.65) followed by methanol (1500 mL) and dichloromethane (1500 mL). After dissolution the reaction temperature was stabilized at 15° C. A solution of p-nitrobenzyl benzotriazole carbamate (207 g, 0.694 mol, 1.04 equiv) in dichloromethane (4200 mL) was added to the reactor over three hours maintaining the reaction temperature at ca 15° C. The addition was completed with a rinse of dichloromethane (300 mL). After 30 minutes the reaction was sampled and deemed complete by HPLC analysis (consumption of sisomicin). The crude reaction mixture was concentrated under vacuum to a final volume of 1500 mL.

Methanol (4500 mL) was charged to the reaction mixture and the temperature was stabilized at 20° C. Triethylamine (498 mL, 3.593 mol, 5.36 equiv) and zinc acetate dihydrate (425 g, 1.935 mol, 2.89 equiv) were charged successively and the mixture was stirred for 1 h. A previously prepared solution of di-tert-butyl-dicarbonate (894 g, 4.096 mol, 6.11 equiv) in methanol (600 mL) was added to the reaction solution over 80 minutes. The transfer was completed with a rinse of methanol (60 mL). After the addition the reaction was stirred for 5 h at 20° C. when it was sampled and deemed complete by HPLC analysis (consumption of 4-nitrobenzyl (((2S,3R)-3-amino-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl) methyl)carbamate and mono-Boc protected intermediate=4-nitrobenzyl (((2S,3R)-3-((tert-butoxycarbonyl)amino)-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate). The crude reaction mixture was concentrated under vacuum to a final volume of 3000 mL. The temperature was stabilized between 20 and 30° C. and the reaction quenched with the addition of 25% ammonia (1500 mL) over 1.5 h (Caution: exothermic addition, addition rate controlled to maintain the reaction temperature between 20 and 30° C.). Dichloromethane (3000 mL) was added and the biphasic mixture was stirred after which the agitation was stopped and the layers were allowed to separate. The lower product rich organic layer (OP1) was transferred to a receiver while the upper depleted aqueous layer (AQ1) was transferred to waste. OP1 was transfer back into the reactor to which was charged water (750 mL) and 25% ammonia (750 mL). The layers were mixed by agitation and then allowed to separate after which the lower product rich organic layer (OP2) was transferred to a receiver while the upper aqueous layer (AQ2) was transferred to waste. OP2 was transferred back into the reactor to which was charged methanol (225 mL) and water (1500 mL). The layers were mixed by agitation and then allowed to separate after which the lower product rich organic layer (OP3) was transferred to a receiver while the upper aqueous layer (AQ3) was transferred to waste. OP3 was transferred back into the reactor to which was charged methanol (225 mL) and water (1500 mL). The layers were mixed by agitation and then allowed to separate after which the lower product rich organic layer (OP4) was transferred to a receiver while the upper aqueous layer (AQ4) was transferred to waste. The final washed organic phase (OP4) was returned to the reactor and concentrated under vacuum to a volume of 2700 mL.

Water (150 mL), Boc-(S)-HABA (153 g, 0.698 mol, 1.04 equiv), and 1-hydroxybenzotriazole (17 g, 0.126 mol, 0.19 equiv) were added to the reactor. After each solid charge (Boc-(S)-HABA and 1-hydroxybenzotriazole) dichloromethane (60 mL) was used to rinse forward the charging system. The pH of the reaction mixture was adjusted to 6.2 using 2 M hydrochloric acid (1098 mL). After pH adjustment, 1-ethyl-3-(3'diemthylaminopropyl)carbodiimide hydrochloric acid (133 g, 0.694, 1.03 equiv) was charged to the reaction mixture. Dichloromethane (60 mL) was used to rinse forward the solid charge. After 2 h, the reaction was sampled and deemed complete by HPLC (consumption of 4-nitrobenzyl (((2S,3R)-2-(((1R,2R,3S,4R,6S)-4-amino-6-((tert-butoxycarbonyl)amino)-3-(((2R,3R,4R,5R)-3,5-dihydroxy-5-methyl-4-(methylamino)tetrahydro-2H-pyran-2-yl)

oxy)-2-hydroxycyclohexyl)oxy)-3-((tert-butoxycarbonyl) amino)-3,4-dihydro-2H-pyran-6-yl)met). Methanol (525 mL) was charged to the reaction mixture followed by dichloromethane (3600 mL) and water (1500 mL). The pH was adjusted to 8.5 using sodium hydroxide (365 mL). The layers were mixed by agitation and then allowed to separate after which the lower product rich organic layer (OP5) was transferred to a receiver while the upper aqueous layer (AQ5) was transferred to waste. OP5 was returned to the reactor followed by water (2100 mL). The layers were mixed by agitation and then allowed to separate after which the lower product rich organic layer (OP6) was transferred to a receiver while the upper aqueous layer (AQ6) was transferred to waste. OP6 was returned to the reactor and concentrated under vacuum to a final volume of 3000 mL. Acetonitrile (3000 mL) was charged to the reactor and the mixture was concentrated under vacuum to a final volume target of 3000 mL. Acetonitrile (3000 mL) was charged to the reactor and the mixture was concentrated under vacuum to a final volume target of 3000 mL. Acetonitrile (ca 6000 mL) was charged to the reaction mixture to a final volume target of 9000 mL.

The mixture was heated to reflux (83° C.) and two portions of water (75 mL and 38 mL) were added successively to produce a solution. The solution was cooled to 75° C. after which 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl) methyl)carbamate, formula (4a) seeds (3 g, 0.0029 mol, 0.004 equiv) were charged to the reaction mixture. The newly formed slurry was cooled to 3° C. over 5 h and stirred between 0-5° C. over an additional 4 h. The mixture was filtered, washed with acetonitrile (two portions of 300 mL) and dried under vacuum to afford 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (340.68 g, 49% molar yield)

Example 5c

To a jacketed glass reactor equipped with overhead stirring was charged sisomicin freebase (300.0 g, 0.670 mol, 1 equivKF=5.65) followed by methanol (1500 mL) and dichloromethane (1500 mL). After dissolution the reaction temperature was stabilized at 15° C. A solution of p-nitrobenzyl benzotriazole carbamate (189 g, 0.664 mol, 0.99 equiv) in dichloromethane (4200 mL) was added to the reactor over three hours maintaining the reaction temperature at ca 15° C. The addition was completed with a rinse of dichloromethane (300 mL). After 29 minutes the reaction was sampled and deemed complete by HPLC analysis (consumption of sisomicin). The crude reaction mixture was concentrated under vacuum to a final volume of 1500 mL. Methanol (4500 mL) was charged to the reaction mixture and a second concentration under vacuum was performed to a volume target of 4500 mL.

Methanol (900 mL) was charged to the reaction mixture and the temperature was stabilized at 35° C. Triethylamine (385 mL, 2.777 mol, 4.14 equiv) and zinc acetate dihydrate (549 g, 2.501 mol, 3.73 equiv) were charged successively and the mixture was stirred for 1 h. A previously prepared solution of di-tert-butyl-dicarbonate (620 g, 2.841 mol, 4.24) in methanol (600 mL) was added to the reaction solution over 60 minutes. The transfer was completed with a rinse of methanol (60 mL). After the addition the reaction was stirred for 5 h at 35° C. when it was sampled and deemed complete by HPLC analysis (consumption of 4-nitrobenzyl (((2S,3R)-3-amino-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate and mono-Boc protected intermediate=4-nitrobenzyl (((2S,3R)-3-((tert-butoxycarbonyl)amino)-2-(((1R,2S,3S,4R,6S)-4,6-diamino-3-(((2R,3R,4R,5R)-3,5-dihydroxy-5-methyl-4-(methylamino) tetrahydro-2H-pyran-2-yl)oxy)-2-hydroxycyclohexyl)oxy)-3,4-dihydro-2H-pyran-6-yl)methyl)carbamate). The crude reaction mixture was concentrated under vacuum to a final volume of 4200 mL. The temperature was stabilized between 20 and 30° C. and the reaction quenched with the addition of 25% ammonia (2100 mL) over 1 h and 27 min (Caution: exothermic addition, addition rate controlled to maintain the reaction temperature between 20 and 30° C.). Dichloromethane (3000 mL) was added and the biphasic mixture was stirred for 20 minutes after which the agitation was stopped and the layers were allowed to separate. The lower product rich organic layer (OP1) was transferred to a receiver while the upper depleted aqueous layer (AQ1) was transferred to waste. OP1 was transfer back into the reactor to which was charged water (750 mL) and 25% ammonia (750 mL). The layers were mixed by agitation and then allowed to separate after which the lower product rich organic layer (OP2) was transferred to a receiver while the upper aqueous layer (AQ2) was transferred to waste. OP2 was transferred back into the reactor to which was charged methanol (375 mL) and water (1500 mL). The layers were mixed by agitation and then allowed to separate after which the lower product rich organic layer (OP3) was transferred to a receiver while the upper aqueous layer (AQ3) was transferred to waste. OP3 was transferred back into the reactor to which was charged methanol (375 mL) and water (1500 mL). The layers were mixed by agitation and then allowed to separate after which the lower product rich organic layer (OP4) was transferred to a receiver while the upper aqueous layer (AQ4) was transferred to waste. The final washed organic phase (OP4) was returned to the reactor and concentrated under vacuum to a volume of 2700 mL.

Water (150 mL), Boc-(S)-HABA (153 g, 0.698 mol, 1.04 equiv), and 1-hydroxybenzotriazole (17 g, 0.126 mol, 0.19 equiv) were added to the reactor. After each solid charge (Boc-(S)-HABA and 1-hydroxybenzotriazole) dichloromethane (60 mL) was used to rinse forward the charging system. The pH of the reaction mixture was adjusted to 4.8 using 2 M hydrochloric acid (1250 mL). After pH adjustment, 1-ethyl-3-(3'diemthylaminopropyl)carbodiimide hydrochloric acid (133 g, 0.694 mol, 1.03 equiv) was charged to the reaction mixture. Dichloromethane (60 mL) was used to rinse forward the solid charge. After 70 minutes, the reaction was sampled and deemed complete by HPLC (consumption of 4-nitrobenzyl (((2S,3R)-2-(((1R,2R,3S,4R, 6S)-4-amino-6-((tert-butoxycarbonyl)amino)-3-(((2R,3R, 4R,5R)-3,5-dihydroxy-5-methyl-4-(methylamino)tetrahydro-2H-pyran-2-yl)oxy)-2-hydroxycyclohexyl)oxy)-3-((tert-butoxycarbonyl)amino)-3,4-dihydro-2H-pyran-6-yl) met). Methanol (675 mL) was charged to the reaction mixture followed by dichloromethane (3600 mL) and water 1500 mL). The pH was adjusted to 10.5 using sodium hydroxide (1264 mL). The layers were mixed by agitation and then allowed to separate after which the lower product rich organic layer (OP5) was transferred to a receiver while the upper aqueous layer (AQ5) was transferred to waste. OP5 was returned to the reactor followed by water (2100 mL). The layers were mixed by agitation and then allowed to separate after which the lower product rich organic layer (OP6) was transferred to a receiver while the upper aqueous layer (AQ6) was transferred to waste. OP6 was returned to the reactor and concentrated under vacuum to a final volume of 3000 mL. Acetonitrile (3000 mL) was charged to the reactor and the mixture was concentrated under vacuum to a final volume target of 3000 mL. Acetonitrile (3000 mL) was charged to the reactor and the mixture was concentrated under vacuum to a final volume target of 3000 mL. Acetonitrile (ca 3000 mL) was charged to the reaction mixture to a final volume target of 6000 mL.

The mixture was heated to reflux (83° C.) and two portions of water (75 mL and 38 mL) were added successively to produce a solution. The solution was cooled to 75° C. after which 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), seeds (3 g, 0.0029 mmol, 0.004 equiv) were charged to the reaction mixture. The newly formed slurry was cooled to 3° C. over 5 h and stirred between 0-5° C. over an additional 4 h. The mixture was filtered, washed with acetonitrile (two portions of 300 mL) and dried under vacuum to afford 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (347.03 g, 50% yield)

Example 5d

To a jacketed glass reactor equipped with overhead stirring was charged sisomicin freebase (90.0 g, KF=5.65) followed by methanol (450 mL) and dichloromethane (450 mL). After dissolution the reaction temperature was stabilized at 15° C. A solution of p-nitrobenzyl benzotriazole carbamate (62 g) in dichloromethane (1260 mL) was added to the reactor over three hours maintaining the reaction temperature at ca 15° C. The addition was completed with a rinse of dichloromethane (90 mL). After 32 minutes the reaction was sampled and deemed complete by HPLC analysis (consumption of sisomicin). The crude reaction mixture was concentrated under vacuum to a final volume of 450 mL.

Methanol (1350 mL) was charged to the reaction mixture and the reaction was further concentrated under vacuum to a final volume target of 1350 mL. A second portion of methanol (270 mL) was charged to the reaction mixture and the temperature was stabilized at 27.5° C. Triethylamine (132 mL, 0.952 mol, 4.74 equiv) and zinc acetate dihydrate (146 g, 0.665 mol, 3.31 equiv) were charged successively and the mixture was stirred for 1 h. A previously prepared solution of di-tert-butyl-dicarbonate (228 g, 1.045 mol, 5.19 equiv) in methanol (180 mL) was added to the reaction solution over 70 minutes. The transfer was completed with a rinse of methanol (18 mL). After the addition the reaction was stirred for 13 h at 27.5° C. when it was sampled and deemed complete by HPLC analysis (consumption of 4-nitrobenzyl (((2S,3R)-3-amino-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate and mono-Boc protected intermediate=4-nitrobenzyl (((2S,3R)-3-((tert-butoxycarbonyl)amino)-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate). The crude reaction mixture was concentrated under vacuum to a final volume of 1080 mL. The temperature was stabilized between 20 and 30° C. and the reaction quenched with the addition of 25% ammonia (540 mL) over 37 min (Caution: exothermic addition, addition rate controlled to maintain the reaction temperature between 20 and 30° C.). Dichloromethane (900 mL) was added and the biphasic mixture was stirred for 20 minutes after which the agitation was stopped and the layers were allowed to separate. The lower product rich organic layer (OP1) was transferred to a receiver while the upper depleted aqueous layer (AQ1) was transferred to waste. OP1 was transfer back into the reactor to which was charged water (225 mL) and 25% ammonia (225 mL). The layers were mixed by agitation and then allowed to separate after which the lower product rich organic layer (OP2) was transferred to a receiver while the upper aqueous layer (AQ2) was transferred to waste. OP2 was transferred back into the reactor to which was charged methanol (90 mL) and water (450 mL). The layers were mixed by agitation and then allowed to separate after which the lower product rich organic layer (OP3) was transferred to a receiver while the upper aqueous layer (AQ3) was transferred to waste. OP3 was transferred back into the reactor to which was charged methanol (90 mL) and water (450 mL). The layers were mixed by agitation and then allowed to separate after which the lower product rich organic layer (OP4) was transferred to a receiver while the upper aqueous layer (AQ4) was transferred to waste. The final washed organic phase (OP4) was returned to the reactor and concentrated under vacuum to a volume of 810 mL.

Water (45 mL), Boc-(S)-HABA (46 g, 0.210 mol, 1.04 equiv), and 1-hydroxybenzotriazole (5 g, 0.037 mol, 0.18 equiv) were added to the reactor. After each solid charge (Boc-(S)-HABA and 1-hydroxybenzotriazole) dichloromethane (18 mL) was used to rinse forward the charging system. The pH of the reaction mixture was adjusted to 5.5 using 2 M hydrochloric acid (380 mL). After pH adjustment, 1-ethyl-3-(3'diemthylaminopropyl)carbodiimide hydrochloric acid (40 g, 0.209 mol, 1.04 equiv) was charged to the reaction mixture. Dichloromethane (18 mL) was used to rinse forward the solid charge. After 2 h and 40 min, the reaction was sampled and deemed complete by HPLC (consumption of 4-nitrobenzyl (((2S,3R)-2-(((1R,2R,3S,4R,6S)-4-amino-6-((tert-butoxycarbonyl)amino)-3-(((2R,3R,4R,5R)-3,5-dihydroxy-5-methyl-4-(methylamino)tetrahydro-2H-pyran-2-yl)oxy)-2-hydroxycyclohexyl)oxy)-3-((tert-butoxycarbonyl)amino)-3,4-dihydro-2H-pyran-6-yl) met). Methanol (180 mL) was charged to the reaction mixture followed by dichloromethane (1080 mL) and water (450 mL). The pH was adjusted to 9.5 using sodium hydroxide (400 mL). The layers were mixed by agitation and then allowed to separate after which the lower product rich organic layer (OP5) was transferred to a receiver while the upper aqueous layer (AQ5) was transferred to waste. OP5 was returned to the reactor followed by water (630 mL). The layers were mixed by agitation and then allowed to separate after which the lower product rich organic layer (OP6) was transferred to a receiver while the upper aqueous layer (AQ6) was transferred to waste. OP6 was returned to the reactor and concentrated under vacuum to a final volume of 3000 mL. Acetonitrile (900 mL) was charged to the reactor and the mixture was concentrated under vacuum to a final volume target of 900 mL. Acetonitrile (900 mL) was charged to the reactor and the mixture was concentrated under vacuum to a final volume target of 900 mL. Acetonitrile (ca 1350 mL) was charged to the reaction mixture to a final volume target of 2250 mL.

The mixture was heated to reflux (ca 80° C.) and two portions of water (23 mL and 11 mL) were added successively to produce a solution. The solution was cooled to 75° C. after which 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), seeds (1 g, 0.0010 mol, 0.005 equiv) were charged to the reaction mixture. The newly formed slurry was cooled to 3° C. over 5 h and stirred between 0-5° C. over an additional 4 h. The mixture was filtered, washed with acetonitrile (two portions of 300 mL) and dried under vacuum to afford 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (105.43 g, 51% molar yield)

Example 5e

To a jacketed glass reactor equipped with overhead stirring was charged sisomicin freebase (300.0 g, 0.670 mol, 1 equiv, KF=5.65) followed by methanol (1500 mL) and dichloromethane (1500 mL). After dissolution the reaction temperature was stabilized at 15° C. A solution of p-nitrobenzyl benzotriazole carbamate (226 g, 0.758 mol, 1.13 equiv) in dichloromethane (4200 mL) was added to the reactor over three hours maintaining the reaction temperature at ca 15° C. The addition was completed with a rinse of dichloromethane (300 mL). After 30 minutes the reaction was sampled and deemed complete by HPLC analysis (consumption of sisomicin). The crude reaction mixture was concentrated under vacuum to a final volume of 1500 mL. Methanol (4500 mL) was charged to the reaction mixture and a second concentration under vacuum was performed to a volume target of 4500 mL.

Methanol (900 mL) was charged to the reaction mixture and the temperature was stabilized at 20° C. Triethylamine (498 mL, 3.593 mol, 5.36 equiv) and zinc acetate dihydrate (425 g, 1.936 mol, 2.89 equiv) were charged successively and the mixture was stirred for 1 h. A previously prepared solution of di-tert-butyl-dicarbonate (894 g, 4.096 mol, 6.11 equiv) in methanol (600 mL) was added to the reaction solution over 60 minutes. The transfer was completed with a rinse of methanol (60 mL). After the addition the reaction was stirred for 9 h at 20.0° C. when it was sampled and deemed complete by HPLC analysis (consumption of 4-nitrobenzyl (((2S,3R)-3-amino-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate and mono-Boc protected intermediate=4-nitrobenzyl (((2S,3R)-3-((tert-butoxycarbonyl)amino)-2-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate). The crude reaction mixture was concentrated under vacuum to a final volume of 3000 mL. The temperature was stabilized between 20 and 30° C. and the reaction quenched with the addition of 25% ammonia (1500 mL) over 109 min (Caution: exothermic addition, addition rate controlled to maintain the reaction temperature between 20 and 30° C.). Dichloromethane (3000 mL) was added and the biphasic mixture was stirred for 20 minutes after which the agitation was stopped and the layers were allowed to separate. The lower product rich organic layer (OP1) was transferred to a receiver while the upper depleted aqueous layer (AQ1) was transferred to waste. OP1 was transfer back into the reactor to which was charged water (750 mL) and 25% ammonia (750 mL). The layers were mixed by agitation and then allowed to separate after which the lower product rich organic layer (OP2) was transferred to a receiver while the upper aqueous layer (AQ2) was transferred to waste. OP2 was transferred back into the reactor to which was charged methanol (225 mL) and water (1500 mL). The layers were mixed by agitation and then allowed to separate after which the lower product rich organic layer (OP3) was transferred to a receiver while the upper aqueous layer (AQ3) was transferred to waste. OP3 was transferred back into the reactor to which was charged methanol (225 mL) and water (1500 mL). The layers were mixed by agitation and then allowed to separate after which the lower product rich organic layer (OP4) was transferred to a receiver while the upper aqueous layer (AQ4) was transferred to waste. The final washed organic phase (OP4) was returned to the reactor and concentrated under vacuum to a volume of 2700 mL.

Water (150 mL), Boc-(S)-HABA (153 g, 0.698 mol, 1.04 equiv), and 1-hydroxybenzotriazole (17 g, 0.126 mol, 0.19 equiv) were added to the reactor. After each solid charge (Boc-(S)-HABA and 1-hydroxybenzotriazole) dichloromethane (60 mL) was used to rinse forward the charging system. The pH of the reaction mixture was adjusted to 6.2 using 2 M hydrochloric acid (1122 mL). After pH adjustment, 1-ethyl-3-(3'diemthylaminopropyl)carbodiimide hydrochloric acid (133 g, 0694 mol, 1.03 equiv) was charged to the reaction mixture. Dichloromethane (60 mL) was used to rinse forward the solid charge. After 4 h, the reaction was sampled and deemed complete by HPLC (consumption of 4-nitrobenzyl (((2S,3R)-2-(((1R,2R,3S,4R,6S)-4-amino-6-((tert-butoxycarbonyl)amino)-3-(((2R,3R,4R,5R)-3,5-dihydroxy-5-methyl-4-(methylamino)tetrahydro-2H-pyran-2-yl)oxy)-2-hydroxycyclohexyl)oxy)-3-((tert-butoxycarbonyl)amino)-3,4-dihydro-2H-pyran-6-yl)met). Methanol (525 mL) was charged to the reaction mixture followed by dichloromethane (3600 mL) and water 1500 mL). The pH was adjusted to 8.5 using sodium hydroxide (430 mL). The layers were mixed by agitation and then allowed to separate after which the lower product rich organic layer (OP5) was transferred to a receiver while the upper aqueous layer (AQ5) was transferred to waste. OP5 was returned to the reactor followed by water (2100 mL). The layers were mixed by agitation and then allowed to separate after which the lower product rich organic layer (OP6) was transferred to a receiver while the upper aqueous layer (AQ6) was transferred to waste. OP6 was returned to the reactor and concentrated under vacuum to a final volume of 3000 mL. Acetonitrile (3000 mL) was charged to the reactor and the mixture was concentrated under vacuum to a final volume target of 3000 mL. Acetonitrile (3000 mL) was charged to the reactor and the mixture was concentrated under vacuum to a final volume target of 3000 mL. Acetonitrile (ca 6000 mL) was charged to the reaction mixture to a final volume target of 9000 mL.

The mixture was heated to reflux (83° C.) and two portions of water (75 mL and 38 mL) were added successively to produce a solution. The solution was cooled to 80° C. after which 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), seeds (3 g, 0.0029 mol, 0.004 equiv) were charged to the reaction mixture. The newly formed slurry was cooled to 3° C. over 5 h and stirred between 0-5° C. over an additional 4 h. The mixture was filtered, washed with acetonitrile (two portions of 300 mL) and dried under vacuum to afford 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (364.8 g, 53% molar yield)

Example 6: Example Procedures for the Preparation of tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a) from 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, Formula (4a)

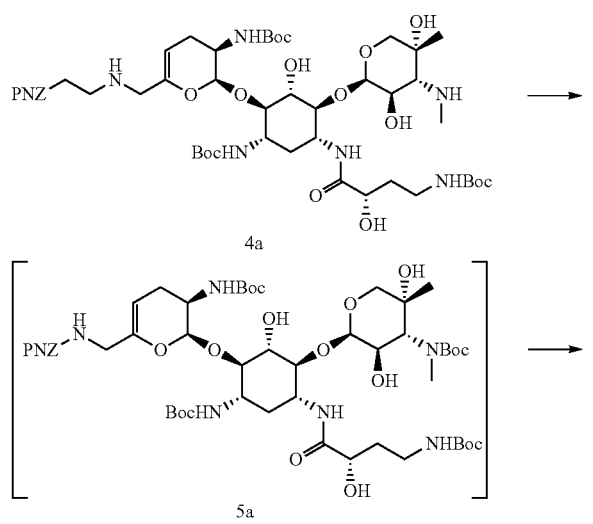

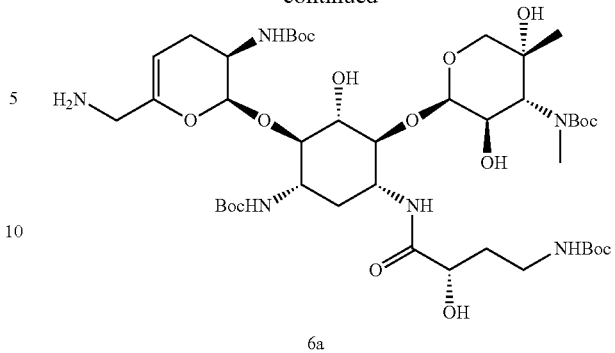

Example 6a

To a jacketed glass reactor (reactor A) equipped with overhead stirring, was charged 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (320 g, 0.311 mol, 1 equiv). Methanol (3200 mL) was charged to the reactor and the temperature was stabilized between 45 and 55° C. (47° C.). A previously prepared solution of di-tert-butyl-dicarbonate (81.60 g, 0.374 mol, 1.20 equiv) in methanol (80 mL) was added to the reaction solution over 3 minutes. The charge was completed with a rinse through of methanol (80 mL). After 3 h the reaction was sampled and deemed complete by HPLC analysis (consumption of 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a),).

To a second jacketed glass reactor (reactor B) equipped with overhead stirring, was charged water (2810 g) and sodium hydroxide (131 g, 3.275 mol, 10.52 equiv). This basic solution was cooled to 10° C. Sodium dithionite (402 g) was charged to the solution and the temperature was stabilized at 12.5° C.

The reaction mixture containing intermediate tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((((4-nitrobenzyl)oxy)carbonyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate (reactor A) was transfer to the sodium dithionite mixture (reactor B) over a period of 1 h while maintaining the temperature of the dithionite reaction mixture at 12.5° C. The transfer was completed with a charge of methanol (160 mL). At the conclusion of the addition, the reaction mixture was heated to 20° C. over a period of 3 h. After 14 h the reaction was sampled and deemed complete by HPLC analysis (consumption of tert-butyl ((2R,3R,4R,5R)-2-(((1S,2S,3R,4S,6R)-3-(((2S,3R)-6-(((((4-aminobenzyl)oxy)carbonyl)amino)methyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)

amino)-2-hydroxybutanamido)-2-hydroxycyclohexyl)oxy)-3,5-dihydroxy-5-methyltetrahydro-2H-pyran-4-yl)(methyl) carbamate). The reaction was concentrated under vacuum with a maximum jacket temperature of 35° C. to a final volume of 4160 mL. Isopropyl acetate (1280 mL) and water (1920 mL) were charged to the reaction mixture. The layers were mixed by agitation at 35° C. and then allowed to separate after which the lower aqueous layer aqueous layer (AP1) and the upper organic layer (OP1) were transferred to receivers. AP1 was returned to the reactor and further extracted with another portion of isopropyl acetate (640 mL) to generate aqueous layer 2 (AP2) and organic layer (OP2). AP2 was sent to waste while OP2 was combined with OP1 in the reactor. This combined product rich organic solution was washed with two portions of 6.5% sodium bicarbonate solution (2 portions of 960 mL). The washed organic phases were concentrated under vacuum to a volume target of 960 mL. Isopropyl acetate (960 mL) was charged to the reactor and a second azeotropic distillation was performed with a volume target of 960 mL. Another portion of Isopropyl acetate (960 mL) was charged to the reactor and a third azeotropic distillation was performed to a volume target of 1120 mL. The temperature was stabilized at 37.5° C. and water (17 mL) was charged to the mixture to achieve a KF of 1.5% w/w. Dichloromethane (1120 mL) was charged to the reactor and the temperature was stabilized at 10.7° C. The mixture was seeded with tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (6.4 g, 0.0067 mol, 0.02 equiv). A portion of dichloromethane (32 mL) was used to rinse forward the seeds. The seeded mixture was stirred for 2 h at 10° C. and cooled to 0° C. over a period of 2 h. The slurry was further stirred for a period of 3.5 h after which it was filtered and washed with dichloromethane (320 mL). The isolated material was dried in a vacuum oven to afford tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (259.66 g, 88% molar yield)

Example 6b

To a jacketed glass reactor (reactor A) equipped with overhead stirring, was charged 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (320 g, 0.311 mol, 1 equiv). Methanol (3200 mL) was charged to the reactor and the temperature was stabilized between 45 and 55° C. (50° C.). A previously prepared solution of di-tert-butyl-dicarbonate (81.60 g, 0.374 mol, 1.20 equiv) in methanol (80 mL) was added to the reaction solution over 5 minutes. The charge was completed with a rinse through of methanol (80 mL). After 5 h, an additional portion of a previously prepared solution of di-tert-butyl-dicarbonate (1.92 g) in methanol (1.9 mL) was added to the reaction solution. After 1 h, the reaction was sampled and deemed complete by HPLC analysis (consumption of 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino) tetrahydro-2H-pyran-2-yl)oxy)-2-hydroxycyclohexyl)oxy)-3,4-dihydro-2H-pyran-6-yl)methyl)carbamate, formula (4a)).

To a second jacketed glass reactor (reactor B) equipped with overhead stirring, was charged water (2490 g) and sodium hydroxide (125 g, 3.125 mol, 10.04 equiv). This basic solution was cooled to 5° C. Sodium dithionite (383 g, 2.200 mol, 7.07 equiv) was charged to the solution and the temperature was stabilized at 7.5° C.

The reaction mixture containing intermediate tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl) amino)-6-(((((4-nitrobenzyl)oxy)carbonyl)amino)methyl)-3,4-dihydro-2H-pyran-2-yl)oxy)-2-hydroxycyclohexyl) oxy)-3,5-dihydroxy-5-methyltetrahydro-2H-pyran-4-yl)(methyl)carbamate (reactor A) was transfer to the sodium dithionite mixture (reactor B) over a period of 1 h while maintaining the temperature of the dithionite reaction mixture at 7.5° C. The transfer was completed with a charge of methanol (160 mL). At the conclusion of the addition, the reaction mixture was heated to 27.5° C. over a period of 2 h. After 7 h the reaction was sampled and deemed complete by HPLC analysis (consumption of tert-butyl ((2R,3R,4R,5R)-2-(((1S,2S,3R,4S,6R)-3-(((2S,3R)-6-(((((4-aminobenzyl)oxy)carbonyl)amino)methyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate). The reaction was concentrated under vacuum with a maximum jacket temperature of 35° C. to a final volume of 4160 mL. Isopropyl acetate (1280 mL) and water (1920 mL) were charged to the reaction mixture. The layers were mixed by agitation at 35° C. and then allowed to separate after which the lower aqueous layer aqueous layer (AP1) and the upper organic layer (OP1) were transferred to receivers. AP1 was returned to the reactor and further extracted with another portion of isopropyl acetate (640 mL) to generate aqueous layer 2 (AP2) and organic layer (OP2). AP2 was sent to waste while OP2 was combined with OP1 in the reactor. This combined product rich organic solution was washed with two portions of 6.5% sodium bicarbonate solution (2 portions of 960 mL). The washed organic phases were concentrated under vacuum to a volume target of 960 mL. Isopropyl acetate (960 mL) was charged to the reactor and a second azeotropic distillation was performed with a volume target of 960 mL. Another portion of Isopropyl acetate (960 mL) was charged to the reactor and a third azeotropic distillation was performed to a volume target of 1440 mL. The temperature was stabilized at 37.5° C. and water (42 mL) was charged to the mixture to achieve a KF of 2.9% w/w. Dichloromethane (1440 mL) was charged to the reactor and the temperature was stabilized at 22.5° C. The mixture was seeded with tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (6.4 g, 0.0067 mol, 0.02 equiv). A portion of dichloromethane (32 mL) was used to rinse forward the seeds. The seeded mixture was stirred for 2 h at 22.5° C. and cooled to 0° C. over a period of 2 h. The slurry was further stirred for a period of 3.5 h after which it was filtered and washed with dichloromethane (320 mL). The isolated material was dried in a vacuum oven to afford tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (257.77 g, 87% yield)

Example 6c

To a jacketed glass reactor (reactor A) equipped with overhead stirring, was charged 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (320 g, 0.311 mol, 1 equiv). Methanol (3200 mL) was charged to the reactor and the temperature was stabilized between 45 and 55° C. (50° C.). A previously prepared solution of di-tert-butyl-dicarbonate (81.60 g, 0.394 mol, 1.20 equiv) in methanol (80 mL) was added to the reaction solution over 3 minutes. The charge was completed with a rinse through of methanol (80 mL). After 3 h the reaction was sampled and deemed complete by HPLC analysis (consumption of 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a)).

To a second jacketed glass reactor (reactor B) equipped with overhead stirring, was charged water (2170 g) and sodium hydroxide (118 g, 2.950 mol, 9.48 equiv). This basic solution was cooled to 0° C. Sodium dithionite (364 g, 2.091 mol, 6.72 equiv) was charged to the solution and the temperature was stabilized at 2.5° C.

The reaction mixture containing intermediate tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((((4-nitrobenzyl)oxy)carbonyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate (reactor A) was transfer to the sodium dithionite mixture (reactor B) over a period of 5 h while maintaining the temperature of the dithionite reaction mixture at 2.5° C. The transfer was completed with a charge of methanol (160 mL). At the conclusion of the addition, the reaction mixture was heated to 35° C. over a period of 1 h. After 3 h the reaction was sampled and deemed complete by HPLC analysis (consumption of tert-butyl ((2R,3R,4R,5R)-2-(((1S,2S,3R,4S,6R)-3-(((2S,3R)-6-(((((4-aminobenzyl)oxy)carbonyl)amino)methyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate). The reaction was concentrated under vacuum with a maximum jacket temperature of 35° C. to a final volume of 4160 mL. Isopropyl acetate (1280 mL) and water (1920 mL) were charged to the reaction mixture. The layers were mixed by agitation at 35° C. and then allowed to separate after which the lower aqueous layer aqueous layer (AP1) and the upper organic layer (OP1) were transferred to receivers. AP1 was returned to the reactor and further extracted with another portion of isopropyl acetate (640 mL) to generate aqueous layer 2 (AP2) and organic layer (OP2). AP2 was sent to waste while OP2 was combined with OP1 in the reactor. This combined product rich organic solution was washed with two portions of 6.5% sodium bicarbonate solution (2 portions of 960 mL). The washed organic phases were concentrated under vacuum to a volume target of 960 mL. Isopropyl acetate (960 mL) was charged to the reactor and a second azeotropic distillation was performed with a volume target of 960 mL. Another portion of Isopropyl acetate (960 mL) was charged to the reactor and a third azeotropic distillation was performed to a volume target of 1760 mL. The temperature was stabilized at 37.5° C. and water (71.2 mL) was charged to the mixture to achieve a KF of 3.9% w/w. Dichloromethane (1760 mL) was charged to the reactor and the temperature was stabilized at 35° C. The mixture was seeded with tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (6.4 g, 0.0067 mol, 0.02 equiv). A portion of dichloromethane (32 mL) was used to rinse forward the seeds. The seeded mixture was stirred for 2 h at 35° C. and cooled to 0° C. over a period of 2 h. The slurry was further stirred for a period of 3.5 h after which it was filtered and washed with dichloromethane (320 mL). The isolated material was dried in a vacuum oven to afford tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (103.5 g, 0.109 mol, 35% molar yield)

Example 6d

To a jacketed glass reactor (reactor A) equipped with overhead stirring, was charged 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (320 g, 0.311 mol, 1 equiv). Methanol (3200 mL) was charged to the reactor and the temperature was stabilized between 45 and 55° C. (47° C.). A previously prepared solution of di-tert-butyl-dicarbonate (81.60 g, 0.374 mol, 1.20 equiv) in methanol (80 mL) was added to the reaction solution over 3 minutes. The charge was completed with a rinse through of methanol (80 mL). After 6 h the reaction was sampled and deemed complete by HPLC analysis (consumption of 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-

(((2R,3R,4R,5R)-3,5-dihydroxy-5-methyl-4-(methylamino) tetrahydro-2H-pyran-2-yl)oxy)-2-hydroxycyclohexyl)oxy)-3,4-dihydro-2H-pyran-6-yl)methyl)carbamate, formula (4a),).

To a second jacketed glass reactor (reactor B) equipped with overhead stirring, was charged water (2810 g) and sodium hydroxide (131.2 g, 3.280 mol, 10.54 equiv). This basic solution was cooled to 10° C. Sodium dithionite (401.9 g, 2.308 mol, 7.42 equiv) was charged to the solution and the temperature was stabilized at 12.5° C.

The reaction mixture containing intermediate tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((((4-nitrobenzyl)oxy)carbonyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate (reactor A) was transfer to the sodium dithionite mixture (reactor B) over a period of 1 h while maintaining the temperature of the dithionite reaction mixture at 12.5° C. The transfer was completed with a charge of methanol (160 mL). At the conclusion of the addition, the reaction mixture was heated to 20° C. over a period of 3 h. After 18 h the reaction was sampled and deemed complete by HPLC analysis (consumption of tert-butyl ((2R,3R,4R,5R)-2-(((1S,2S,3R,4S,6R)-3-(((2S,3R)-6-(((((4-aminobenzyl)oxy)carbonyl)amino)methyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate). The reaction was concentrated under vacuum with a maximum jacket temperature of 35° C. to a final volume of 4160 mL. Isopropyl acetate (1280 mL) and water (1920 mL) were charged to the reaction mixture. The layers were mixed by agitation at 35° C. and then allowed to separate after which the lower aqueous layer aqueous layer (AP1) and the upper organic layer (OP1) were transferred to receivers. AP1 was returned to the reactor and further extracted with another portion of isopropyl acetate (640 mL) to generate aqueous layer 2 (AP2) and organic layer (OP2). AP2 was sent to waste while OP2 was combined with OP1 in the reactor. This combined product rich organic solution was washed with two portions of 6.5% sodium bicarbonate solution (2 portions of 960 mL). The washed organic phases were concentrated under vacuum to a volume target of 960 mL. Isopropyl acetate (960 mL) was charged to the reactor and a second azeotropic distillation was performed with a volume target of 960 mL. Another portion of Isopropyl acetate (960 mL) was charged to the reactor and a third azeotropic distillation was performed to a volume target of 1280 mL. The temperature was stabilized at 37.5° C. and water (26 mL) was charged to the mixture to achieve a KF of 2.1% w/w. Dichloromethane (1280 mL) was charged to the reactor and the temperature was stabilized at 15.1° C. The mixture was seeded with tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (6.4 g, 0.0067 mol, 0.02 equiv). A portion of dichloromethane (32 mL) was used to rinse forward the seeds. The seeded mixture was stirred for 2 h at 15° C. and cooled to 0° C. over a period of 2 h. The slurry was further stirred for a period of 3.5 h after which it was filtered and washed with dichloromethane (320 mL). The isolated material was dried in a vacuum oven to afford tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (257.5 g, 0.271 mol, 87% molar yield)

Example 6e

To a jacketed glass reactor (reactor A) equipped with overhead stirring, was charged 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a), (320 g, 0.311 mol, 1 equiv). Methanol (3200 mL) was charged to the reactor and the temperature was stabilized between 45 and 55° C. (47° C.). A previously prepared solution of di-tert-butyl-dicarbonate (81.60 g, 0.374 mol, 1.20 equiv) in methanol (80 mL) was added to the reaction solution over 3 minutes. The charge was completed with a rinse through of methanol (80 mL). After 8 h the reaction was sampled and deemed complete by HPLC analysis (consumption of 4-nitrobenzyl (((2S,3R)-3-((tert-butoxycarbonyl)amino)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino)tetrahydro-2H-pyran-2-yl)oxy)-2-hydroxycyclohexyl)oxy)-3,4-dihydro-2H-pyran-6-yl)methyl)carbamate, formula (4a)).

To a second jacketed glass reactor (reactor B) equipped with overhead stirring, was charged water (2170 g) and sodium hydroxide (118.4 g, 2.960 mol, 9.51 equiv). This basic solution was cooled to 0° C. Sodium dithionite (363.5 g, 2.088 mol, 6.71 equiv) was charged to the solution and the temperature was stabilized at 2.5° C.

The reaction mixture containing intermediate tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((((4-nitrobenzyl)oxy)carbonyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate (reactor A) was transfer to the sodium dithionite mixture (reactor B) over a period of 5 h while maintaining the temperature of the dithionite reaction mixture at 2.5° C. The transfer was completed with a charge of methanol (160 mL). At the conclusion of the addition, the reaction mixture was heated to 35° C. over a period of 1 h. After 4 h the reaction was sampled and deemed complete by HPLC analysis (consumption of tert-butyl ((2R,3R,4R,5R)-2-(((1S,2S,3R,4S,6R)-3-(((2S,3R)-6-(((((4-aminobenzyl)oxy)carbonyl)amino)methyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate). The reaction was concentrated under vacuum with a maximum jacket temperature of 35° C. to a final volume of 4160 mL. Isopropyl acetate (1280 mL) and water (1920 mL) were charged to the reaction mixture. The layers were mixed by agitation at 35° C. and then allowed to separate after which the lower aqueous layer aqueous layer (AP1) and the upper organic layer (OP1) were transferred to receivers. AP1 was returned to the reactor and further extracted with another portion of isopropyl acetate (640 mL) to generate aqueous layer 2 (AP2) and organic layer (OP2). AP2 was sent to waste while OP2 was combined with OP1 in the reactor. This combined product rich organic solution was washed with two portions of 6.5% sodium bicarbonate solution (2 portions of 960 mL). The washed organic phases were concentrated under vacuum to a volume target of 960 mL. Isopropyl acetate (960 mL) was charged to the reactor and a second azeotropic distillation was performed with a volume target of 960 mL. Another portion of Isopropyl acetate (960 mL) was charged to the reactor and a third azeotropic distillation was performed to a volume target of 1600 mL. The temperature was stabilized at 37.5° C. and water (29 mL) was charged to the mixture to achieve a KF of 3.5% w/w. Dichloromethane (1600 mL) was charged to the reactor and the temperature was stabilized at 30° C. The mixture was seeded with tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (6.4 g, 0.0067 mol, 0.02 equiv). A portion of dichloromethane (32 mL) was used to rinse forward the seeds. The seeded mixture was stirred for 2 h at 30° C. and cooled to 0° C. over a period of 2 h. The slurry was further stirred for a period of 3.5 h after which it was filtered and washed with dichloromethane (320 mL). The isolated material was dried in a vacuum oven to afford tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (259.50 g, 0.273 mol, 88% molar yield)

Example 7: Example Procedures for the Preparation of tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), from tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a)

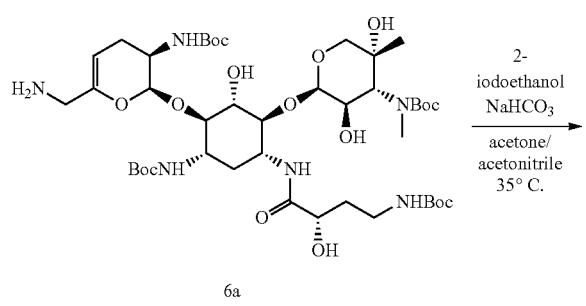

6a

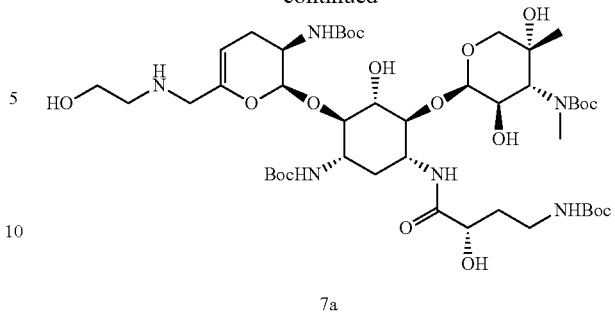

7a

Example 7a

To a jacketed glass reactor equipped with overhead stirring, was charged tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a), (250 g, 0.263 mol, 1 equiv). Acetonitrile (1250 mL) was charged to the reactor and the temperature was stabilized between 15 and 30° C. (27.4° C.). The mixture was concentrated under vacuum to a final volume target of 500 mL. The solution was sampled for water content by KF which provided a result of 0.27% w/w. An additional portion of acetonitrile (750 mL) was charged to the reactor and a second azeotropic distillation was performed to a volume target of 500 mL. The mixture was sampled for KF and a result of 0.08% w/w was obtained. The reaction temperature was stabilized at 29.9° C. and acetone (1250 mL) was charged to the mixture. The reaction was heated and the temperature stabilized at 40° C. Sodium bicarbonate (44.25 g, 0.527 mol, 2 equiv) was charged to the reaction mixture followed by 2-iodoethanol (65.2 g, 29.6 mL, 0.379 mol, 1.44 equiv). After 23 h the reaction was sampled and deemed complete by HPLC analysis (consumption of tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a),). The reaction was cooled to 22.7° C. and 1,4-diazabicyclo[2.2.2]octane (60.0 g, 0.535 mol, 2.03 equiv) was charged as a solid. The destruction of 2-iodoethanol was monitored by a GC method and after 18 h the quench of this reagent was deemed complete. Water (1250 mL) and isopropyl acetate (1250 mL) were charged to the reaction mixture. The reactor contents were agitated by 25 min and the layers allowed to separate. The lower aqueous layer (AP1) and the upper organic layer (OP1) were collected in receivers. AP1 was returned to the reactor and a second portion of isopropyl acetate (750 mL) was charged. The reactor contents were agitated for 30 minutes and the layers allowed to separate. The lower aqueous layer (AP2) and the upper organic layer (OP2) were collected in receivers. OP1 and OP2 were combined in the reactor and extracted with two portions of saturated sodium chloride solution (750 mL, prepared by dissolving 100 g NaCl/290 mL of water). The washed organic phase (OP4) was concentrated under vacuum to a volume target of 500 mL. Acetonitrile (2550 mL) was charged to the reactor. A second azeotropic vacuum distillation was performed to a volume target of 2050 mL. Isopropyl acetate (200 mL) was charged to the mixture. Water (35.4 mL) was charged to the mixture until a KF of 2.0% was obtained. The reactor contents were heated to 75° C. upon which a solution was obtained. The reaction mixture was cooled to 65° C. and seeded with tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl) carbamate, formula (7a), (5 g, 0.0050 mol, 0.02 equiv). Stirring was maintained at 65° C. for 8 h during which a thick slurry formed. The mixture was cooled from 65° C. to 2.5° C. over a period of 12 h. The slurry was filtered and washed with acetonitrile (900 mL) and dried in a vacuum oven to afford tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (203.8 g, 0.205 mol, 78% yield).

Example 7b

To a jacketed glass reactor equipped with overhead stirring, was charged tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate, formula (6a), (250 g, 0.263 mol, 1 equiv). Acetonitrile (1250 mL) was charged to the reactor and the temperature was stabilized between 15 and 30° C. (30° C.). The mixture was concentrated under vacuum to a final volume target of 500 mL. The solution was sampled for water content by KF which provided a result of 0.18% w/w. An additional portion of acetonitrile (750 mL) was charged to the reactor and a second azeotropic distillation was performed to a volume target of 500 mL. The mixture was sampled for KF and a result of 0.075% w/w was obtained. The reaction temperature was stabilized at 29.9° C. and acetone (1250 mL) was charged to the mixture. The reaction was heated and the temperature stabilized at 40° C. Sodium bicarbonate (44.25 g, 0.527 mol, 2.0 equiv) was charged to the reaction mixture followed by 2-iodoethanol (56.6 g, 25.7 mL, 0.329 mol, 1.25 equiv). After 56 h the reaction was sampled and deemed complete by HPLC analysis (consumption of tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate, formula (6a),). The reaction was cooled to 22.7° C. and 1,4-diazabicyclo[2.2.2]octane (60.0 g, 0.535 mol, 2.0 equiv) was charged as a solid. The destruction of 2-iodoethanol was monitored by a GC method and after 18 h the quench of this reagent was deemed complete. Water (1250 mL) and isopropyl acetate (1250 mL) were charged to the reaction mixture. The reactor contents were agitated by 25 min and the layers allowed to separate. The lower aqueous layer (AP1) and the upper organic layer (OP1) were collected in receivers. AP1 was returned to the reactor and a second portion of isopropyl acetate (750 mL) was charged. The reactor contents were agitated for 30 minutes and the layers allowed to separate. The lower aqueous layer (AP2) and the upper organic layer (OP2) were collected in receivers. OP1 and OP2 were combined in the reactor and extracted with two portions of saturated sodium chloride solution (750 mL, prepared by dissolving 100 g NaCl/290 mL of water). The washed organic phase (OP4) was concentrated under vacuum to a volume target of 500 mL. Acetonitrile (2550 mL) was charged to the reactor. A second azeotropic vacuum distillation was performed to a volume target of 1800 mL. Isopropyl acetate (200 mL) was charged to the mixture. Water (22.8 mL) was charged to the mixture until a KF of 1.46% was obtained. The reactor contents were heated to 75° C. upon which a solution was obtained. The reaction mixture was cooled to 62.5° C. and seeded with tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl) carbamate, formula (7a), (5 g, 0.0050 mol, 0.02 equiv). Stirring was maintained at 62.5° C. for 5 h during which a thick slurry formed. The mixture was cooled from 65° C. to 2.5° C. over a period of 12 h. The slurry was filtered and washed with acetonitrile (900 mL) and dried in a vacuum oven to afford tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (208.1 g, 0.220 mol, 83% molar yield)

Example 7c

To a jacketed glass reactor equipped with overhead stirring, was charged tert-butyl ((2R,3R,4R,5R)-2-(((1S,2S,3R,4S,6R)-3-(((2S,3R)-6-(aminomethyl)-3-((tert-butoxycarbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl) carbamate, formula (6a), (250 g, 0.263 mol, 1 equiv). Acetonitrile (1250 mL) was charged to the reactor and the temperature was stabilized between 15 and 30° C. (24.3° C.). The mixture was concentrated under vacuum to a final volume target of 500 mL. The solution was sampled for water content by KF which provided a result of 0.22% w/w. An additional portion of acetonitrile (750 mL) was charged to the reactor and a second azeotropic distillation was performed to a volume target of 500 mL. The mixture was sampled for KF and a result of 0.097% w/w was obtained. The reaction temperature was stabilized at 29.9° C. and acetone (1250 mL) was charged to the mixture. The reaction was heated and the temperature stabilized at 29.9° C. Sodium bicarbonate (44.25 g, 0.527, 2.0 equiv) was charged to the reaction mixture followed by 2-iodoethanol (44.4 g, 20.14 mL, 0.258 mol, 0.98 equiv). After 43 h an additional portion of 2-iodoethanol (0.25 mL) was added to the reaction mixture. After 9.5 hours a third portion of 2-iodoethanol (0.3 mL) was added to the reaction mixture. After an additional 2 h, the reaction was sampled and deemed complete by HPLC analysis (consumption of tert-butyl ((2R,3R,4R,5R)-2-(((1S,2S,3R,4S,6R)-3-(((2S,3R)-6-(aminoethyl)-3-((tert-butoxycarbonyl)amino)-3,4-dihydro-2H-pyran-2-yl)oxy)-4-((tert-butoxycarbonyl)amino)-6-((S)-4-

((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, formula (6a),). The reaction was cooled to 22.7° C. and 1,4-diazabicyclo[2.2.2]octane (60.0 g, 0.535 mol, 2.03 equiv) was charged as a solid. The destruction of 2-iodoethanol was monitored by a GC method and after 10 h the quench of this reagent was deemed complete. Water (1250 mL) and isopropyl acetate (1250 mL) were charged to the reaction mixture. The reactor contents were agitated by 25 min and the layers allowed to separate. The lower aqueous layer (AP1) and the upper organic layer (OP1) were collected in receivers. AP1 was returned to the reactor and a second portion of isopropyl acetate (750 mL) was charged. The reactor contents were agitated for 30 minutes and the layers allowed to separate. The lower aqueous layer (AP2) and the upper organic layer (OP2) were collected in receivers. OP1 and OP2 were combined in the reactor and extracted with two portions of saturated sodium chloride solution (750 mL, prepared by dissolving 100 g NaCl/290 mL of water). The washed organic phase (OP4) was concentrated under vacuum to a volume target of 500 mL. Acetonitrile (2550 mL) was charged to the reactor. A second azeotropic vacuum distillation was performed to a volume target of 1550 mL. Isopropyl acetate (200 mL) was charged to the mixture. Water (10.7 mL) was charged to the mixture until a KF of 0.85% was obtained. The reactor contents were heated to 75° C. upon which a solution was obtained. The reaction mixture was cooled to 57° C. and seeded with tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl) carbamate, formula (7a), (5 g, 0.0050 mol, 0.02 equiv). Stirring was maintained at 57° C. for 2 h during which a thick slurry formed. The mixture was cooled from 65° C. to 2.5° C. over a period of 12 h. The slurry was filtered and washed with acetonitrile (900 mL) and dried in a vacuum oven to afford tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (218.1 g, 0.220 mol, 83% molar yield)

Example 8: Example Procedures for the Preparation of plazomicin from tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl) amino)-6-(((2-hydroxyethyl)amino)methyl)-3,4-dihydro-2H-pyran-2-yl)oxy)-2-hydroxycyclohexyl) oxy)-3,5-dihydroxy-5-methyltetrahydro-2H-pyran-4-yl)(methyl)carbamate, Formula (7a) and Regeneration of CG-50 Resin Bed

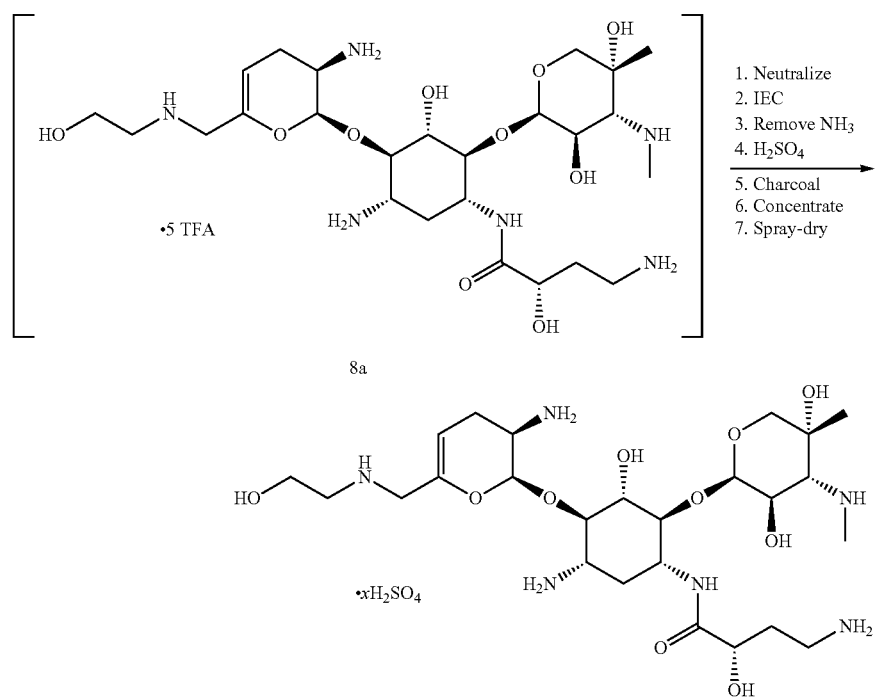

Example 8a

To a jacketed glass reactor (reactor A) equipped with overhead stirring, was charged tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (150 g, 0.151 mol, 1 equiv) and dichloromethane (750 mL). The mixture was stirred between 0 and 5° C. (0.6° C.). Trifluoroacetic acid was added slowly to the reaction mixture maintaining the temperature between 0 and 5° C. [note exothermic addition]. At the conclusion of the addition, the reaction solution was heated to 22.5° C. and held at that temperature for 2 h. The reaction mixture was concentrated by distillation under vacuum to a final volume target of 450 mL. The concentrated reaction mixture was held at 22.5° C. for an additional 2 h after which the temperature was stabilized between 0 and 10° C. (3.0° C.).

To a second jacketed glass reactor (reactor B) equipped with overhead stirring, was charged water (375 mL) which was cooled to a temperature between 0 and 5° C. (2.5° C.). The contents of reactor A were transferred to the contents of reactor B over 45 minutes maintaining the temperature between 0 and 10° C. [note exothermic addition]. Isopropyl acetate was charged to the reaction mixture to produce a biphasic mixture. The reactor contents were mixed via overhead stirring and then the stirring halted to allow the layers to separate. The lower product rich aqueous layer (AP1) and the upper organic layer were separated (OP1). OP1 was transfer back to the reactor and water (75 mL) was charged to the mixture. The reactor contents were mixed via overhead stirring and then the stirring halted to allow the layers to separate. The lower product rich aqueous layer (AP2) and the upper organic layer (OP2) were collected. OP2 was returned to the reactor and charged with water (75 mL). The reactor contents were mixed via overhead stirring and then the stirring halted to allow the layers to separate. The lower product rich aqueous layer (AP3) and the upper organic layer (OP3) were collected. The three product rich aqueous layers (AP1, AP2, and AP3) were returned to the reactor and combined. The pH of the combined organic layer was measured as 0.15. Isopropyl acetate (450) was charged to the combined aqueous phases. The reactor contents were mixed via overhead stirring and then the stirring halted to allow the layers to separate. The lower product rich aqueous layer (AP4) and the upper organic layer (OP4) were collected. The pH of the combined AP4 was measured as 0.73. AP4 was returned to the reactor. Isopropyl acetate (450) was charged to the reactor. The reactor contents were mixed via overhead stirring and then the stirring halted to allow the layers to separate. The lower product rich aqueous layer (AP5) and the upper organic layer (OP5) were collected. The pH of the AP5 was measured as 1.78. AP5 was returned to the reactor. Isopropyl acetate (450) was charged to the reactor. The reactor contents were mixed via overhead stirring and then the stirring halted to allow the layers to separate. The lower product rich aqueous layer (AP6) and the upper organic layer (OP6) were collected. The pH of the AP6 was measured as 2.95. AP6 was returned to the reactor and the pH adjusted to between 5.8 and 6.2 (final pH 6.01) using a 1% ammonia solution (34.7 mL). The temperature was maintained between 0 and 10° C. during the pH adjustment. Water (ca 820 mL) was charged to the reaction mixture until a final volume of 1350 mL. The pH was measured again (5.67) and adjusted to between 5.8 and 6.2 (6.01) using 1% ammonia solution (11.7 mL). The conductivity of the solution was measured as 15.36 mS/cm.

This solution of crude plazomicin was charged to an XK-50/100 column packed with CG-50 resin (325.5 g) in the ammonium form with a headspace filled with water. The column temperature was stabilized at 13° C. The crude solution was charged in downflow mode at a linear flow rate between 10 and 20 cm/h (ca 9.2 mL/min). After the crude solution had been charged to the resin bed. Water (1 column volume, 1620 mL) was charged in downflow mode at a linear flow rate between 10 and 20 cm/h (9.2 mL/min). At the conclusion of the water charge, a 0.43% ammonia solution (prepared from 86.7 g of 25% ammonia in 5 L of water) was charged to the column in down flow mode until plazomicin had eluted from the column as judged from the UV absorbance trace at 210 nm. After the plazomicin elution had been deemed complete the column was further washed with a 5% ammonia solution in downflow mode. The product rich fractions (#36-58) were combined to afford 6520 mL of a purified plazomicin freebase solution. The ammonia content of the solution was measure by ion chromatography as 2720 µg/mL and the plazomicin freebase concentration was measure by UPLC as 1.17% w/v. The solution was processed by reverse osmosis using an XLE membrane in diafiltration mode until the ammonia (µg/mL) to plazomicin (% w/v) was below 20. 6 diavolumes of water were processed to achieve this criterion. The temperature was maintained below 10° C. during the ammonia removal by diafiltration process. After the ammonia removal process the pH of the purified plazomicin solution was adjusted to 6.0 using 6 M sulfuric acid solution (57.5). The temperature during the pH adjustment was maintained between 0 and 5° C. The neutralized solution was passed through a pre-washed Zetacarbon R55 charcoal cartridge at a flow rate of 72 L/h.m2 (18 mL/min). After the filtration, the cartridge was washed with water (1068 mL) and the wash was combined with the filtrated plazomicin solution. The combined filtrate and wash were concentrated to 540 mL using reverse osmosis with an XLE membrane in nanofiltration mode. The concentrated solution was passed through a 0.22 micron filter and isolated via spray drying using a Buchi laboratory spray dryer (89.05 g, 0.106 mol, 70% molar yield).

Example 8b—Regeneration of Resin

An XK-50/100 column containing CG-50 resin (326 g) was regenerated by the following steps. 4% Sodium hydroxide solution (0.49 kg of NaOH in 11.8 L of water) was charged in upflow mode until a conductivity of 110 mS/cm was achieved in the effluent. Then water was charged in upflow mode until a conductivity of 1.5 mS/cm in the effluent was achieved. 2% Sulfuric acid solution (prepared from 0.10 kg concentrated sulfuric acid in 4.9 L of water) was charged in upflow mode until a conductivity of mS/cm in the effluent was achieved. Water (4782 mL) was charged in upflow mode until a final conductivity of 4.8 mS/cm was achieved. 2% ammonia solution (prepared from 400 g 25% ammonia in 9.6 L of water) was charged in upflow mode. The final conductivity of the effluent was 970 µS/cm (pH 12.04). The resin was allowed to settle without flow for 1 h. Water (3419 mL) was charged in downflow mode (13.1 mL/min).

The resin bed packing was tested by the application of an ammonia trifluoroacetate pulse. An ammonia trifluoroacetate solution was prepared by dissolving ammonium trifluoroacetate (1.397 g) in water (106 mL). This solution of 0.1 M ammonium trifluoroacetate (27.5 mL) was charged directly above the surface of the CG-50 resin bed in liquid piston mode. Water was charged in downflow mode until the UV absorbance of the ammonium trifluoroacetate pulse could be observed at 210 nm. The resin bed was deemed packed and suitable for use in the purification of crude plazomicin.

Example 8c

To a jacketed glass reactor (reactor A) equipped with overhead stirring, was charged tert-butyl ((2R,3R,4R,5R)-

2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (150 g, 0.151 mol, 1 equiv) and dichloromethane (750 mL). The mixture was stirred between 0 and 5° C. (0.0° C.). Trifluoroacetic acid was added slowly to the reaction mixture maintaining the temperature between 0 and 5° C. [note exothermic addition]. At the conclusion of the addition, the reaction solution was heated to 22.5° C. and held at that temperature for 1.5 h. The reaction mixture was concentrated by distillation under vacuum to a final volume target of 450 mL. The concentrated reaction mixture was held at 22.5° C. for an additional 8 h after which the temperature was stabilized between 0 and 10° C. (5.0° C.).

To a second jacketed glass reactor (reactor B) equipped with overhead stirring, was charged water (375 mL) which was cooled to a temperature between 0 and 5° C. (0.3° C.). The contents of reactor A were transferred to the contents of reactor B over 19 minutes maintaining the temperature between 0 and 10° C. [note exothermic addition]. Isopropyl acetate was charged to the reaction mixture to produce a biphasic mixture. The reactor contents were mixed via overhead stirring and then the stirring halted to allow the layers to separate. The lower product rich aqueous layer (AP1) and the upper organic layer were separated (OP1). OP1 was transfer back to the reactor and water (75 mL) was charged to the mixture. The reactor contents were mixed via overhead stirring and then the stirring halted to allow the layers to separate. The lower product rich aqueous layer (AP2) and the upper organic layer (OP2) were collected. OP2 was returned to the reactor and charged with water (75 mL). The reactor contents were mixed via overhead stirring and then the stirring halted to allow the layers to separate. The lower product rich aqueous layer (AP3) and the upper organic layer (OP3) were collected. The three product rich aqueous layers (AP1, AP2, and AP3) were returned to the reactor and combined. The pH of the combined organic layer was measured as 0.49. Isopropyl acetate (450) was charged to the combined aqueous phases. The reactor contents were mixed via overhead stirring and then the stirring halted to allow the layers to separate. The lower product rich aqueous layer (AP4) and the upper organic layer (OP4) were collected. The pH of the combined AP4 was measured as 0.85. AP4 was returned to the reactor. Isopropyl acetate (450) was charged to the reactor. The reactor contents were mixed via overhead stirring and then the stirring halted to allow the layers to separate. The lower product rich aqueous layer (AP5) and the upper organic layer (OP5) were collected. The pH of the AP5 was measured as 1.72. AP5 was returned to the reactor. Isopropyl acetate (450) was charged to the reactor. The reactor contents were mixed via overhead stirring and then the stirring halted to allow the layers to separate. The lower product rich aqueous layer (AP6) and the upper organic layer (OP6) were collected. The pH of the AP6 was measured as 2.86. AP6 was returned to the reactor and the pH adjusted to between 5.8 and 6.2 (final pH 5.99) using a 1% ammonia solution (21 mL). The temperature was maintained between 0 and 10° C. during the pH adjustment. Water (ca 820 mL) was charged to the reaction mixture until a final volume of 1350 mL. The pH was measured again (5.54) and adjusted to between 5.8 and 6.2 (6.01) using 1% ammonia solution (10 mL). The conductivity of the solution was measured as 14.92 mS/cm.

This solution of crude plazomicin was charged to an XK-50/100 column packed with CG-50 resin (325.5 g) in the ammonium form with a headspace filled with water. The column temperature was stabilized at 20° C. The crude solution was charged in downflow mode at a linear flow rate between 10 and 20 cm/h (ca 9.2 mL/min). After the crude solution had been charged to the resin bed. Water (1 column volume, 1620 mL) was charged in downflow mode at a linear flow rate between 10 and 20 cm/h (9.2 mL/min). At the conclusion of the water charge, a 0.50% ammonia solution (prepared from 102 g of 25% ammonia in 5 L of water) was charged to the column in down flow mode until plazomicin had eluted from the column as judged from the UV absorbance trace at 210 nm. The ammonia solution was charged at a linear flow rate of 38 cm/h (12.4 mL/min). The product rich fractions (#34-50) were combined to afford 4800 mL of a purified plazomicin freebase solution. The ammonia content of the solution was measure by ion chromatography as 3200 μg/mL and the plazomicin freebase concentration was measure by UPLC as 1.52% w/v. The solution was processed by reverse osmosis using an XLE membrane in diafiltration mode until the ammonia (μg/mL) to plazomicin (% w/v) was below 20. 9 diavolumes of water were processed to achieve this criterion. The temperature was maintained below 10° C. during the ammonia removal by diafiltration process. After the ammonia removal process the pH of the purified plazomicin solution was adjusted to 6.47 using 6 M sulfuric acid solution (52.5). The temperature during the pH adjustment was maintained between 0 and 5° C. The neutralized solution was passed through a pre-washed Zetacarbon R55 charcoal cartridge at a flow rate of 72 L/h.m2 (15 mL/min). After the filtration, the cartridge was washed with water (1068 mL) and the wash was combined with the filtrated plazomicin solution. The combined filtrate and wash were concentrated to 540 mL using reverse osmosis with an XLE membrane in nanofiltration mode. The concentrated solution was passed through a 0.22 micron filter and isolated via spray drying using a Buchi laboratory spray dryer (88.42 g, 0.106 mol, 70% molar yield).

Example 8d

To a jacketed glass reactor (reactor A) equipped with overhead stirring, was charged tert-butyl ((2R,3R,4R,5R)-2-(((1S,2S,3R,4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, formula (7a), (150 g, 0.151 mol, 1 equiv) and dichloromethane (750 mL). The mixture was stirred between 0 and 5° C. (0.9° C.). Trifluoroacetic acid was added slowly to the reaction mixture maintaining the temperature between 0 and 5° C. [note exothermic addition]. At the conclusion of the addition, the reaction solution was heated to 22.5° C. and held at that temperature for 1.5 h. The reaction mixture was concentrated by distillation under vacuum to a final volume target of 450 mL. The concentrated reaction mixture was held at 22.5° C. for an additional 6 h after which the temperature was stabilized between 0 and 10° C. (6.5° C.).

To a second jacketed glass reactor (reactor B) equipped with overhead stirring, was charged water (375 mL) which was cooled to a temperature between 0 and 5° C. (3.5° C.). The contents of reactor A were transferred to the contents of reactor B over 7 minutes maintaining the temperature between 0 and 10° C. [note exothermic addition]. Isopropyl acetate was charged to the reaction mixture to produce a biphasic mixture. The reactor contents were mixed via overhead stirring and then the stirring halted to allow the layers to separate. The lower product rich aqueous layer (AP1) and the upper organic layer were separated (OP1). OP1 was transfer back to the reactor and water (75 mL) was charged to the mixture. The reactor contents were mixed via overhead stirring and then the stirring halted to allow the layers to separate. The lower product rich aqueous layer (AP2) and the upper organic layer (OP2) were collected. OP2 was returned to the reactor and charged with water (75 mL). The reactor contents were mixed via overhead stirring and then the stirring halted to allow the layers to separate. The lower product rich aqueous layer (AP3) and the upper organic layer (OP3) were collected. The three product rich aqueous layers (AP1, AP2, and AP3) were returned to the reactor and combined. The pH of the combined organic layer was measured as 0.47. Isopropyl acetate (450) was charged to the combined aqueous phases. The reactor contents were mixed via overhead stirring and then the stirring halted to allow the layers to separate. The lower product rich aqueous layer (AP4) and the upper organic layer (OP4) were collected. The pH of the combined AP4 was measured as 0.83. AP4 was returned to the reactor. Isopropyl acetate (450) was charged to the reactor. The reactor contents were mixed via overhead stirring and then the stirring halted to allow the layers to separate. The lower product rich aqueous layer (AP5) and the upper organic layer (OP5) were collected. The pH of the AP5 was measured as 1.90. AP5 was returned to the reactor. Isopropyl acetate (450) was charged to the reactor. The reactor contents were mixed via overhead stirring and then the stirring halted to allow the layers to separate. The lower product rich aqueous layer (AP6) and the upper organic layer (OP6) were collected. The pH of the AP6 was measured as 3.1. AP6 was returned to the reactor and the pH adjusted to between 5.8 and 6.2 (final pH 6.04) using a 1% ammonia solution (35 mL). The temperature was maintained between 0 and 10° C. during the pH adjustment. Water (ca 820 mL) was charged to the reaction mixture until a final volume of 1350 mL. The pH was measured again (5.83) and adjusted to between 5.8 and 6.2 (6.01) using 1% ammonia solution (5 mL). The conductivity of the solution was measured as 15.29 mS/cm.

This solution of crude plazomicin was charged to an XK-50/100 column packed with CG-50 resin (325.5 g) in the ammonium form with a headspace filled with water. The column temperature was stabilized at 27° C. The crude solution was charged in downflow mode at a linear flow rate between 10 and 20 cm/h (ca 9.2 mL/min). After the crude solution had been charged to the resin bed. Water (1 column volume, 1620 mL) was charged in downflow mode at a linear flow rate between 10 and 20 cm/h (9.2 mL/min). At the conclusion of the water charge, a 0.50% ammonia solution (prepared from 102 g of 25% ammonia in 5 L of water) was charged to the column in down flow mode until plazomicin had eluted from the column as judged from the UV absorbance trace at 210 nm. The ammonia solution was charged at a linear flow rate of 38 cm/h (12.4 mL/min). The product rich fractions (#31-45) were combined to afford 4072 mL of a purified plazomicin freebase solution. The ammonia content of the solution was measure by ion chromatography as 4060 µg/mL and the plazomicin freebase concentration was measure by UPLC as 1.52% w/v. The solution was processed by reverse osmosis using an XLE membrane in diafiltration mode until the ammonia (µg/mL) to plazomicin (% w/v) was below 20. 5 diavolumes of water were processed to achieve this criterion. The temperature was maintained below 10° C. during the ammonia removal by diafiltration process. After the ammonia removal process the pH of the purified plazomicin solution was adjusted to 6.74 using 6 M sulfuric acid solution (56). The temperature during the pH adjustment was maintained between 0 and 5° C. The neutralized solution was passed through a pre-washed Zetacarbon R55 charcoal cartridge at a flow rate of 72 L/h.m2 (15 mL/min). After the filtration, the cartridge was washed with water (1068 mL) and the wash was combined with the filtrated plazomicin solution. The combined filtrate and wash were concentrated to 540 mL using reverse osmosis with an XLE membrane in nanofiltration mode. The concentrated solution was passed through a 0.22 micron filter and isolated via spray drying using a Buchi laboratory spray dryer (95.86 g, 0.114 mol, 76% yield).

The invention claimed is:
1. A compound selected from the group consisting of
(i) a compound of formula (4):

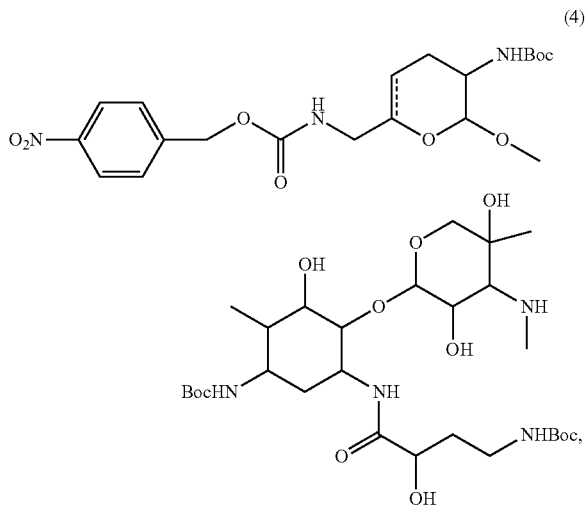

or a salt thereof, or a solvate thereof, or an enantiomer thereof, or a diastereomer thereof;
(ii) a compound of formula (4a):

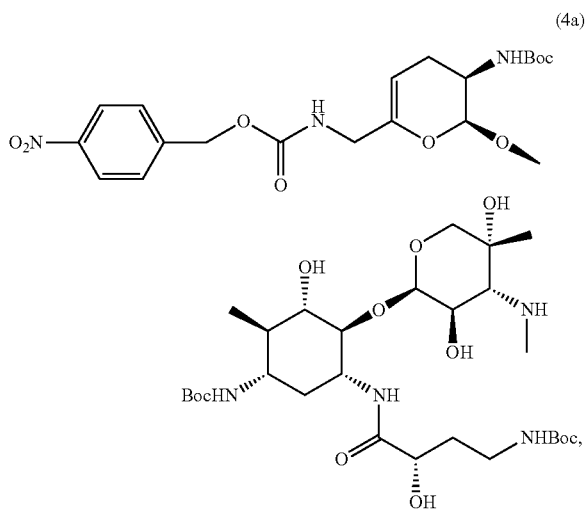

or a salt thereof, or a solvate thereof;
(iii) crystalline tert-butyl ((2S,3R)-2-(((1R,2S,3 S,4R,6S)-6-((tert-butoxycarbonyl)amino)-4-((S)-4-((tert-butoxycarbonyl)amino)-2-hydroxybutanamido)-3-(((2R,3R, 4R,5R)-3,5-dihydroxy-5-methyl-4-(methylamino) tetrahydro-2H-pyran-2-yl)oxy)-2-hydroxycyclohexyl) oxy)-6-(((((4-nitrobenzyl)oxy)carbonyl)amino) methyl)-3,4-dihydro-2H-pyran-3-yl)carbamate, Formula (4a), or a solvate thereof;

(iv) crystalline tert-butyl ((2R,3R,4R,5R)-2-(((1S,2S,3R, 4S,6R)-3,4(2S,3R)-6-(aminomethyl)-3-((tert-butoxy-carbonyl)amino)-3,4-dihydro-2H-pyran-2-yl)oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof;

(v) a compound of formula (7):

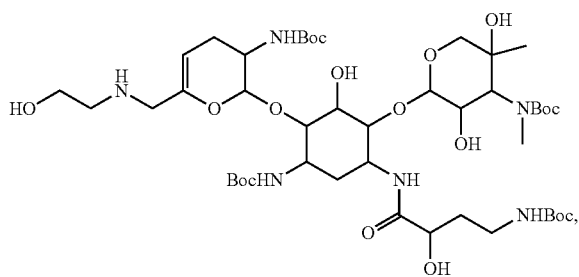

or a salt thereof, or solvate thereof, or an enantiomer thereof, or a diastereomer thereof;

(vi) a compound of formula (7a):

(7a)

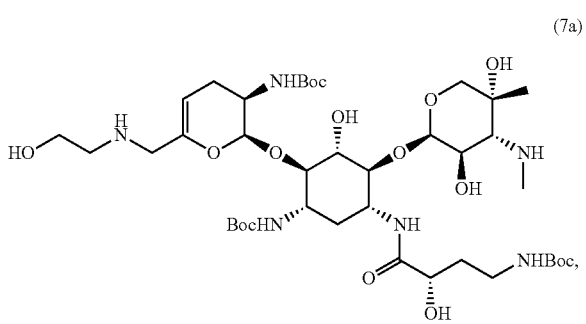 [SMILES: CN[C@@H]1[C@@H](O)[C@@H](O[C@@H]2[C@@H](O)[C@H](O[C@H]3OC(CNCCO)=CC[C@H]3NC(=O)OC(C)(C)C)[C@@H](NC(=O)OC(C)(C)C)C[C@H]2NC(=O)[C@@H](O)CCNC(=O)OC(C)(C)C)OC[C@]1(C)O]

or a salt thereof, or a solvate thereof; and (vii) crystalline tert-butyl ((2R,3R,4R,5R)-2-(((1S,2S,3R, 4S,6R)-4-((tert-butoxycarbonyl)amino)-6-((S)-4-((tert-butoxycarbonyl)amino)-2-hydroxybutanamido)-3-(((2S,3R)-3-((tert-butoxycarbonyl)amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl)carbamate, Formula (7a), or a solvate thereof.

2. A process for preparing the compound of claim 1, wherein the compound is crystalline tert-butyl ((2S,3R)-2-(((1R,2S,3S,4R,6S)-6-((tert-butoxycarbonyl)amino)-4-((S)-4-((tert-butoxycarbonyl)amino)-2-hydroxybutanamido)-3-(((2R,3R,4R,5R)-3,5-dihydroxy-5-methyl-4-(methylamino) tetrahydro-2H-pyran-2-yl)oxy)-2-hydroxycyclohexyl)oxy)-6-(((((4-nitrobenzyl)oxy)carbonyl)amino)methyl)-3,4-dihydro-2H-pyran-3-yl)carbamate, Formula (4a), or a solvate thereof, wherein the process comprises:
 (a) treating Formula (4a), or a salt thereof, or a solvate thereof, with acetonitrile to produce a solution;
 (b) heating the solution from step (a);
 (c) adding water to the heated solution of step (b);
 (d) cooling the solution from step (c);
 (e) charging the solution from step (d) with a seed crystal; and
 (f) isolating the resulting solids to yield crystalline Formula (4a), or a solvate thereof.

3. A process for preparing the compound of claim 1, wherein the compound is crystalline tert-butyl ((2R,3R,4R, 5R)-2-(((1S,2S,3R,4S,6R)-3-(((2S,3R)-6-(aminomethyl)-3-((tert-butoxycarbonyl)amino)-3,4-dihydro-2H-pyran-2-yl) oxy)-4-((tert-butoxycarbonyl)amino)-6-((S)-4-((tert-butoxycarbonyl)amino)-2-hydroxybutanamido)-2-hydroxycyclohexyl)oxy)-3,5-dihydroxy-5-methyltetrahydro-2H-pyran-4-yl)(methyl)carbamate, Formula (6a), or a solvate thereof, wherein the process comprises:
 (a) treating Formula (6), or a salt thereof, or a solvate thereof, with isopropyl acetate (IPAc) to produce a solution;
 (b) adding water to the solution of step (a) to produce a mixture;
 (c) adding dichloromethane to the mixture from step (b) to produce a mixture;
 (d) charging the mixture from step (c) with a seed crystal;
 (e) isolating the resulting solids to yield crystalline Formula (6a), or a solvate thereof.

4. A process for preparing the compound of claim 1, wherein the compound is crystalline tert-butyl ((2R,3R,4R, 5R)-2-(((1 S,2 S,3R,4 S,6R)-4-((tert-butoxycarbonyl) amino)-6-((S)-4-((tert-butoxycarbonyl)amino)-2-hydroxybutanamido)-3-(((2 S,3R)-3-((tert-butoxycarbonyl) amino)-6-(((2-hydroxyethyl)amino)methyl)-3,4-dihydro-2H-pyran-2-yl)oxy)-2-hydroxycyclohexyl)oxy)-3,5-dihydroxy-5-methyltetrahydro-2H-pyran-4-yl)(methyl) carbamate, Formula (7a), or a solvate thereof, wherein the process comprises:
 (a) treating Formula (7a), or a salt thereof, or a solvate thereof, with isopropyl acetate (IPAc) to produce a solution;
 (b) adding acetonitrile to the solution of step (a) to produce a mixture;
 (c) charging the mixture from step (b) with a seed crystal;
 (d) isolating the resulting solids to yield crystalline Formula (7a), or a solvate thereof.

* * * * *

UNITED STATES PATENT AND TRADEMARK OFFICE
CERTIFICATE OF CORRECTION

| | | |
|---|---|---|
| PATENT NO. | : 11,453,658 B2 | Page 1 of 1 |
| APPLICATION NO. | : 16/850771 | |
| DATED | : September 27, 2022 | |
| INVENTOR(S) | : Trend et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 182 days.

Signed and Sealed this
Eleventh Day of February, 2025

Coke Morgan Stewart
*Acting Director of the United States Patent and Trademark Office*